US011634753B2

(12) United States Patent
Samusik et al.

(10) Patent No.: US 11,634,753 B2
(45) Date of Patent: *Apr. 25, 2023

(54) ON-SLIDE STAINING BY PRIMER EXTENSION

(71) Applicant: The Board of Trustees of the Leland Stanford Junior University, Stanford, CA (US)

(72) Inventors: Nikolay Samusik, Mountain View, CA (US); Garry P. Nolan, Redwood City, CA (US); Yury Goltsev, Stanford, CA (US); David Robert McIlwain, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 17/185,757

(22) Filed: Feb. 25, 2021

(65) Prior Publication Data

US 2022/0025444 A1  Jan. 27, 2022

Related U.S. Application Data

(63) Continuation of application No. 16/679,769, filed on Nov. 11, 2019, now Pat. No. 10,982,263, which is a
(Continued)

(51) Int. Cl.
*C12Q 1/68* (2018.01)
*C12Q 1/6818* (2018.01)
*C12Q 1/6804* (2018.01)

(52) U.S. Cl.
CPC ......... *C12Q 1/6818* (2013.01); *C12Q 1/6804* (2013.01)

(58) Field of Classification Search
CPC ...................................................... C12Q 1/68
(Continued)

(56) References Cited

U.S. PATENT DOCUMENTS 5,063,151 A  11/1991 Kuehn et al.
5,068,178 A * 11/1991 Nowinski ........ G01N 33/56966
435/7.8
(Continued)

FOREIGN PATENT DOCUMENTS

CN  1737160 A  2/2006
CN  101210270 A  7/2008
(Continued)

OTHER PUBLICATIONS

Holmes et al., "89 Analysis of extensive RNA/DNA hybrids in the replication mammalian mitochondrial genome", Abstracts/ Mitochondrion, 2010, 10(2): 225.
(Continued)

*Primary Examiner* — Aaron A Priest
(74) *Attorney, Agent, or Firm* — James S. Keddie; Bozicevic, Field & Francis LLP

(57) ABSTRACT

A method for analyzing planar sample is provided. In some cases the method comprises: (a) labelling the planar sample with a capture agent that is linked to a nucleic acid, wherein the capture agent specifically binds to complementary sites in the planar sample; (b) reading a fluorescent signal caused by extension of a primer that is hybridized to the nucleic acid, using fluorescence microscopy. Several implementations of the method, and multiplexed versions of the same, are also provided.

20 Claims, 24 Drawing Sheets

Specification includes a Sequence Listing.

Related U.S. Application Data continuation of application No. 15/317,019, filed as application No. PCT/US2015/036763 on Jun. 19, 2015, now abandoned, which is a continuation-in-part of application No. 14/560,921, filed on Dec. 4, 2014, now Pat. No. 9,909,167.

(60) Provisional application No. 62/015,799, filed on Jun. 23, 2014, provisional application No. 62/015,799, filed on Jun. 23, 2014.

(58) Field of Classification Search
USPC .......................................................... 435/6.1
See application file for complete search history.

(56) References Cited

U.S. PATENT DOCUMENTS

| | | | |
|---|---|---|---|
| 5,985,548 A | 11/1999 | Collier et al. | |
| 6,531,283 B1 | 3/2003 | Kingsmore et al. | |
| 6,658,780 B2 | 12/2003 | Papadimas et al. | |
| 6,743,592 B1 | 6/2004 | Greene et al. | |
| 6,998,239 B1 | 2/2006 | Gosling et al. | |
| 7,341,831 B2 | 3/2008 | Greene et al. | |
| 7,361,464 B2 | 4/2008 | Greene et al. | |
| 7,846,746 B2 | 12/2010 | Nollau et al. | |
| 8,088,715 B2 | 1/2012 | Bodmer et al. | |
| 8,241,858 B2 | 8/2012 | Eberwine | |
| 8,305,579 B2 | 11/2012 | Treynor et al. | |
| 8,309,306 B2 | 11/2012 | Nolan et al. | |
| 8,445,411 B2 | 5/2013 | Bodmer et al. | |
| 8,530,156 B2 | 9/2013 | Church et al. | |
| 8,658,381 B2 | 2/2014 | Mansson et al. | |
| 8,658,780 B2 * | 2/2014 | Pierce ................. | C12N 15/111 435/6.12 |
| 8,753,824 B2 | 6/2014 | Papin et al. | |
| 8,946,389 B2 | 2/2015 | Gao et al. | |
| 9,376,717 B2 | 6/2016 | Gao et al. | |
| 9,625,387 B2 | 4/2017 | Demos et al. | |
| 9,772,431 B2 | 9/2017 | Millar et al. | |
| 10,000,796 B2 | 6/2018 | Samusik et al. | |
| 10,006,082 B2 | 6/2018 | Samusik et al. | |
| 10,017,808 B2 | 7/2018 | Samusik et al. | |
| 10,370,698 B2 | 8/2019 | Nolan et al. | |
| 10,378,063 B2 | 8/2019 | Stransky et al. | |
| 10,731,202 B2 * | 8/2020 | Lindemann .......... | C12Q 1/6816 |
| 2002/0072053 A1 | 6/2002 | McNally et al. | |
| 2002/0197694 A1 | 12/2002 | Shao | |
| 2003/0032024 A1 | 2/2003 | Lizardi | |
| 2004/0023271 A1 | 2/2004 | Kurn | |
| 2004/0091857 A1 | 5/2004 | Nallur et al. | |
| 2004/0185453 A1 | 9/2004 | Myerson et al. | |
| 2005/0009050 A1 | 1/2005 | Nadeau et al. | |
| 2005/0074774 A1 | 4/2005 | Woudenberg et al. | |
| 2005/0186572 A1 | 8/2005 | Egholm et al. | |
| 2006/0046249 A1 | 3/2006 | Huang et al. | |
| 2007/0020650 A1 | 1/2007 | Kahvejian | |
| 2007/0026430 A1 | 2/2007 | Andersen et al. | |
| 2007/0148645 A1 | 6/2007 | Hoser | |
| 2008/0317325 A1 | 12/2008 | Ortyn et al. | |
| 2009/0023593 A1 | 1/2009 | Eberwine et al. | |
| 2010/0021904 A1 | 1/2010 | Pierce et al. | |
| 2010/0075307 A1 | 3/2010 | Belyaev | |
| 2010/0081134 A1 | 4/2010 | Mirkin et al. | |
| 2010/0120043 A1 * | 5/2010 | Sood ................... | G01N 33/582 435/7.1 |
| 2010/0234450 A1 | 9/2010 | Schultz et al. | |
| 2010/0261781 A1 | 10/2010 | Gmeiner | |
| 2010/0285052 A1 | 11/2010 | Mullis et al. | |
| 2011/0033846 A1 | 2/2011 | Dattagupta | |
| 2011/0046359 A1 | 2/2011 | Lee et al. | |
| 2011/0086780 A1 | 4/2011 | Colston, Jr. et al. | |
| 2011/0092381 A1 | 4/2011 | Sood et al. | |
| 2011/0136116 A1 | 6/2011 | Barany et al. | |
| 2012/0004132 A1 | 1/2012 | Zhang et al. | |
| 2012/0028242 A1 | 2/2012 | Heyduk et al. | |
| 2012/0178081 A1 | 7/2012 | Nguyen et al. | |
| 2012/0252682 A1 | 10/2012 | Zhou et al. | |
| 2012/0258880 A1 | 10/2012 | Schwartz et al. | |
| 2013/0059741 A1 | 3/2013 | Weiner | |
| 2013/0172213 A1 | 7/2013 | Oliphant et al. | |
| 2013/0225420 A1 | 8/2013 | Albertson et al. | |
| 2013/0323729 A1 | 12/2013 | Landegren et al. | |
| 2013/0330722 A1 | 12/2013 | Miller | |
| 2014/0030721 A1 | 1/2014 | Fredriksson et al. | |
| 2014/0080126 A1 | 3/2014 | Cantor et al. | |
| 2014/0194311 A1 | 7/2014 | Gullberg et al. | |
| 2015/0004598 A1 | 1/2015 | Gao et al. | |
| 2015/0005188 A1 | 1/2015 | Levner et al. | |
| 2015/0111788 A1 | 4/2015 | Fernandez et al. | |
| 2015/0148239 A1 | 5/2015 | Peter et al. | |
| 2015/0309028 A1 | 10/2015 | Jordan | |
| 2015/0368697 A1 | 12/2015 | Samusik et al. | |
| 2015/0376692 A1 | 12/2015 | Esfandyarpour et al. | |
| 2016/0009805 A1 | 1/2016 | Kowanetz et al. | |
| 2016/0115474 A1 | 4/2016 | Jelinek et al. | |
| 2016/0161472 A1 | 6/2016 | Jungmann et al. | |
| 2016/0169903 A1 | 6/2016 | Dai et al. | |
| 2016/0319328 A1 | 11/2016 | Yin et al. | |
| 2016/0346330 A1 | 12/2016 | Sussman et al. | |
| 2017/0009278 A1 | 1/2017 | Söderberg et al. | |
| 2017/0038391 A1 | 2/2017 | Lara Gutierrez et al. | |
| 2017/0137864 A1 | 5/2017 | Yin et al. | |
| 2017/0151569 A1 | 6/2017 | Handique et al. | |
| 2017/0349949 A1 | 12/2017 | Kolb | |
| 2018/0095067 A1 | 4/2018 | Huff et al. | |

FOREIGN PATENT DOCUMENTS

| | | |
|---|---|---|
| CN | 101680029 | 3/2010 |
| CN | 103429331 A | 12/2013 |
| CN | 103917654 A | 7/2014 |
| CN | 104114718 | 10/2014 |
| EP | 1270738 | 1/2003 |
| EP | 1851331 | 2/2016 |
| JP | 2004512057 A | 4/2004 |
| WO | WO 9950460 A1 | 10/1999 |
| WO | WO 01/97616 | 12/2001 |
| WO | WO 2005/054514 | 6/2005 |
| WO | WO 2006/137932 | 12/2006 |
| WO | WO2008/052774 | 5/2008 |
| WO | WO 2009/012220 | 1/2009 |
| WO | WO 2012/057689 | 5/2012 |
| WO | WO2012058638 | 5/2012 |
| WO | WO2012071428 | 5/2012 |
| WO | WO 2012134602 | 10/2012 |
| WO | WO 2012/152942 A1 | 11/2012 |
| WO | WO2013/113699 | 8/2013 |
| WO | WO 2013/188756 | 12/2013 |
| WO | WO 2014/200767 | 12/2014 |
| WO | WO2015017586 | 2/2015 |
| WO | WO 2015/052287 | 4/2015 |
| WO | WO2015138653 A1 | 9/2015 |
| WO | WO2015188839 | 12/2015 |
| WO | WO 2015200139 | 12/2015 |

OTHER PUBLICATIONS

Gou et al., "Laboratory diagnosis of blue ear disease", College of Animal Science and Technology, Northeast Agricultural University, Harbin Veken Biotechnology Development Company, 2011, 10: 83.

Boom D. et al., "Multiplex protein detection with DNA readout via mass spectrometry" N Biotechnol. (2013) 30(2):153-158.

Kazane S.A. et al., "Site-specfic DNA-antibody conjugates for specific and sensitive immuno-PCR" Procl Natl Acad Sci (2012) 109(10):3731-6.

Dhillon et al., "Homogeneous and digital proximity ligation assays for the detection of Clostridium difficile toxins A and B", Biomolecular Detection and Quantification, 2016, 10:2-8.

Shahi et al., "Abseq: Ultrahigh-throughput single cell protein profiling with droplet microfluidic barcoding", Scientific Reports, 2017, 7:44447, DOI: 10.1038/srep44447.

(56) References Cited

OTHER PUBLICATIONS

Zhang et al., "Protein quantification from complex protein mixtures using a proteomics methodology with single-cell resolution", PNAS, 2001, 98(10): 5497-5502.

Zhang et al., "A sensitive and high-throughput assay to detect low-abundance proteins in serum", Nature Medicine, 2006, 12(4): 473-477.

Lubeck et al., "Signle cell systems biology by super-resolution imaging and combinatorial labeling", Nat Methods., Jan. 1, 2013; 9(7): 743-748.

Byers et al., "Semiautomated Multiplexed Quantum Dot-Based in Situ Hybridization and Spectral Deconvolution", Journal of Molecular Diagnostics, 2007, 9(1): 20-29.

Chan et al., "Luminescent quantum dots for multiplexed biological detection and imaging", Current Opinion in Biotechnology, 2002, 13:40-46.

Englert et al., "Layered Expression Scanning: Rapid Molecular Profiling of Tumor Samples", Cancer Research, 2000, 60: 1526-1530.

Flor et al., "DNA-Directed Assembly of Antibody-Fluorophore Conjugates for Quantitative Multiparametric Flow Cytometry", Chembiochem, 2013, 15(2): 267-275.

Furuya et al., "A Novel Technology Allowing Immunohistochemical Staining of a Tissue Section with 50 Different Antibodies in a Single Experiment", Journal of Histochemistry & Cytochemistry, 2004, 52(2): 205-210.

Guo et al., "Multispectral labeling of antibodies with polyfluorophores on a DNA backbone and application in cellular imaging", PNAS, 2011, 108(9): 3493-3498.

Han et al., "An Approach to Multiplexing an Immunosorbent Assay with Antibody-Oligonucleotide Conjugates", Bioconjugate Chem., 2010, 21: 2190-2196.

Huang et al., "Comparison and Optimization of Multiplexed Quantum Dot-Based Immunohistofluorescence", Nano Res, 2010, 3: 61-68.

Larson et al., "Analytical Validation of a Highly Quantitative, Sensitive, Accurate, and Reproducible Assay (HERmark) for the Measurement of HER2 Total Protein and HER2 Homodimers in FFPE Breast Cancer Tumor Specimens", Pathology Research International, 2010, Article ID 814176, 14 pages.

Lundberg et al., "Homogeneous antibody-based proximity extension assays provide sensitive and specific detection of low-abundant proteins in human blood", Nucleic Acids Research, 2011, 39(15): e102.

Niemeyer et al., "Detecting antigens by quantitative immuno-PCR", Nature Protocols, 2007, 2(8): 1918-1930.

Saiki et al., "Analysis of enzymatically amplified β-globin and HLA-DQα DNA with allele-specific oligonucleotide probes", Nature, 1986, 324: 163-166.

Tran et al., "A Universal DNA-Based Protein Detection System", Journal of the American Chemical Society, 2013, 135(38): 14008-14011.

True et al., "Quantum Dots for Molecular Pathology", Journal of Molecular Diagnostics, 2007, 9(1): 7-11.

Ullal et al., "Cancer Cell Profiling by Barcoding Allows Multiplexed Protein Analysis in Fine-Needle Aspirates", Science Translational Medicine, 2014, 6(219): 219ra9.

Wahlby et al., "Sequential Immunofluorescence Staining and Image Analysis for Detection of Large Numbers of Antigens in Individual Cell Nuclei", Cytometry, 2002, 47:32-41.

Zrazhevskiy et al., "Quantum dot imaging platform for single-cell molecular profiling", Nat Commun. 2013 4: 1-12.

NCBI Accession No. M14144, Jan. 14, 1995, "Human vimentin gene, complete cds".

Gerdes et al., "Highly multiplexed single-cell analysis of formalin-fixed, paraffin-embedded cancer tissue", Proceedings of the National Academy of Sciences, 2013, 110(29):11982-11987.

Xiao et al., "Multiplexed single-cell in situ RNA analysis by reiterative hybridazation", Analytical Methods, 2015, 7(17):7290-7295.

Brucherseifer et al., "Label-free probing of the binding state of DNA by time-domain terahertz sensing", Applied Physics Letters, 2000, 77(24): 4049-4051.

Nagel et al., "Integrated THz technology for label-free genetic diagnostics", Applied Physics Letters, 2002, 80(1): 154-156.

Kozlov et al., Efficient Strategies for the Conjugation of Oligonucleotides to Antibodies Enabling Highly Sensitive Protein Detection. Biopolymers. 2004; 73(5): 621-630.

* cited by examiner

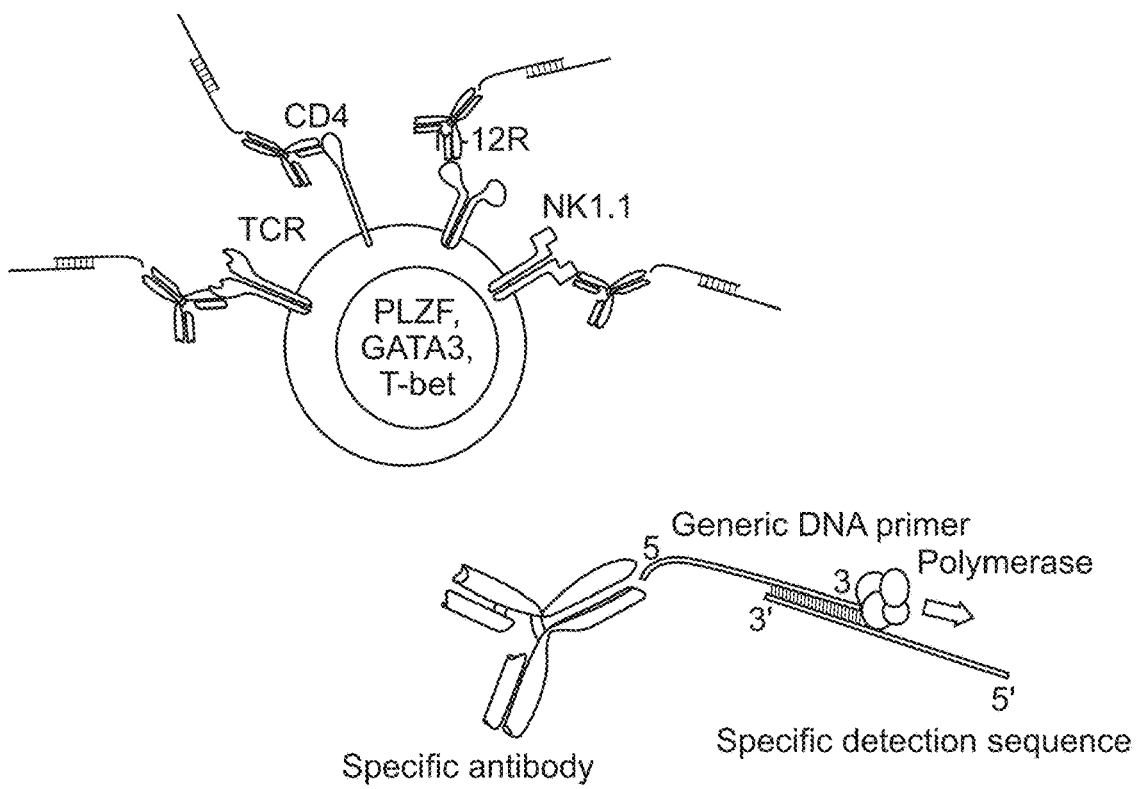
FIG. 1A
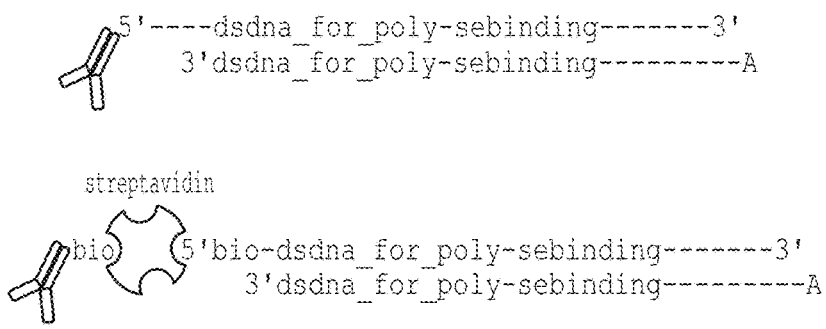
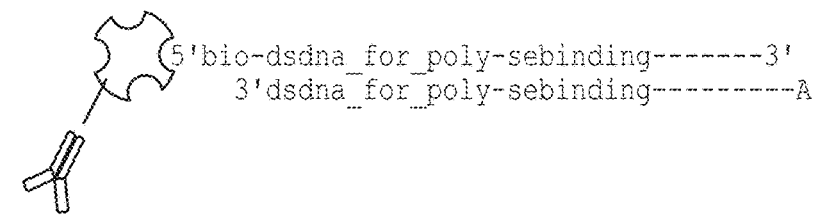
FIG. 1B

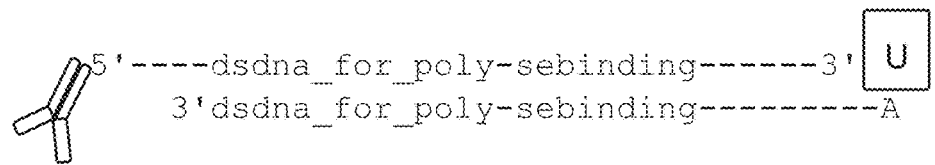
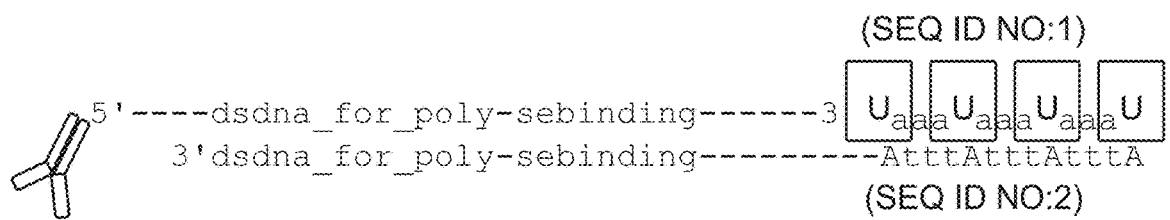
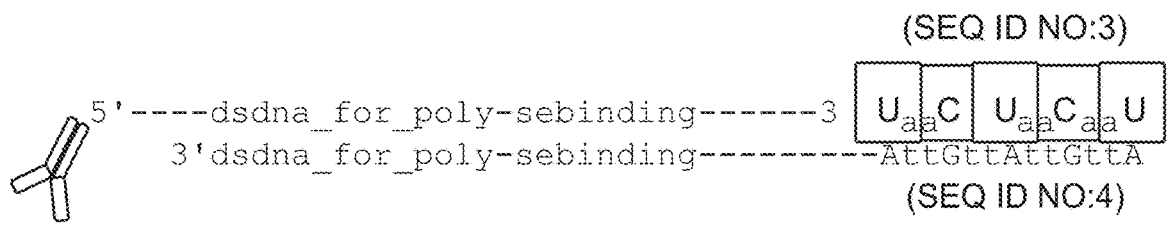
FIG. 2

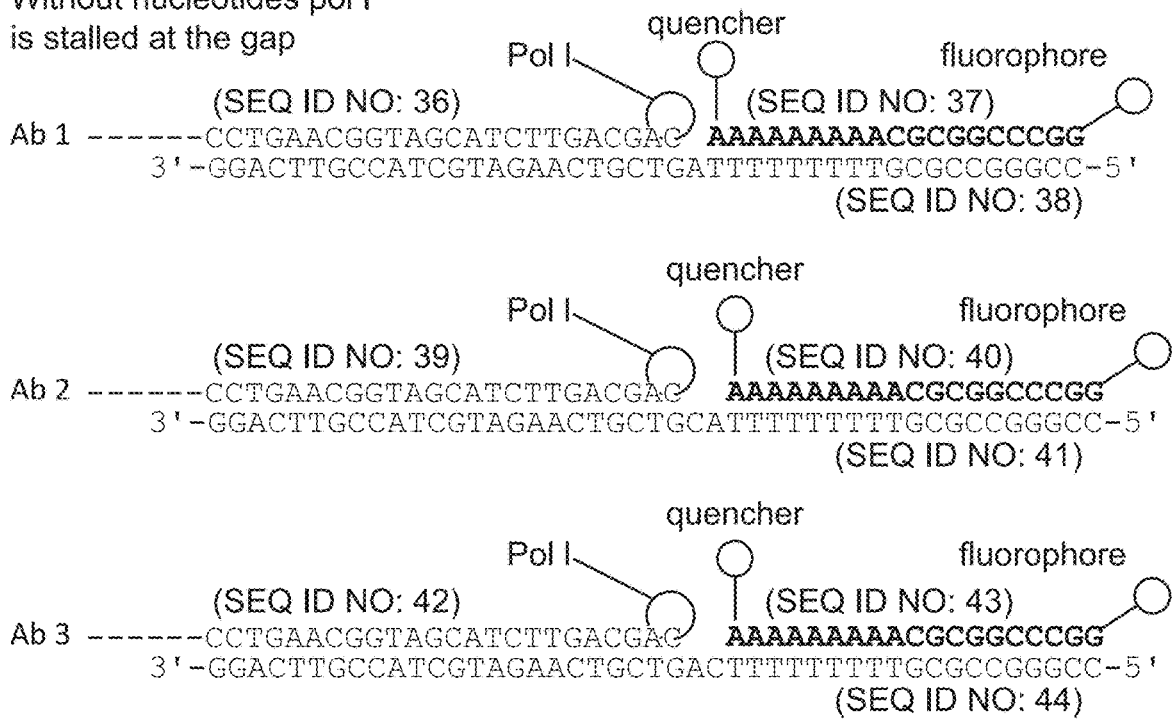
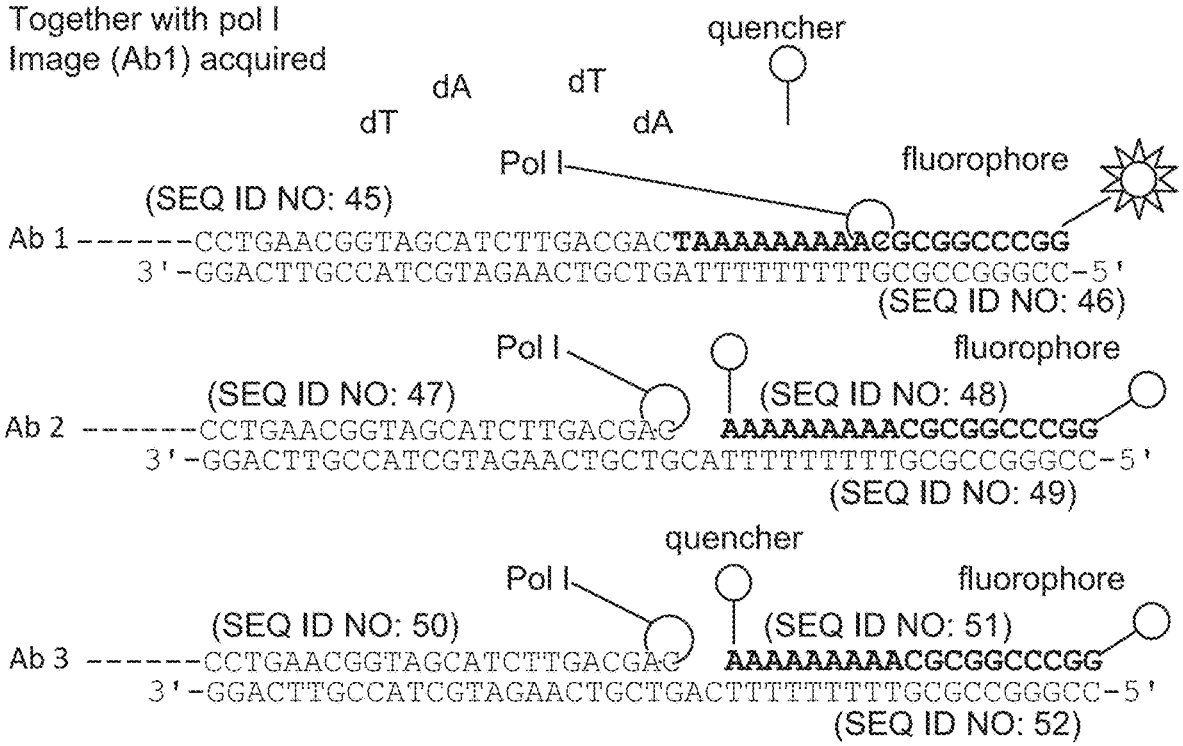
FIG. 8

STEP3
dC and dG are supplied
together with pol I
Fluorophor on Ab1 is
removed

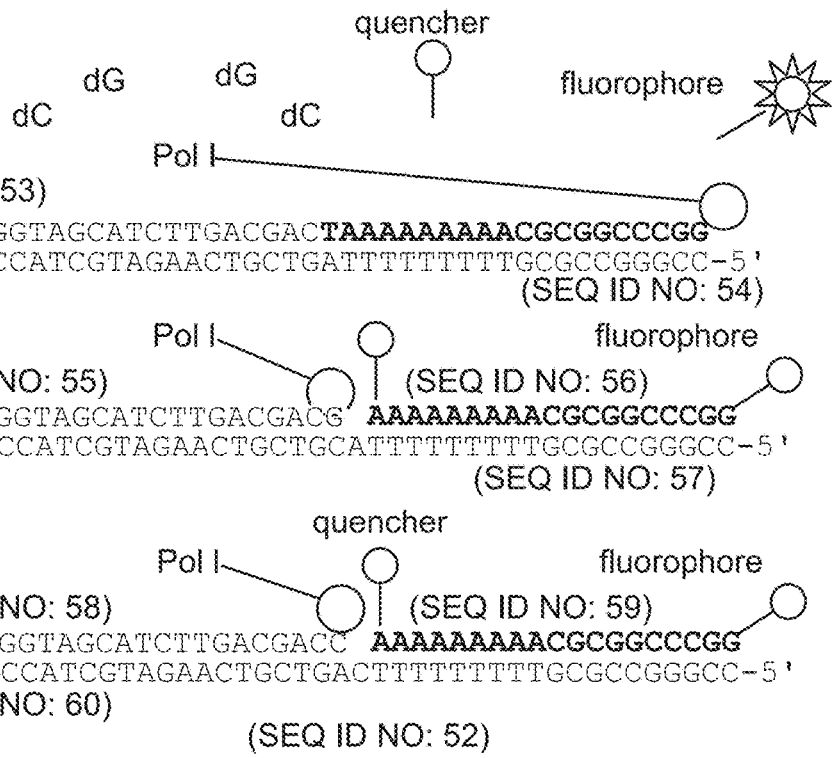

Ab 1 ------CCTGAACGGTAGCATCTTGACGACTAAAAAAAAAACGCGGCCGG
         3'-GGACTTGCCATCGTAGAACTGCTGATTTTTTTTTGCGCCGGGCC-5'
              (SEQ ID NO: 53)                        (SEQ ID NO: 54)

Ab 2 ------CCTGAACGGTAGCATCTTGACGACG AAAAAAAAACGCGGCCGG
         3'-GGACTTGCCATCGTAGAACTGCTGCATTTTTTTTGCGCCGGGCC-5'
              (SEQ ID NO: 55)   (SEQ ID NO: 56)
                                                     (SEQ ID NO: 57)

Ab 3 ------CCTGAACGGTAGCATCTTGACGACC AAAAAAAAACGCGGCCGG
         3'-GGACTTGCCATCGTAGAACTGCTGACTTTTTTTTGCGCCGGGCC-5'
              (SEQ ID NO: 58)   (SEQ ID NO: 59)
              (SEQ ID NO: 60)   (SEQ ID NO: 52)

STEP4
dT and dA are supplied
together with pol I
Image (Ab2) acquired

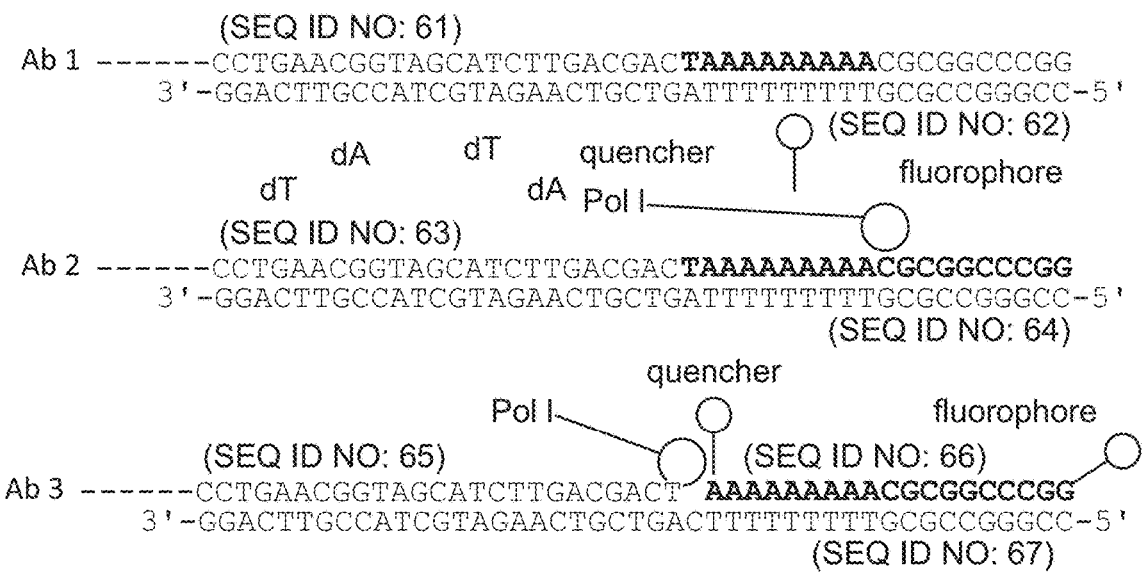

Ab 1 ------CCTGAACGGTAGCATCTTGACGACTAAAAAAAAACGCGGCCGG
         3'-GGACTTGCCATCGTAGAACTGCTGATTTTTTTTTGCGCCGGGCC-5'
              (SEQ ID NO: 61)                (SEQ ID NO: 62)

Ab 2 ------CCTGAACGGTAGCATCTTGACGACTAAAAAAAAAACGCGGCCGG
         3'-GGACTTGCCATCGTAGAACTGCTGATTTTTTTTTGCGCCGGGCC-5'
              (SEQ ID NO: 63)                (SEQ ID NO: 64)

Ab 3 ------CCTGAACGGTAGCATCTTGACGACT AAAAAAAAACGCGGCCGG
         3'-GGACTTGCCATCGTAGAACTGCTGACTTTTTTTTGCGCCGGGCC-5'
              (SEQ ID NO: 65)   (SEQ ID NO: 66)
                                                     (SEQ ID NO: 67)

FIG. 8 (Cont.)

```
                                                          (SEQ ID NO: 68)
Ab1-3'-GAACCGGTGAGTGGGATCGTGACCGAGCGAGATA

⇩

(SEQ ID NO: 69)
Ab1-3'-GAACCGGTGAGTGGGATCGTGACCGAGCGAGATA
                     5'-GCACTGGCTCGCTCTA
                        (SEQ ID NO: 70)

⇩

(SEQ ID NO: 71)
Ab1-3'-GAACCGGTGAGTGGGATCGTGACCGAGCGAGATA
                     5'-GCACTGGCTCGCTCTAU ── (Cy5)
                        (SEQ ID NO: 72)

⇩

(SEQ ID NO: 73)
Ab1-3'-GAACCGGTGAGTGGGATCGTGACCGAGCGAGATA
                     5'-GCACTGGC  (3-5 exo)
                        (SEQ ID NO: 74)
```

FIG. 9A

```
                                                          (SEQ ID NO: 75)
Ab1-3'-GAACCGGTGAGTGGGATCGTGACCGAGCGAGATAC
                     5'-GCACTGGCTCGCTCTAU ── (Cy5)
                        (SEQ ID NO: 76)

(SEQ ID NO: 77)
Ab2-3'-GAACCGGTGAGTGGGATCGTGACCGGACCTGTAAC
                     5'-GCACTGGCTCGCTCTA
                        (SEQ ID NO: 78)

(SEQ ID NO: 79)
Ab3-3'-GAACCGGTGAGTGGGATCGTGACCAGTGACTGAAC
                     5'-GCACTGGCTCGCTCTA
                        (SEQ ID NO: 80)
```

FIG. 9B (SEQ ID NO: 87)
GAACCGGTGAGTGGGATAGCGCTACGCCTGAACGGTAGCATCTTGACGAC
　　　　　　　　　　　　　　　　　　　　　　　　　　　　　　　　ZGGACTTGCCATCGTAGAACTGCGTTTTT
(SEQ ID NO: 88)

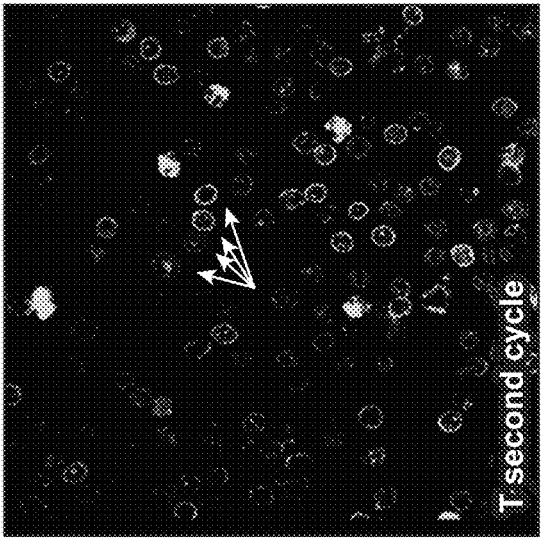
FIG. 13B
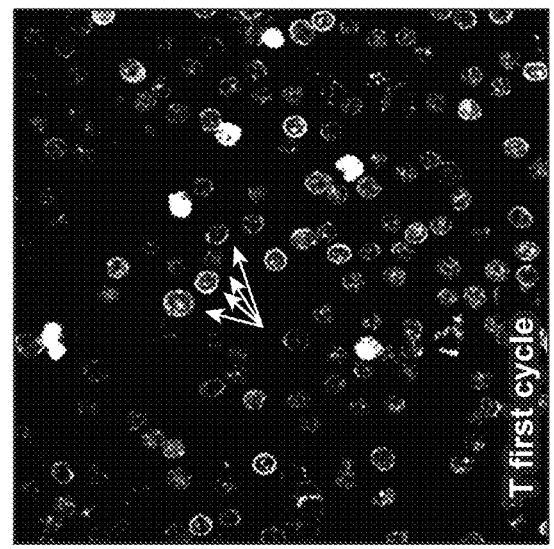
FIG. 13D
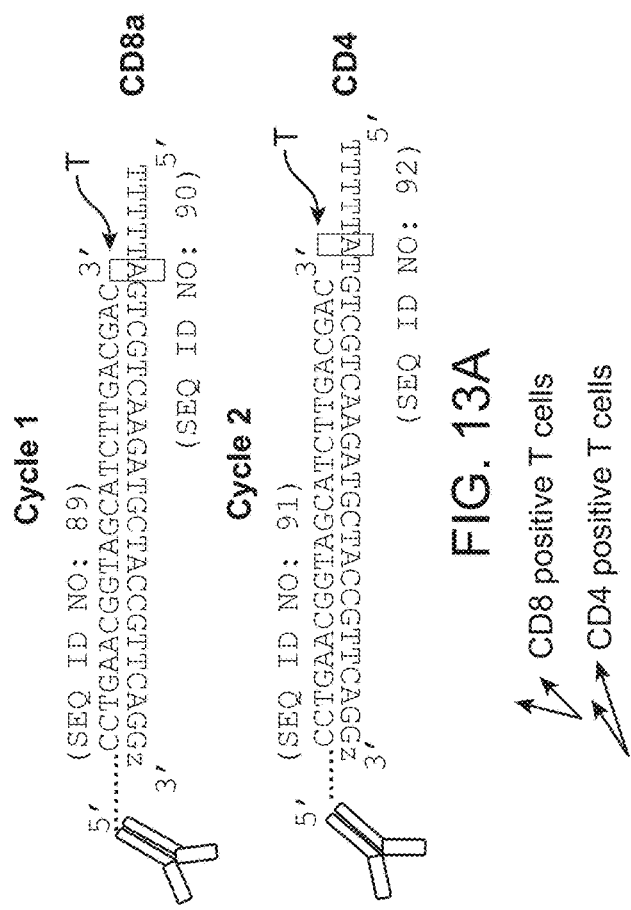
FIG. 13A
FIG. 13C

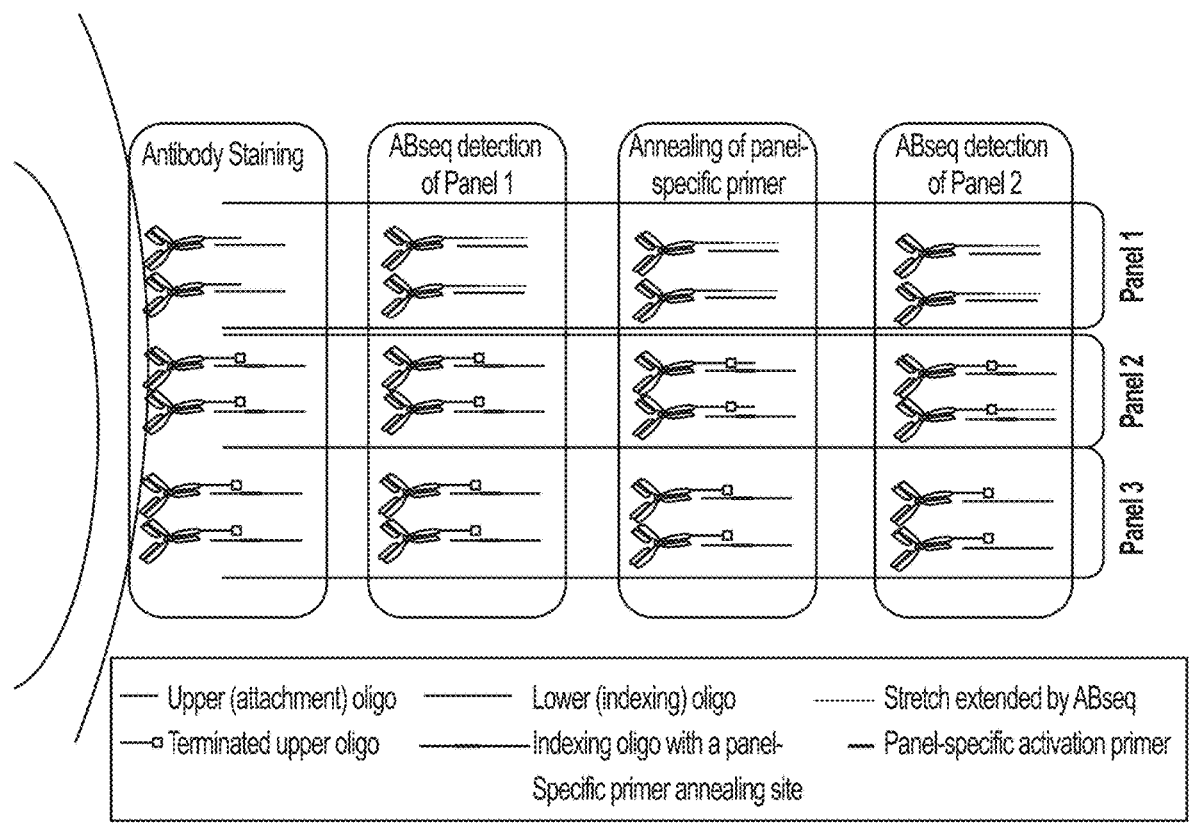
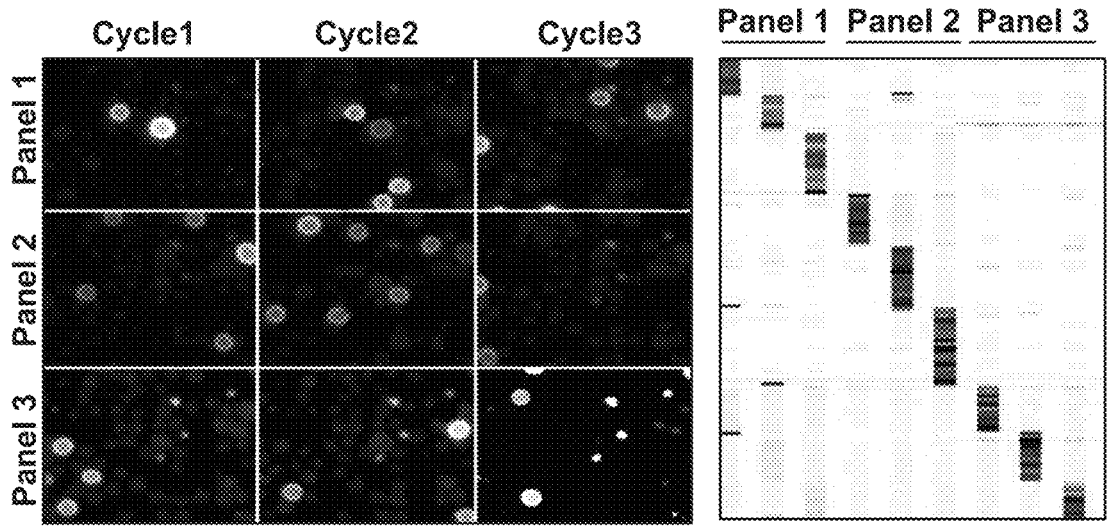
FIG. 18

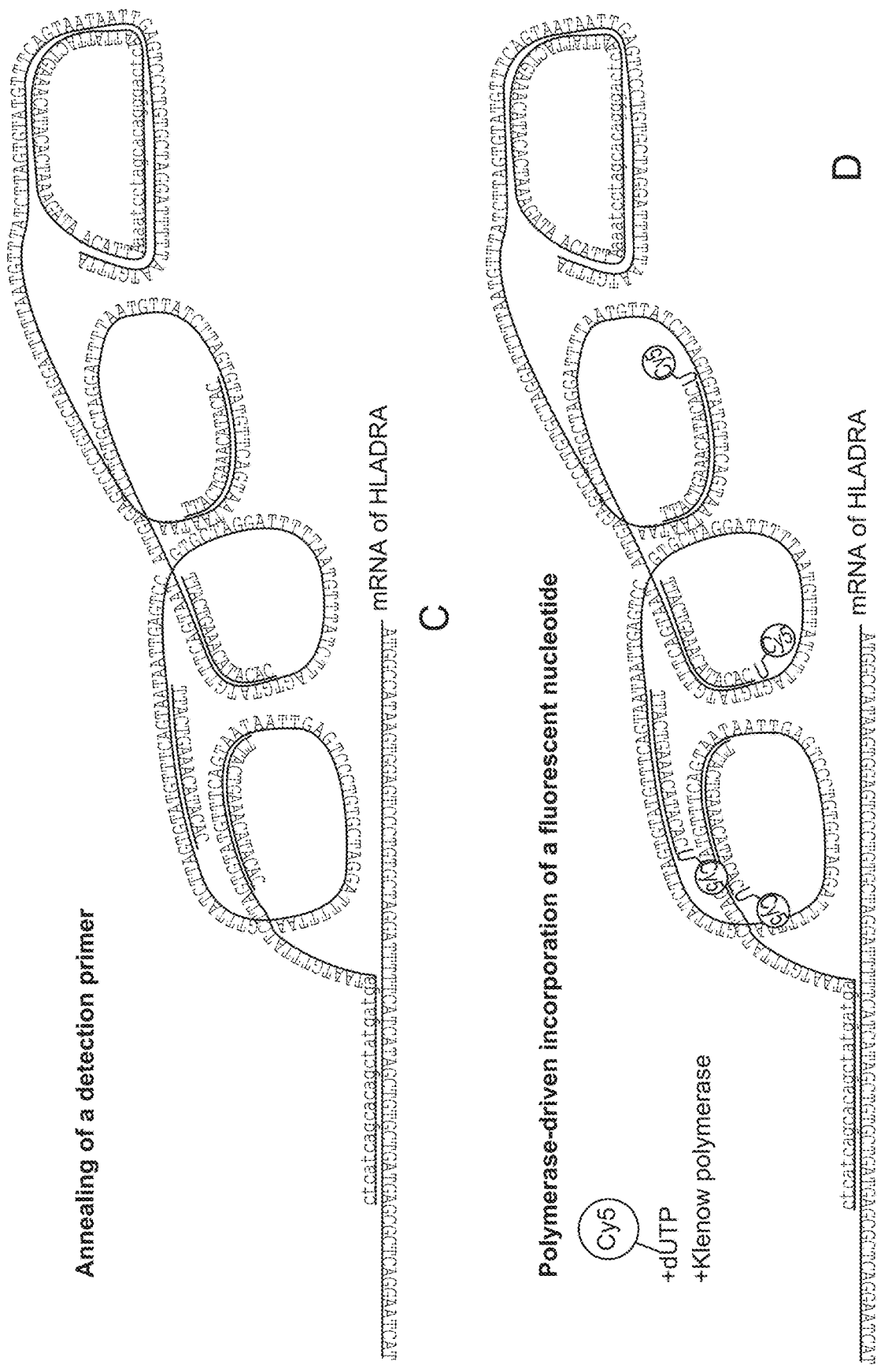
FIG. 19 (Cont. 1)

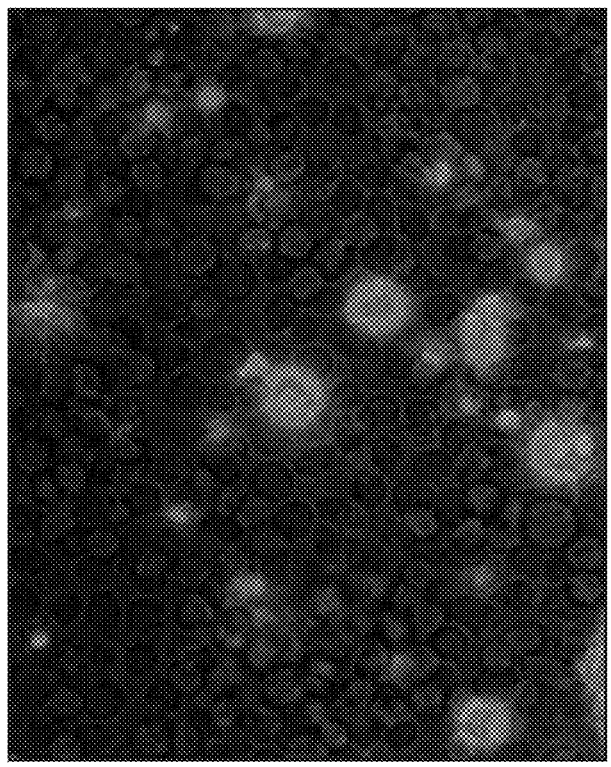
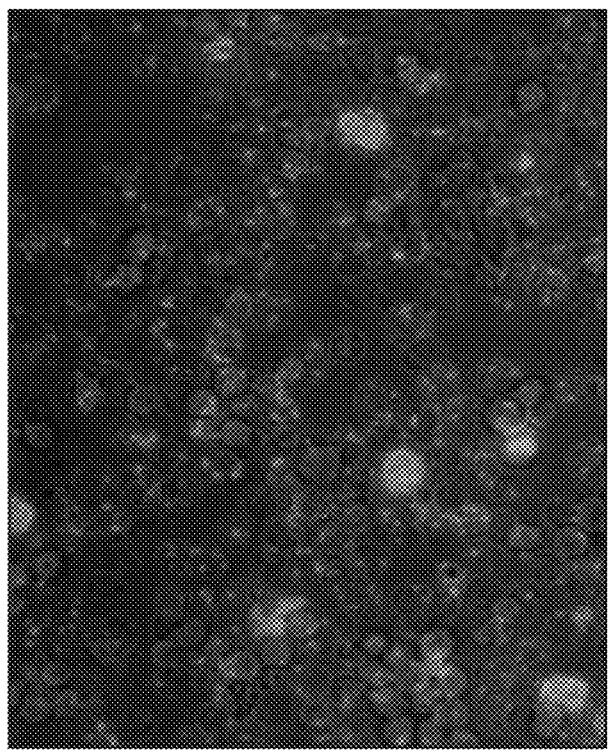
F
E
FIG. 19 (Cont. 2)

ON-SLIDE STAINING BY PRIMER EXTENSION

CROSS-REFERENCING

This patent application is a continuation of U.S. application Ser. No. 16/679,769, filed on Nov. 11, 2019, which is a continuation of U.S. application Ser. No. 15/317,019, filed on Dec. 7, 2016, which a § 371 filing of PCT application serial no. PCT/US2015/036763, filed on Jun. 19, 2015, which claims the benefit of U.S. provisional application Ser. No. 62/015,799, filed Jun. 23, 2014, and PCT/US2015/036763 is a continuation-in-part of U.S. non-provisional application Ser. No. 14/560,921, filed on Dec. 4, 2014, which patent applications are incorporated by reference herein in their entireties.

STATEMENT REGARDING FEDERALLY SPONSORED RESEARCH

This invention was made with Government support under contract W81XWH-12-1-0591 awarded by the Department of Defense and under contracts GM104148 and HHSN268201000034C awarded by the National Institutes of Health. The Government has certain rights in the invention.

BACKGROUND

Several major approaches have been used so far for single-cell antigen cytometry. Among the most popular are single cell PCR, fluorescence activated flow cytometry, mass cytometry and single cell sequencing. These (fluorescence and mass-based cytometry) approaches are limited from either inability to breach the multiplexing levels of more than 100 parameters per analyte (cell in this case) or from inability to achieve high throughput (single cell sequencing). Also these methods are not appropriate or readily modified to enable cell multiplexed analysis of archived tissues and slide based samples.

Disclosed herein are several related methods for capture agent detection that are based on labeling the capture agent with DNA and subsequent detection of this DNA by primer extension.

SUMMARY

A method for analyzing a planar sample is provided. In certain embodiments, the method may comprise: (a) labeling the planar sample (e.g., a tissue section) with a capture agent (e.g., an antibody or an oligonucleotide probe) in a way that produces a labeled sample in which: (i) the capture agent is linked to a double-stranded nucleic acid that comprises a first strand and a second strand; and (ii) the 3' end or 5' end of either the first strand or the second strand is extendible using the other strand as a template; (b) contacting the labeled sample with i. a polymerase and a nucleotide mix and/or ii. a labeled oligonucleotide and a ligase, thereby adding one or more nucleotides and/or a labeled oligonucleotide to an one of the strands of the double-stranded nucleic acid; and (c) reading a fluorescent signal generated by addition of the one or more nucleotides and/or oligonucleotide to one of the strands of the double-stranded nucleic acid using fluorescence microscopy, thereby producing an image showing the pattern of binding of the capture agent to the planar sample.

The method may be implemented in a variety of different ways. For example, in some embodiments, step (b) may contacting the labeled sample with a polymerase and a nucleotide mix that comprises a fluorescent nucleotide, thereby adding the fluorescent nucleotide to one of the strands (i.e., the top strand or the bottom strand, whichever strand has the extendible 3' end) of the double-stranded nucleic acid; and step (c) may comprise reading a fluorescent signal generated by addition of the fluorescent nucleotide to one of the strands (i.e., the top strand or the bottom strand, whichever strand has the extendible 3' end) of the double-stranded nucleic acid. In this embodiment, the fluorescent signal may: i. emitted directly from the added nucleotide; ii. a FRET signal generated by energy transfer between two fluorescent nucleotides that are added to a 3' end of one of the strands; or iii. a FRET signal generated by energy transfer between a first added fluorescent nucleotide (i.e., a fluorescent nucleotide that has been added to one of the strands) and a second fluorescent nucleotide that is already present in one of the strands.

In alternative embodiments, step (b) comprises contacting the labeled sample with a ligase and a labeled oligonucleotide, thereby adding the labeled oligonucleotide to the 3' or 5' end of one of the strands of the double-stranded nucleic acid; and step (c) comprises reading a fluorescent signal generated by ligation of the labeled oligonucleotide to one of the strands of the double-stranded nucleic acid. In some cases, an extendible 3' end may be extended by a polymerase, and ligated to a labeled oligonucleotide. In these embodiments, the fluorescent signal may be: i. emitted directly from the added nucleotide; ii. a FRET signal generated by energy transfer between two fluorescent nucleotides that are added to one of the strands; or iii. a FRET signal generated by energy transfer between a first fluorescent nucleotide added one of the strands and a second fluorescent nucleotide that is already present in the other strand.

In some embodiments, extension of one of the strands removes a quencher from a quenched fluorescently labeled oligonucleotide that is hybridized to the other strand, downstream from the first strand.

In some embodiments, the first strand is a rolling circle amplification (RCA) product, and the second strand comprises oligonucleotides that are hybridized to multiple sites in the RCA product.

In other embodiments, the first strand is an oligonucleotide, and the second strand is a second oligonucleotide that is hybridized to the first oligonucleotide. In these embodiments, the oligonucleotides may be designed to produce a 5' overhang such that the 3' end of the first strand oligonucleotide is extendible using the other oligonucleotide as a template. In other embodiments, the oligonucleotides may be designed to produce a 3' overhang such that the 5' end of the first strand oligonucleotide is extendible by ligation, using the other oligonucleotide as a template In any embodiment, the planar sample may be a tissue section, e.g., a formalin-fixed, paraffin-embedded (FFPE) tissue section.

Also provided herein is a capture agent that is linked to a double-stranded nucleic acid, wherein: (i) the double-stranded nucleic acid comprises a first strand and a second strand; (ii) the capture agent is linked to the first strand; and (iii) the 3' end or 5' end of either the first strand or the second strand is extendible using the other strand as a template.

Also provided herein is a capture agent composition comprising a plurality of capture agents that recognize different complementary sites, wherein: each of the capture agents is linked to a double-stranded nucleic acid that comprises a first strand and a second strand; the capture agents are linked to a double-stranded nucleic acid by the first strand; the 3' end or 5' end of the first or second strand is extendible using the other strand as a template; and the templates immediately downstream of the extendible ends are different for each of the capture agents. In these embodiments, the sequence of the first strand is the same for each of the capture agents; and the sequence of the second strand is different for each of the capture agents.

In embodiments that use a reversible terminator ("reversible terminator" approach), the templates immediately adjacent to the template at the extendible 3' end may be of the formula 3'-$N_{4n}N_1/N_2/N_3$-5' optionally followed by short stretch (e.g., 1-5 residues) of random nucleotides on the 5' end to increase the overall polymerase residence on the DNA duplex, where $N_1$, $N_2$, $N_3$ and $N_4$ are different nucleotides selected from G, A, T and C and n is 0, 1 or more. In some cases, the population contains single nucleotide overhangs of nucleotides $N_1$, $N_2$ and $N_3$ or the population of overhangs comprises two nucleotide overhangs of sequence 3'-$N_4N_1$-5', 3'-3'-$N_4N_2$-5' and 3'-$N_4N_3$-5'-5' and, optionally overhangs of sequence, 3'-$N_4N_4N_1$-5', 3'-$N_4N_4N_2$-5' and 3'-$N_4N_4N_3$-5' and so on (e.g., four nucleotide overhangs of sequence 3'-$N_4N_4N_4N_1$-5', 3'-$N_4N_4N_4N_2$-5' and 3'-$N_4N_4N_4N_3$-5'). A population of oligonucleotides or RCA products having sequences that are defined by any of these formulas is also provided. In RCA embodiments, the sequence may be found in each repeat of an RCA product.

In these embodiments, the templates immediately adjacent to the extendible 3' end may be of a more general formula 3'-$XN_1/N_2/N_2$-5', where $N_1$, $N_2$, $N_3$ are different nucleotides selected from G, A, T and C and X is a nucleotide stretch of bases Xi (such that Xi are different nucleotides selected from G, A, T and C) of random composition and length. In some cases, the population may comprise comprises two nucleotide overhangs of sequence 3'-$X_1N_1$-5', 3'-$X_1N_2$-5' and 3'-$X_1N_3$-5' and, optionally overhangs of sequence, 3'-$N_1X_1X_2$-5', 3'-$N_2X_1X_2$-5' and 3'-$N_3X_1X_2$-5' and so on (e.g., four nucleotide overhangs of sequence 3'-$N_1X_1X_2X_3$-5', 3'-$N_2X_1X_2X_3$-5' and 3'-$N_3X_1X_2X_3$-5'). In many embodiments, this population additionally contains single nucleotide overhangs of nucleotides $N_1$, $N_2$ and $N_3$. A population of oligonucleotides or RCA products having sequences that are defined by any of these formulas is also provided. In RCA embodiments, the sequence may be found in each repeat of an RCA product.

In embodiments that rely on a "missing base" approach, the template immediately adjacent to the extendible 3' end may be of the formula 3'-$YN_1/N_2$-5', optionally followed by short stretch (e.g., 1-5 residues) of random nucleotides on the 5' end to increase the overall polymerase residence on the DNA duplex, wherein Y is a nucleotide sequence of length n (n is 0, 1 or more) composed of bases $N_3$ and $N_4$, wherein nucleotide $N_3$ is in odd positions and nucleotide $N_4$ is in even positions, counting from the start of the overhang and $N_1$, $N_2$, $N_3$ and $N_4$ are different nucleotides selected from G, A, T and C. For example, in some cases, the population may comprise 5' overhangs of sequence 3'-$N_1$-5' and 3'-$N_2$-5' or optionally 3'-$N_3N_1$-5' and 3'-$N_3N_2$-5' or 3'-$N_3N_4N_1$-5' and 3'-$N_3N_4N_2$-5' and, optionally, overhangs of sequence 3'-$N_3N_4N_3N_1$-5' and 3'-$N_3N_4N_3N_2$-5' and so on (e.g., overhangs of sequence 3'-$N_3N_4N_3N_4N_1$-5' and 3'-$N_3N_4N_3N_4N_2$-5' and then 3'-$N_3N_4N_3N_4N_3N_1$-5' and 3'-$N_3N_4N_3N_4N_3N_2$-5'). A population of oligonucleotides or RCA products having sequences that are defined by any of these formulas is also provided. In RCA embodiments, the sequence may be found in each repeat of an RCA product.

In these embodiments the template immediately adjacent to the extendible 3' end may also be of a more general formula 3'-$YN_1/N_2$-5', wherein Y is a nucleotide sequence of length n (n is 0, 1 or more) composed of alternating random length stretches of bases $N_3$ and $N_4$ such that the order number of $N_3$—stretches is odd and of $N_4$ stretches is even and wherein $N_1$, $N_2$, $N_3$ and $N_4$ are different nucleotides selected from G, A, T and C. For example, the population may comprise overhangs of sequence 3'-$N_1$-5' and 3'-$N_2$-5' or optionally 3'-$N_3N_3N_1$-5' and 3'-$N_3N_3N_2$-5' or 3'-$N_3N_3N_4N_1$-5' and 3'-$N_3N_3N_4N_2$-5' and, optionally, overhangs of sequence 3'-$N_3N_3N_3N_3N_4N_4N_3N_3N_1$-5' and 3'-$N_3N_3N_3N_3N_4N_4N_3N_3N_1$-5' and so on). A population of oligonucleotides or RCA products having sequences that are defined by any of these formulas is also provided. In RCA embodiments, the sequence may be found in each repeat of an RCA product.

A method for analyzing a tissue sample is also provided. In these embodiments, the method may comprise (a) labeling a planar sample with the above-described capture agent composition; (b) contacting the labeled sample with i. a polymerase and either an incomplete nucleotide mix or a nucleotide mix that comprises a reversible terminator nucleotide and/or ii. a labeled oligonucleotide and a ligase; and (c) reading, using fluorescence microscopy, a fluorescent signal generated by addition a nucleotide or a labeled oligonucleotide to some but not all of the capture agents.

In these embodiments, the method may comprises: (c) contacting the planar sample with a polymerase and: (i) a nucleotide mix that comprises fluorescent nucleotides that are complementary to $N_1$, $N_2$ and $N_3$ and a reversible terminator nucleotide that is complementary to $N_4$ or (ii) a nucleotide mix that comprises fluorescent nucleotides that are complementary to $N_1$, and $N_2$, an unlabeled nucleotide that is complementary to $N_3$, and no nucleotide that is complementary to $N_4$, thereby adding fluorescent nucleotides onto the double-stranded nucleic acids of some but not all of the capture agents; and (d) reading, using fluorescence microscopy, a fluorescent signal generated by addition of a fluorescent nucleotide to some but not all of the capture agents.

In some embodiments, the templates immediately adjacent to the extendible 3' end are of the formula 3'-$N_{4n}N_1/N_2/N_3$, wherein $N_1$, $N_2$, $N_3$ and $N_4$ are different nucleotides selected from G, A, T and C and n is 1 or more; and step (c) comprises contacting the planar sample with a polymerase and a nucleotide mix that comprises fluorescent nucleotides that are complementary to $N_1$, $N_2$ and $N_3$ and a reversible terminator nucleotide that is complementary to $N_4$.

In some embodiments, this method may further comprise: (e) inactivating the fluorescent signal, deprotecting the reversible terminator nucleotide and blocking the sample; and (f) repeating steps (c) and (d). In some cases, step (f) may comprise repeating steps (c), (d) and (e) multiple times.

In some embodiments, the templates immediately adjacent to the extendible 3' end may be of the formula 3'-$YN_1/N_2$-5', optionally followed by short stretch (e.g., 1-5 nucleotides) of random nucleotides on the 5' end to increase the overall polymerase residence on the DNA duplex, wherein Y is composed of alternating stretches of bases $N_3$ and $N_4$, and wherein $N_1$, $N_2$, $N_3$ and $N_4$ are different nucleotides selected from G, A, T and C.

In these embodiments, the method may comprise (e) inactivating the fluorescent signal and contacting the planar sample with a polymerase and a an unlabeled nucleotide that is complementary to $N_4$; and (f) repeating steps (c) and (d). In certain cases, step (f) may comprise repeating steps (c), (d) and (e) multiple times.

In alternative embodiments, the double-stranded oligonucleotides may each comprise a fluorescently labeled oligonucleotide hybridized to the second strand downstream from first strand, wherein the fluorescently labeled oligonucleotide comprises a quencher and extension of the first strand removes the quencher from some but not all of the quenched fluorescently labeled oligonucleotides, thereby generating a fluorescent signal for some but not all of the capture agents.

In other embodiments, the capture agent is linked to a single stranded oligonucleotide, which can be either unlabeled or labeled with FRET acceptor fluorophore. Such a single stranded nucleotide incorporates a dedicated sequence that hybridizes to a complementary oligonucleotide which is to be extended with unlabeled base or with a base labeled with a FRET excitation fluorophore, thereby generating a fluorescent signal for some but not all of the capture agents.

In some embodiments, a method for analyzing a planar sample. In some embodiments, the method comprises: (a) labeling the planar sample with a capture agent to produce a labeled sample, wherein: (i) the capture agent is linked to a double-stranded nucleic acid that comprises a first strand and a second strand; and (ii) a 3' end or 5' end of either the first strand or the second strand is extendible using the other strand as a template; (b) contacting the labeled sample with i. a polymerase and a plurality of nucleotides and/or ii. a labeled oligonucleotide and a ligase, thereby adding one or more nucleotides of the plurality of nucleotides and/or a labeled oligonucleotide to an end of one of the strands of the double-stranded nucleic acid; and (c) reading a signal generated by addition of the one or more nucleotides and/or labeled oligonucleotide to one of the first strand or the second strand of the double-stranded nucleic acid. In some embodiments, the signal may be a fluorescent signal. In some embodiments, the reading may comprises fluorescence microscopy. Any embodiment, the method may further comprise producing an image showing the pattern of binding of the capture agent to the planar sample.

In any embodiment, step (b) may comprise contacting the labeled sample with a polymerase and a plurality of nucleotides that comprises a fluorescent nucleotide, thereby adding the fluorescent nucleotide to one of the first strand or the second strand of the double-stranded nucleic acid; and step (c) comprises reading a fluorescent signal generated by addition of the fluorescent nucleotide to one of the first strand or the second strand of the double-stranded nucleic acid. In these embodiment, wherein the fluorescent signal may be: i. emitted directly from the added nucleotide; ii. a FRET signal generated by energy transfer between two fluorescent nucleotides of the plurality of fluorescent nucleotides that are added to one of the first strand or second strand of the double-stranded nucleic acid; or iii. a FRET signal generated by energy transfer between the added fluorescent nucleotide and a second fluorescent nucleotide that is present in one of the first strand or second strand double-stranded nucleic acid.

In any embodiment, the method step (b) may comprise contacting the labeled sample with a ligase and a labeled oligonucleotide, thereby adding the labeled oligonucleotide to one of the first strand or second strand of the double-stranded nucleic acid; and step (c) comprises reading a fluorescent signal generated by addition of the labeled oligonucleotide to one of the first strand or second strand of the double-stranded nucleic acid. In this embodiment, the fluorescent signal may be: i. emitted directly from the added labeled nucleotide; ii. a FRET signal generated by energy transfer between two labeled nucleotides that are added to one of the first strand or second strand of the double-stranded nucleic acid; or iii. a FRET signal generated by energy transfer between the labeled nucleotide added to one of the first strand and second strand of the double-stranded nucleic acid and a second labeled nucleotide that is present in the other strand. In these embodiments, the labeled nucleotide may comprise a fluorescent nucleotide.

In any embodiment, extension of one of the first strand or second strand of the double-stranded nucleic acid may remove a quencher from a quenched fluorescently labeled oligonucleotide that is hybridized to the other strand, downstream from the first strand.

In any embodiment, the first strand of the double-stranded nucleic acid may be a rolling circle amplification (RCA) product, and the second strand of the double-stranded nucleic acid comprises oligonucleotides that are hybridized to multiple sites in the RCA product.

In any embodiment, the first strand of the double-stranded nucleic acid may be a first oligonucleotide, and the second strand of the double-stranded nucleic acid is a second oligonucleotide that is hybridized to the first oligonucleotide.

In any embodiment, the planar sample may be a formalin-fixed, paraffin-embedded (FFPE) section.

In any embodiment, the capture agent may be an antibody, an aptamer, or an oligonucleotide probe.

A capture agent that is linked to a double-stranded nucleic acid is also provided. In some embodiments, (i) the double-stranded nucleic acid comprises a first strand and a second strand; (ii) the capture agent is linked to the first strand; and (iii) the 5' end or the 3' end of either the first strand or the second strand is extendible using the other strand as a template.

Also provided is a capture agent composition comprising a plurality of capture agents that each recognize different complementary sites. In these embodiments, each of the plurality of capture agents may be linked to a double-stranded nucleic acid that comprises a first strand and a second strand; the 5' end or 3' end of the first or second strand may be extendible using the other strand as a template; and the templates immediately downstream of the extendible ends may be different for each of the plurality of capture agents. In these embodiments, the sequence of the first strand may be the same for each of the plurality of capture agents; and the sequence of the second strand may be different for each of the plurality of capture agents.

In some embodiments, the templates immediately adjacent to the extendible 3' ends may be of the formula 3'-$N_{4n}N_1/N_2/N_3$, wherein $N_1$, $N_2$, $N_3$ and $N_4$ are different nucleotides selected from G, A, T and C and n is 1 or more.

In some embodiments, the templates immediately adjacent to the extendible 3' ends may be of the formula 3'-$YN_1/N_2$-5', optionally followed by a short stretch of random nucleotides on the 5' end to increase the overall polymerase residence on the DNA duplex, wherein Y is composed of alternating stretches of $N_3$ and $N_4$, and wherein $N_1$, $N_2$, $N_3$ and $N_4$ are different nucleotides selected from G, A, T and C.

A method for analyzing a planar sample is provided. This method may comprise (a) labeling the planar sample with a capture agent composition summarized above; (b) contacting the labeled sample with i. a polymerase and either an incomplete nucleotide mix or a nucleotide mix that comprises a reversible terminator nucleotide, thereby adding a nucleotide to the plurality of capture agents; and/or ii. a labeled oligonucleotide and a ligase, thereby adding a labeled oligonucleotide to the plurality of capture agents; and (c) reading a signal generated by addition of the nucleotide or the labeled oligonucleotide to some but not all of the plurality of capture agents. In these embodiments, the signal may be a fluorescent signal. In some embodiments, the reading may be done by fluorescent microscopy.

In some embodiments, the method may be done by (b) contacting the planar sample with a polymerase and: (i) a nucleotide mix that comprises a plurality of fluorescent nucleotides that are complementary to $N_1$, $N_2$ and $N_3$ and a reversible terminator nucleotide that is complementary to $N_4$; or (ii) a nucleotide mix that comprises a plurality of fluorescent nucleotides that are complementary to $N_1$, and $N_2$, an unlabeled nucleotide that is complementary to $N_3$, and no nucleotide that is complementary to $N_4$, thereby adding fluorescent nucleotides onto the double-stranded nucleic acids of some but not all of the plurality of capture agents; and (c) reading, using fluorescence microscopy, a fluorescent signal generated by addition of the fluorescent nucleotides to the double-stranded nucleic acids of some but not all of the plurality of capture agents. In these embodiments, the templates immediately adjacent to the extendible 3' end may be of the formula 3'-$N_{4n}N_1/N_2/N_3$, wherein $N_1$, $N_2$, $N_3$ and $N_4$ are different nucleotides selected from G, A, T and C and n is 1 or more; and step (b) comprises contacting the planar sample with a polymerase and a nucleotide mix that comprises a plurality of fluorescent nucleotides that are complementary to $N_1$, $N_2$ and $N_3$ and a reversible terminator nucleotide that is complementary to $N_4$. In these embodiments, the method may further comprise: (d) inactivating the fluorescent signal, (e) optionally, deprotecting the reversible terminator nucleotide; (f) blocking the sample; and (g) repeating steps (b) and (c). In some embodiment, step (g) may comprise repeating steps (b)-(f) multiple times.

In some embodiments, the templates immediately adjacent to the extendible 3' end may be of the formula 3'-$YN_1$/$N_2$-5', optionally followed by a short stretch of random nucleotides on the 5' end to increase the overall polymerase residence on the DNA duplex, wherein Y is composed of alternating stretches of $N_3$ and $N_4$, and wherein $N_1$, $N_2$, $N_3$ and $N_4$ are different nucleotides selected from G, A, T and C. In these embodiments, the method may further comprise: (d) inactivating the fluorescent signal; (e) contacting the planar sample with a polymerase and an unlabeled nucleotide that is complementary to $N_4$; and (f) repeating steps (b) and (c). In some cases, step (f) may comprise repeating steps (b)-(e) multiple times.

In some embodiments, the double-stranded nucleic acids each comprise a fluorescently labeled oligonucleotide hybridized to the second strand downstream from the first strand, wherein the fluorescently labeled oligonucleotide comprises a quencher and extension of the first strand removes the quencher from some but not all of the quenched fluorescently labeled oligonucleotides, thereby generating a fluorescent signal for some but not all of the plurality of capture agents.

In some embodiments, extension of the double-stranded nucleic acid comprises contacting the planar sample with a mixture of labeled and unlabeled oligonucleotides and a ligase.

In any embodiment, the plurality of capture agents may be selected from the group consisting of: antibodies, aptamers, and oligonucleotide probes.

A kit is also provided. In these embodiments, the kit may comprise: (a) one or more capture agents, wherein the one or more capture agents can specifically bind to complementary sites in a planar sample. (b) one or more double-stranded nucleic acids comprising a first strand a second strand, wherein each of the one or more capture agents is linked to the double-stranded nucleic acid, and wherein a 5' end or 3' end of either the first strand or the second strand is extendible using the other strand as a template. In some embodiments, the kit may further comprise a polymerase or ligase. In some embodiments, the kit may further comprise a nucleotide mix comprising at least one of a fluorescent nucleotide, an unlabeled nucleotide, and a reversible terminator nucleotide. In some embodiments, the one or more capture agents may be selected from the group consisting of: an antibody, an aptamer and an oligonucleotide probe.

In some aspects, a method is provided for analyzing a planar sample. In some cases, the method comprises incubating the planar sample with a capture agent under conditions by which the capture agent specifically binds to complementary sites in the planar sample. In some cases, the capture agent is linked to a double-stranded oligonucleotide that comprises a first strand and a second strand. In some cases, a 3' end of the first strand is recessed relative to a 5' end of the second strand, thereby producing an overhang. In some cases, the method comprises contacting the planar sample with a polymerase and a plurality of nucleotides, thereby adding one or more nucleotides of the plurality of nucleotides to the overhang. In some cases, the method comprises reading a signal generated by addition of the one or more nucleotides to the overhang. In some cases, the plurality of nucleotides comprises a plurality of fluorescent nucleotides. In some cases, a fluorescent nucleotide of the plurality of nucleotides is added to the overhang. In some cases, the signal comprises a fluorescent signal. In some cases, the fluorescent signal is emitted directly from the fluorescent nucleotide added to the overhang. In other cases, two of the plurality of fluorescent nucleotides are added to the overhang. In this example, the fluorescent signal is a FRET signal generated by energy transfer between the two of the plurality of fluorescent nucleotides added to the overhang. In an alternative example, the fluorescent signal is a FRET signal generated by energy transfer between the fluorescent nucleotide from the plurality of fluorescent nucleotides added to the overhang and a fluorescent nucleotide that is present in the second strand. In some cases, extension of the first strand removes a quencher from a quenched fluorescently labeled oligonucleotide that is hybridized to the second strand, downstream from the first strand. In some cases, the planar sample is a formalin-fixed, paraffin-embedded (FFPE) section. In some cases, the capture agent is linked to the double-stranded oligonucleotide by a 5' end of the first strand. In other cases, the capture agent is linked to the double-stranded oligonucleotide by a 3' end of the second strand. In some cases, the method further comprises crosslinking the capture agent to the planar sample. In some cases, the reading comprises fluorescence microscopy. In some cases, the method further comprises producing an image showing a pattern of binding of the capture agent to the planar sample. In some cases, the one or more nucleotides of the plurality of nucleotides is added to the overhang by primer extension. In some cases, the capture agent is an antibody, an aptamer or an oligonucleotide probe.

In some aspects, a composition is provided comprising a plurality of capture agents that specifically bind to different complementary sites in a planar sample. In some cases, each of the plurality of capture agents is linked to a double-stranded oligonucleotide that comprises a first strand and a second strand. In some cases, a 3' end of the first strand in each of the double-stranded oligonucleotides is recessed relative to a 5' end of the second strand, thereby producing an overhang. In some cases, the overhang is different for each of the plurality of capture agents. In some cases, each of the plurality of capture agents is linked to the double-stranded oligonucleotide by a 5' end of the first strand. In other cases, each of the plurality of capture agents is linked to the double-stranded oligonucleotide by a 3' end of the second strand. In some cases, a sequence of the first strand is the same for each of the plurality of capture agents and a sequence of the second strand is different for each of the plurality of capture agents. In some cases, the overhang is of the formula 3'-N4nN1/N2/N3, wherein N1, N2, N3 and N4 are different nucleotides selected from G, A, T and C and n is 1 or more. In other cases, the overhang is of the formula 3'-YN1/N2-5', optionally followed by a short stretch of random nucleotides on the 5' end of the first strand to increase the overall polymerase residence on the DNA duplex, wherein Y is composed of alternating stretches of N3 and N4, and wherein N1, N2, N3 and N4 are different nucleotides selected from G, A, T and C. In some cases, Y is a nucleotide sequence of length n and wherein n is 0, 1, or more. In some cases, the order number of N3 stretches is odd and wherein the order number of N4 stretches is even. In some cases, the planar sample is a formalin-fixed, paraffin-embedded section (FFPE). In some cases, the plurality of capture agents are antibodies, aptamers, or oligonucleotide probes.

In some aspects, a method is provided for analyzing a planar sample. In some cases, the method comprises incubating the planar sample with the composition described above under conditions by which each of the plurality of capture agents specifically bind to different complementary sites in the planar sample. In some cases, the method comprises contacting the planar sample with a polymerase and a plurality of nucleotides, thereby adding one or more nucleotides of the plurality of nucleotides to the overhang of some, but not all, of the plurality of capture agents. In some cases, the method comprises reading a signal generated by addition of the one or more nucleotides from the plurality of nucleotides to the overhang of some, but not all, of the plurality of capture agents. In some cases, the method further comprises crosslinking the plurality of capture agents to the planar sample.

In some cases, the plurality of nucleotides comprises an incomplete nucleotide mix or a nucleotide mix comprising a reversible terminator nucleotide. In some cases, the signal comprises a fluorescent signal. In some cases, the reading comprises fluorescence microscopy. In some cases, the method further comprises producing an image showing a pattern of binding of the plurality of capture agents to the planar sample. In some cases, the plurality of nucleotides comprises: (i) a plurality of fluorescent nucleotides that are complementary to N1, N2 and N3, and a reversible terminator nucleotide that is complementary to N4; or (ii) a plurality of fluorescent nucleotides that are complementary to N1 and N2, an unlabeled nucleotide that is complementary to N3, and no nucleotide that is complementary to N4. In some cases, a fluorescent nucleotide of the plurality of fluorescent nucleotides is added to the overhang of some, but not all, of the plurality of capture agents. In some cases, the signal comprises a fluorescent signal generated by addition of the fluorescent nucleotide of the plurality of fluorescent nucleotides to some, but not all, of the plurality of capture agents. In some cases, the reading comprises fluorescence microscopy. In some cases, the method further comprises producing an image showing the pattern of binding of the plurality of capture agents to the planar sample. In some cases, the overhangs are of the formula 3'-N4nN1/N2/N3, wherein N1, N2, N3 and N4 are different nucleotides selected from G, A, T and C and n is 1 or more, and wherein the plurality of nucleotides comprises a plurality of fluorescent nucleotides that are complementary to N1, N2, N3 and a reversible terminator nucleotide that is complementary to N4. In some cases, the method further comprises inactivating the fluorescent signal, optionally, deprotecting the reversible terminator nucleotide; blocking the planar sample; and repeating the steps of contacting and reading. In some cases, the repeating further comprises repeating the steps of contacting, reading, inactivating, optionally deprotecting, and blocking a plurality of times. In other cases, the overhangs are of the formula 3'-YN1/N2-5', optionally followed by a short stretch of random nucleotides on the 5' end of the first strand to increase the overall polymerase residence on the DNA duplex, wherein Y is composed of alternating stretches of N3 and N4, and wherein N1, N2, N3 and N4 are different nucleotides selected from G, A, T and C. In some cases, Y is a nucleotide sequence of length n and wherein n is 0, 1, or more. In some cases, the order number of N3 stretches is odd and wherein the order number of N4 stretches is even. In some cases, the method further comprises inactivating the fluorescent signal, contacting the planar sample with a polymerase and an unlabeled nucleotide that is complementary to N4; and repeating the steps of contacting and reading. In some cases, the repeating comprises repeating the steps of contacting, reading, inactivating, and contacting a plurality of times. In some cases, each of the double-stranded oligonucleotides comprise a fluorescently labeled oligonucleotide hybridized to the second strand downstream from the first strand, wherein the fluorescently labeled oligonucleotide comprises a quencher and extension of the first strand removes the quencher from some, but not all, of the quenched fluorescently-labeled oligonucleotides, thereby generating a fluorescent signal for some, but not all, of the capture agents.

BRIEF DESCRIPTION OF THE FIGURES

The skilled artisan will understand that the drawings, described below, are for illustration purposes only. The drawings are not intended to limit the scope of the present teachings in any way.

FIG. 1A-1B (A) schematically illustrates a detection reagent composed of a combination of a capture agent that is conjugated to a double-stranded oligonucleotide. Upon detection and removal of unbound detection reagent the binding pattern is rendered by polymerase driven primer extension. Panel (B) schematically illustrates three approaches for linking the capture agent (an antibody in this case, but not excluding other possible capture agents) to a double stranded oligonucleotide (i.e., by chemical conjugation of the upper strand oligonucleotide to the capture agent; using streptavidin as an intermediate to connect biotinylated antibody and biotinylated oligonucleotide; and by linking biotinylated oligonucleotide to antibody chemically conjugated to streptavidin).

FIG. 2 schematically illustrates examples of capture agents that are bound to double-stranded oligonucleotides that have different overhangs. Such different overhangs represent a strategy to increase signal harvested from a particular capture agent by multiplication of positions in lower strand oligonucleotide complementary to detector base (dU in this case). The lower panel also shows how a different base labeled with a different fluorophore can be used as a FRET excitation pair for the "Detector" base. SEQ ID NOS: 1-4.

FIG. 8 schematically illustrates a multiplexed detection method that relies on removing quenchers from labeled oligonucleotides. Step 1: SEQ ID NOS 36-44, Step 2: SEQ ID NOS: 45-52, Step 3: SEQ ID NOS: 53-60, Step 4: SEQ ID NOS: 61-67.

FIGS. 9A and 9B schematically illustrate an embodiment that relies on cyclical re-annealing of polymerase priming nucleotides and a variant of the same approach that utilizes FRET. SEQ ID NOS: 68-80.

FIGS. 13A-13D show schematic illustration of two capture agents CD4 and CD8 linked to oligonucleotide duplexes (panel A) and data obtained from a multiplexed method whereby staining by this capture agents was sequentially detected on spleen cells smeared on a slide using a "reversible terminator" method (panels C-D). SEQ ID NOS: 89-92.

FIG. 18 shows A: multipanel design whereby antibody-DNA conjugates are incapable of polymerase extension because of 3'-dideoxy-terminator bases, but each panel can be activated for extension independently of others by an addition of a panel-specific primer. B: 18 aliquotes of mouse spleen cells were independently stained with different CD45 antibody conjugates that were designed such. Aliquots 1-3 (panel 1) can be detected by regular ABseq primer extension (top row), aliquots 4-6 (panel 2) were be extended after addition of Spacer1 oligonucleotide primer and aliquotes 7-9 (panel 3) can be extended after addition of Spacer2 oligonucleotide primer. C: Results of image quantification. Intensities of individual cell intensities displayed as a barcodes, one cell for each row, red color representing higher staining intensity. Columns represent intensities of cells on each extension cycle. The diagonal pattern shows the high specificity of spacer-based extension and the absence of signal cross-talk between panels and extension cycles.

DEFINITIONS

Figure 3:
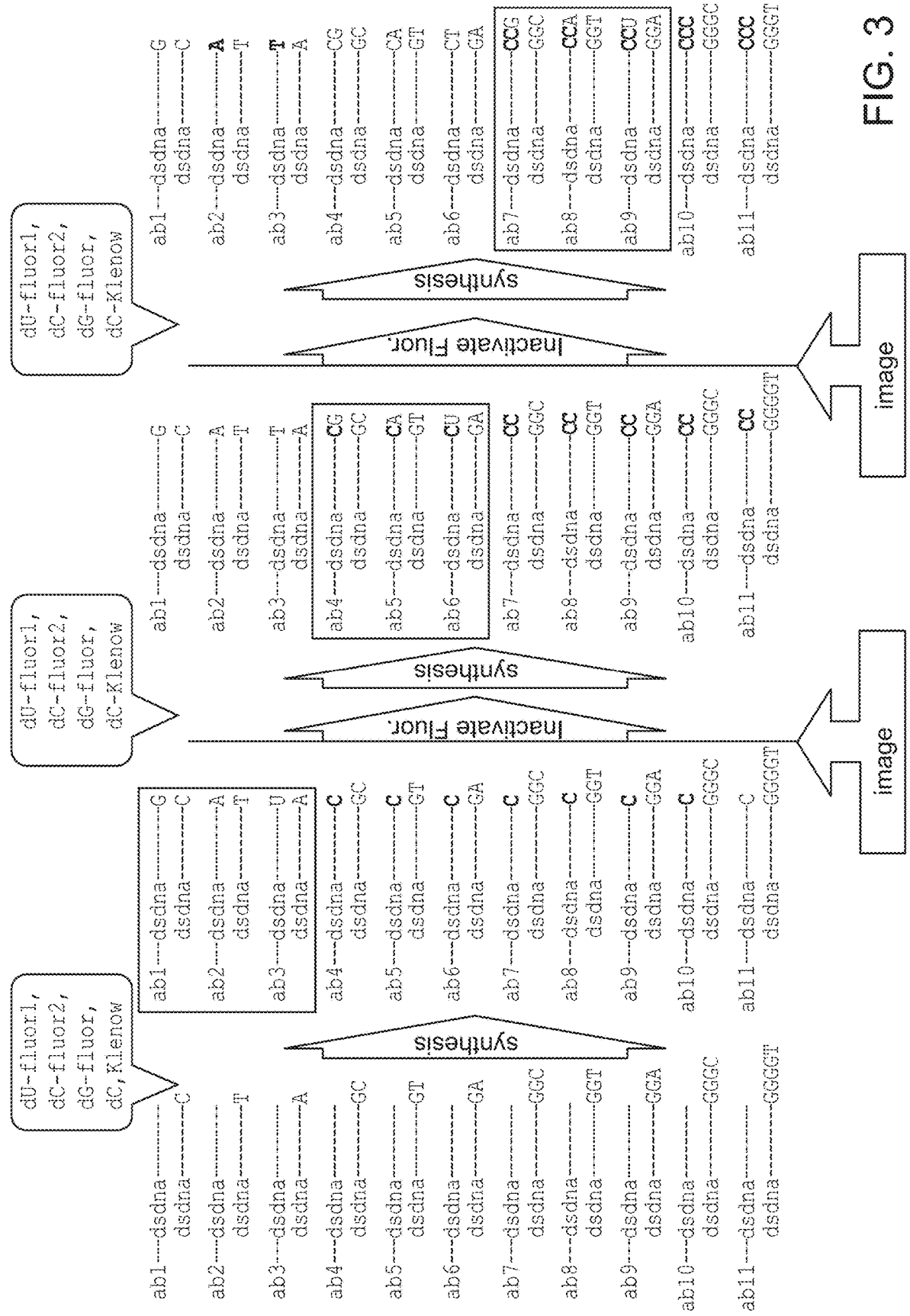
FIG. 3 schematically illustrates several cycles of a multiplexed detection method that relies on reversible dye terminators.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "biological feature of interest" refers to any part of a cell that can be indicated by binding to a capture agent. Exemplary biological features of interest include cell walls, nuclei, cytoplasm, membrane, keratin, muscle fibers, collagen, bone, proteins, nucleic acid (e.g., mRNA or genomic DNA, etc). fat, etc. A biological feature of interest can also be indicated by immunohistological methods, e.g., a capture agent that is linked to an oligonucleotide. In these embodiments, the capture agent binds to an site, e.g., a protein epitope, in the sample. Exemplary epitopes include, but are not limited to carcinoembryonic antigen (for identification of adenocarcinomas, cytokeratins (for identification of carcinomas but may also be expressed in some sarcomas) CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumour identification), CD20 (for identification of B-cell lymphomas), CD3 (for identification of T-cell lymphomas). Complementary nucleic acid molecules (e.g., DNA and/or RNA) in the sample provide binding complementary sites for oligonucleotide probes.

As used herein, the term "multiplexing" refers to using more than one label for the simultaneous or sequential detection and measurement of biologically active material.

As used herein, the terms "antibody" and "immunoglobulin" are used interchangeably herein and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (IgG$_1$, IgG$_2$, IgG$_3$, IgG$_4$), delta, epsilon and mu heavy chains or equivalents in other species. Full-length immunoglobulin "light chains" (of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, minibodies, single-chain antibodies, and fusion proteins comprising an antigen-binding portion of an antibody and a non-antibody protein. Also encompassed by the term are Fab', Fv, F(ab')$_2$, and or other antibody fragments that retain specific binding to antigen, and monoclonal antibodies. Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e. g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)).

The term "specific binding" refers to the ability of a binding reagent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a binding reagent and analyte when they are specifically bound in a capture agent/analyte complex is characterized by a K$_D$ (dissociation constant) of less than $10^{-6}$M, less than $10^{-7}$ M, less than $10^{-8}$ M, less than $10^{-9}$ M, less than $10^{-9}$ M, less than $10^{-11}$ M, or less than about $10^{-12}$ M or less.

A "plurality" contains at least 2 members. In certain cases, a plurality may have at least 2, at least 5, at least 10, at least 100, at least 1000, at least 10,000, at least 100,000, at least $10^6$, at least $10^7$, at least $10^8$ or at least $10^9$ or more members.

As used herein, the term "labeling" refers to attaching a detectable fluorophore to specific sites in a sample (e.g., sites containing an epitope for the antibody being used, for example) such that the presence and/or abundance of the sites can be determined by evaluating the presence and/or abundance of the label.

Figure 16:
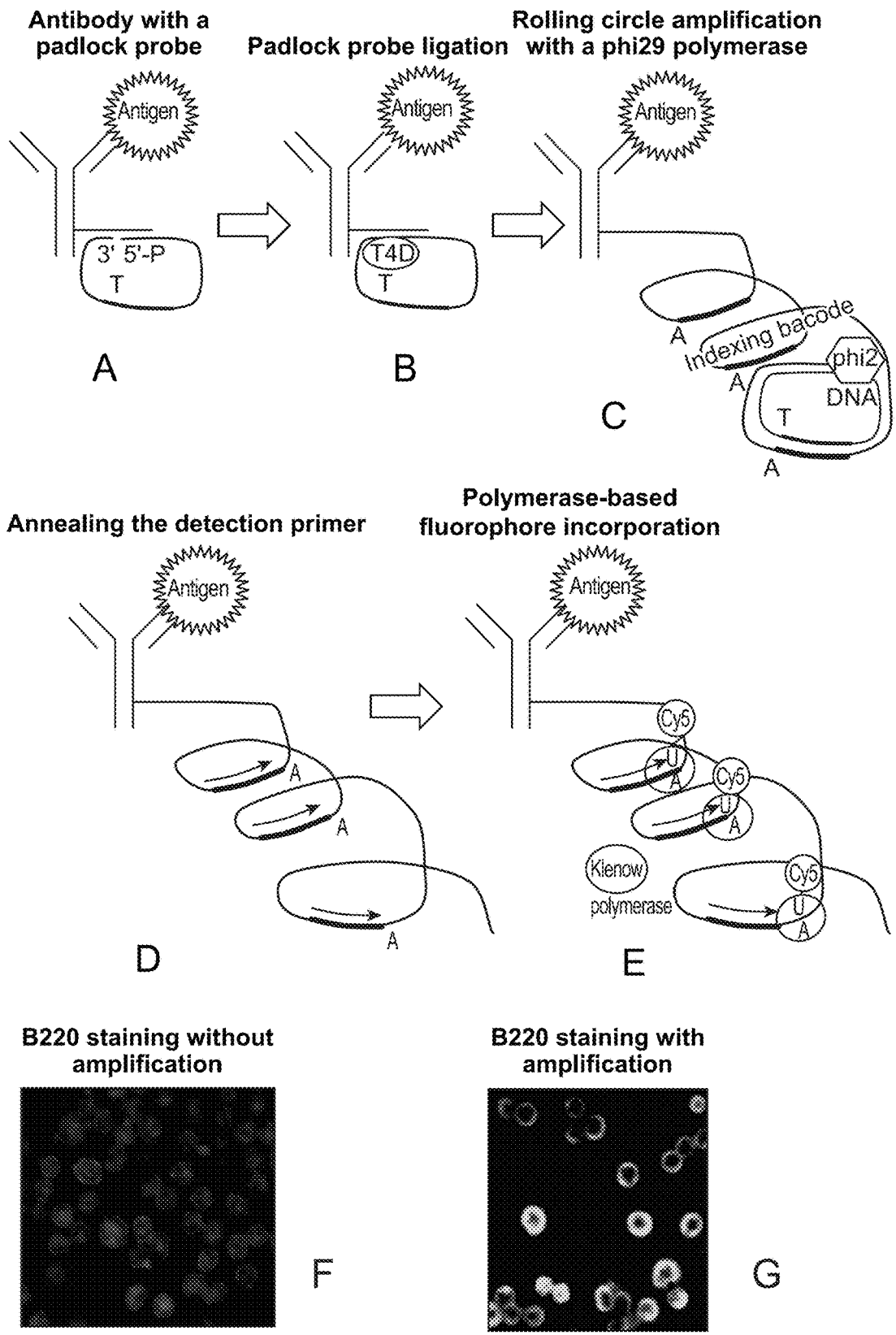
FIG. 16 illustrates enhanced antibody signal with rolling circle amplification. A. Antibody-DNA conjugate that consists of an antibody, a covalently linked linear linker oligonucleotide and a 5'-phosphorylated padlock nucleotide is used to stain the cellular antigens. Padlock probe contains the detection primer sequence (orange) followed by the fluorescent nucleotide incorporation site (T). B. Padlock oligonucleotide is treated with T4 DNA ligase, inducing its circularization. C. Rolling circle amplification with strand-displacing phi29 DNA polymerase created repeats of the reverse-complement of the detection primer sites (green). F-G. Staining of Mouse Spleen cells with antibody-DNA conjugate visualized by primer extension with dUTP-Cy5 without the rolling circle amplification (F) and after rolling circle amplification (G).

The term "labelling" refers to a method for producing a labeled sample in which any necessary steps are performed in any convenient order, as long as the required labeled sample is produced. For example, in some embodiments and as will be exemplified below, the capture agent may be already linked to a double-stranded nucleic acid prior to binding of the antibody to the sample, in which case a sample can be labeled using relatively few steps. In other embodiments, the capture agent may be linked to the first strand of the double stranded nucleic acid at the time at which it is incubated with the sample. In these embodiments, the second strand of the double stranded nucleic acid may be hybridized to the first strand of the double stranded nucleic acid after the antibody has bound to the sample. Along similar lines, the capture agent may be linked to a rolling circle amplification (RCA) primer at the time at which it is incubated with the sample. In these embodiments, the double-stranded nucleic acid may be produced by: a) hybridizing the sample with a padlock probe having ends that are complementary to the RCA primer, ligating the ends of the padlock probes together, and copying the padlock probe by rolling circle amplification and b) hybridizing an oligonucleotide to the RCA product, as illustrated in FIG. 16. In this example, the RCA product is the first strand of the double-stranded nucleic acid, and the oligonucleotides that are hybridized to the RCA product are the second strand of the double-stranded nucleic acid. In many embodiments, the labeling step may comprise crosslinking the capture agent to the planar sample so that subsequence manipulations can be done without the capture agent disassociating from its complementary sites in the planar sample. In these embodiments, if the capture agent is linked to the double-stranded nucleic acid prior to binding of the antibody to the sample, then the crosslinking step may be done immediately after binding of the antibody to the sample. In embodiments in which the capture agent is only linked to the first strand (or an RCA primer for making the same) at the time at which it is incubated with the sample, the sample may be cross-linked after binding of the antibody to the sample, and the double-stranded may be produced after crosslinking.

As used herein, the term "planar sample" refers to a substantially planar, i.e., two dimensional, material (e.g. glass, metal, ceramics, organic polymer surface or gel) that contains cells or any combinations of biomolecules derived from cells, such as proteins, nucleic acids, lipids, oligo/polysachharides, biomolecule complexes, cellular organels, cellular debris or excretions (exosomes, microvesicles). A planar cellular sample can be made by, e.g., growing cells on a planar surface, depositing cells on a planar surface, e.g., by centrifugation, by cutting a three dimensional object that contains cells into sections and mounting the sections onto a planar surface, i.e., producing a tissue section, absorbing the cellular components onto the surface that is functionalized with affinity agents (e.g. antibodies, haptens, nucleic acid probes), introducing the biomolecules into a polymer gel or transferring them onto a polymer surface electrophoretically or by other means. The cells or biomolecules may be fixed using any number of reagents including formalin, methanol, paraformaldehyde, methanol:acetic acid, glutaraldehyde, bifunctional crosslinkers such as bis(succinimidyl)suberate, bis(succinimidyl)polyethyleneglycole etc. This definition is intended to cover cellular samples (e.g., tissue sections, etc), electrophoresis gels and blots thereof, Western blots, dot-blots, ELISAs, antibody microarrays, nucleic acid microarrays etc.

As used herein, the term "tissue section" refers to a piece of tissue that has been obtained from a subject, fixed, sectioned, and mounted on a planar surface, e.g., a microscope slide.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a microscope slide.

As used herein, the term "spatially-addressable measurements" refers to a set of values that are each associated with a specific position on a surface. Spatially-addressable measurements can be mapped to a position in a sample and can be used to reconstruct an image of the sample.

A "diagnostic marker" is a specific biochemical in the body which has a particular molecular feature that makes it useful for detecting a disease, measuring the progress of disease or the effects of treatment, or for measuring a process of interest.

A "pathoindicative" cell is a cell which, when present in a tissue, indicates that the animal in which the tissue is located (or from which the tissue was obtained) is afflicted with a disease or disorder. By way of example, the presence of one or more breast cells in a lung tissue of an animal is an indication that the animal is afflicted with metastatic breast cancer.

The term "complementary site" is used to refer to an epitope for an antibody or aptamer, or a nucleic acid molecule if the capture agent is an oligonucleotide probe. Specifically, if the capture agent is an antibody, then the complementary site for the capture agent is the epitope in the sample to which the antibody binds. If the capture agent is an oligonucleotide probe, then the complementary site for the capture agent is a complementary sequence in a DNA or RNA molecule in the sample.

The term "epitope" as used herein is defined as small chemical groups on the antigen molecule that is bound to by an antibody. An antigen can have one or more epitopes. In many cases, an epitope is roughly five amino acids or sugars in size. One skilled in the art understands that generally the overall three-dimensional structure or the specific linear sequence of the molecule can be the main criterion of antigenic specificity.

A "subject" of diagnosis or treatment is a plant or animal, including a human Non-human animals subject to diagnosis or treatment include, for example, livestock and pets.

As used herein, the term "incubating" refers to maintaining a planar sample and capture agent under conditions (which conditions include a period of time, a temperature, an appropriate binding buffer and a wash) that are suitable for specific binding of the capture agent to molecules (e.g., epitopes or complementary nucleic acid) in the planar sample.

As used herein, the term "capture agent" refers to an agent that can specifically bind to complementary sites in a planar sample. Exemplary capture agents include, e.g., an antibody, an aptamer, and a nucleic acid (e.g., oligonucleotide) probe (which may be DNA or RNA) that hybridizes to a binding site. If antibodies are used, in many cases the antibodies may bind to protein epitopes. If nucleic acid probes are used, the nucleic acid probes may bind to, for example, genomic DNA or RNA (such that the location and abundance of intracellular RNAs can be detected).

As used herein, the term "extendible", in the context of, for example, a 3' end that is "extendible using the other strand as a template", means that a polymerase or ligase can add to the 3' end of a nucleic acid molecule, where the template sequence that is immediately downstream of the 3' end (i.e., on the other strand) determines which nucleotides (if a polymerase is used) or oligonucleotide (if a ligase is used) is added. A "5' end that is extendible using the other strand as a template" means that a ligase can add an oligonucleotide to the 5' end of a nucleic acid molecule, where the template sequence that is immediately downstream of the 5' end (i.e., on the other strand) determines which oligonucleotide is added.

As used herein, the term "template sequence that is immediately downstream to the 3' end" refers to the sequence on the other strand that use used as a template for extending the 3' end, starting with the first nucleotide. In embodiments in which the first strand is an RCA product, the template sequence that is immediately downstream of the 3' end may be a sequence in the RCA product. In embodiments in which the first strand is an oligonucleotide, the template sequence that is immediately downstream of the 3' end may be a 5' overhang.

As used herein, the term "capture agent that is linked to a double stranded nucleic acid" refers to a capture agent, e.g., an antibody or an oligonucleotide probe, that is non-covalently (e.g., via a streptavidin/biotin interaction) or covalently (e.g., via a click reaction or the like) linked to an double-stranded nucleic acid (which may be composed of two single-stranded oligonucleotide strands that are hybridized together, or an RCA product that is hybridized to a plurality of oligonucleotides) in a way that the capture agent can still bind to its binding site and the 3' end of one of the nucleic acids is accessible to a polymerase and/or ligase. The nucleic acid and the capture agent may be linked via a number of different methods, including those that use maleimide or halogen-containing group, which are cysteine-reactive. The capture agent and the nucleic acid may be linked at, proximal to or at the 5' end of one of the strands of the double stranded nucleic acid, proximal to or at the 3' end of one of the strands of the double stranded nucleic acid, or anywhere in-between.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides, ribonucleotides or a combination thereof, and may be produced enzymatically or synthetically (e.g., PNA as described in U.S. Pat. No. 5,948,902 and the references cited therein) and which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as an inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

As used herein, the term "oligonucleotide" refers to a multimer of at least 10, e.g., at least 15 or at least 30 nucleotides. In some embodiments, an oligonucleotide may be in the range of 15-200 nucleotides in length, or more.

As used herein, the term "reading" in the context of reading a fluorescent signal, refers to obtaining an image by scanning or by microscopy, where the image shows the pattern of fluorescence as well as the intensity of fluorescence in a field of view.

As used herein, the term "primer" is an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. A primer may be at least 10, e.g., at least 15 or at least 30 nucleotides in length.

As used herein, the term "single nucleotide 5' overhang" refers to a 5' overhang, where the overhang is a single nucleotide in length. Likewise, a "two nucleotide 5' overhang" is a 5' overhang, where the overhang is two nucleotides in length. The 3' end is recessed in a 5' overhang.

In certain cases, the various nucleotides of an overhang may be referred to by their position, e.g., "first position" and "second position". In these cases, the "position" is relative to the recessed 3' end. As such, in a multiple base 5' overhang, the "first" position of the overhang is immediately adjacent to the recessed 3' end and the "second" position of the overhang is immediately adjacent to the first position.

In certain cases, the complementary strands of a double stranded oligonucleotide or nucleic acid may be referred to herein as being the "first" and "second" or the "top" and "bottom" strands. The assignment of a strand as being a "top" or "bottom" strand is arbitrary and does not imply any particular orientation, function or structure.

As used herein, the term "signal generated by", in the context of reading a fluorescent signal generated by addition of the fluorescent nucleotide, refers to a signal that is emitted directly from the fluorescent nucleotide, a signal that is emitted indirectly via energy transfer to another fluorescent nucleotide (i.e., by FRET).

As used herein, the term "fluorescently labeled oligonucleotide comprising a quencher" refers to an oligonucleotide that contains a fluorophore and a quencher, wherein the quencher quenches the fluorophore in the same oligonucleotide.

As used herein, the term "different" in the context of different 5' overhangs that are different, refers to overhangs that have a different sequence. Overhangs of different lengths (e.g., GATC vs GAT) implicitly have a different sequence, even through one sequence may be encompassed by the other.

As used herein, the term "overhang" refers to a structure in which one strand of a double stranded nucleic acid ends such that nucleic acid synthesis can be initiated from that strand by a polymerase (or an oligonucleotide can be ligated to the end by a ligase) using the other strand as a template.

As used herein, the term "adding to the extendible 3' end", in the context of adding one or more nucleotides or an oligonucleotide to an extendible 3' end, refers to adding nucleotides (or an oligonucleotide) to an extendible 3' end using the other strand as a template (e.g., adding to the recessed 3' end of a 5' overhang using the overhang as a template).

As used herein, the term "template of the formula $3'-N_{4n}N_1/N_2/N_3-5'$ followed by an optional short stretch (e.g., 1-5 residues) of random nucleotides on the 5' end to increase the overall polymerase residence on the DNA duplex, where $N_1$, $N_2$, $N_3$ and $N_4$ are different nucleotides selected from G, A, T and C and n is 0, 1 or more", refers to a population of sequences that potentially contains single nucleotide overhangs of nucleotides $N_1$, $N_2$ and $N_3$ or the population of overhangs comprises two nucleotide overhangs of sequence 3'-$N_4N_1$-5', 3'-$N_4N_2$-5' and 3'-$N_4N_3$-5'-5' and, optionally overhangs of sequence, 3'-$N_4N_4N_1$-5', 3'-$N_4N_4N_2$-5' and 3'-$N_4N_4N_3$-5' and so on (e.g., four nucleotide overhangs of sequence 3'-$N_4N_4N_4N_1$-5', 3'-$N_4N_4N_4N_2$-5' and 3'-$N_4N_4N_4N_3$-5').

As used herein, the term "template of the formula 3'-$YN_1$/$N_2$-5', optionally followed by short stretch (e.g., 1-5 residues) of random nucleotides on the 5' end to increase the overall polymerase residence on the DNA duplex, wherein Y is a nucleotide sequence of length n (n is 0, 1 or more) composed of bases $N_3$ and $N_4$, wherein nucleotide $N_3$ is in odd positions and nucleotide $N_4$ is in even positions, counting from the start of the overhang and $N_1$, $N_2$, $N_3$ and $N_4$ are different nucleotides selected from G, A, T and C" refers to a population of sequences that potentially contain sequences 3'-$N_1$-5' and 3'-$N_2$-5' or optionally 3'-$N_3N_1$-5' and 3'-$N_3N_2$-5' or 3'-$N_3N_4N_1$-5' and 3'-$N_3N_4N_2$-5' and, optionally, overhangs of sequence 3'-$N_3N_4N_3N_1$-5' and 3'-$N_3N_4N_3N_2$-5' and so on (e.g., overhangs of sequence 3'-$N_3N_4N_3N_4N_1$-5' and 3'-$N_3N_4N_3N_4N_2$-5' and then 3'-$N_3N_4N_3N_4N_3N_1$-5' and 3'-$N_3N_4N_3N_4N_3N_2$-5').

As used herein, the term "alternating stretches" refers to two nucleotides stretches, where one "stretch" is a contiguous sequence of, e.g., up to 10, of the same nucleotide (e.g., a G, A, T or C), and the second stretch is contiguous sequence of, e.g., up to 10, of a different nucleotide, that alternate with one another, i.e., one stretch (e.g., a string of T's) occupies the odd positions and the other stretch (e.g., a string of A's) occupies the even positions.

As used herein, the term "incomplete nucleotide mix" comprises a nucleotide mix that contains one, two or three nucleotides (but not all four nucleotides) selected from G, A, T and C. The nucleotides may be labeled or unlabeled.

As used herein, the term "reversible terminator" refers to a chemically modified nucleotide base that when incorporated into growing DNA strand by DNA polymerase blocks further incorporation of bases. Such "reversible terminator" base and DNA strand can be deprotected by chemical treatment and following such deprotection DNA strand can be further extended by DNA polymerase.

As used herein, the term "fluorescently labeled reversible terminator" refers to a "reversible terminator" base which is labeled by fluorophore through linker cleavable by same treatment which is used to deprotect the DNA strand which ends with this base. Deprotecting the "fluorescently labeled reversible terminator" simultaneously activates the DNA strand for further extension and removes the fluorescent label from it.

For ease of description, many of the sequences described herein are written out in the 3' to 5' direction. While DNA sequences are routinely set forth in 5' to 3' direction, for the ease description, certain DNA sequences in the text below are described in the 3' to 5' direction. In each such case the directionality is specifically annotated.

Other definitions of terms may appear throughout the specification.

DETAILED DESCRIPTION

In some embodiments the method comprises producing a labeled a planar sample (e.g., an FFPE section mounted on a planar surface such as a microscope slide) using a capture agent that specifically binds to complementary sites in the planar sample. Methods for binding antibodies and/or nucleic acids to sites in the planar sample are well known.

In these embodiments, the capture agent in the labeled sample is linked to a double-stranded nucleic acid that comprises a first strand and a second strand (e.g., two oligonucleotide that are hybridized together or an RCA product that is hybridized to oligonucleotides) and the capture agent is linked (covalently or non-covalently via a biotin) to the double-stranded nucleic acid by the first strand of the double-stranded nucleic acid (e.g., by the 5' end, the 3' end, or anywhere in-between), and the 3' end or 5' end of one of the strands (e.g., the 3' end of the first strand, any 3' ends in the second strand, the 5' end of the first strand or any 5' ends in the second strand) is extendible using the other strand as a template. In some cases, the 3' end of the first strand may be recessed relative to the 5' end of the second strand, thereby defining an overhang. In other cases, the 5' end of the first strand may be recessed relative to the 3' end of the second strand, thereby defining an overhang. In many embodiments, the capture agent is cross-linked the planar sample, thereby preventing the capture agent from disassociating during subsequent steps. This crosslinking step may be done using any amine-to-amine crosslinker (e.g. formaldehyde, disuccinimiyllutarate or another reagents of similar action) although a variety of other chemistries can be used to cross-link the capture agent to the planar sample if desired. The method comprises reading a fluorescent signal generated by addition of a nucleotide or short oligonucleotide (e.g., of 2-10 bases) to the extendible end (e.g., the 3' end) of one of the strands. This step may be done by contacting the planar sample with a polymerase and a nucleotide mix, a ligase and a labeled oligonucleotide, or a combination of the two, thereby adding one or more nucleotides and/or a labeled oligonucleotide to the extendible end; and reading a fluorescent signal generated by addition of the one or more nucleotides or oligonucleotide to the extendible end.

As will be described in greater detail below, the fluorescent signal may be generated by a variety of different methods. For example, in some embodiments, the fluorescent signal may be fluorescence from a fluorescent nucleotide added to the end of the primer, or a FRET (fluorescence resonance energy transfer) signal resulting from the same. In other embodiments, the signal may generated by removing a quencher from a fluorescently labeled oligonucleotide that is also hybridized to the oligonucleotide.

In any implementation of the method, the reading step may be followed by inactivating the fluorescence after reading so that other binding events can be detected and read. In these embodiments, the fluorescence may be inactivated by peroxide-based bleaching, cleavage of fluorophore linked to nucleotide through cleavable linker (e.g. using TCEP as a cleaving reagent), base-exchange by exo+ polymerase such as Vent, or subsequent incorporation of quencher, for example.

Also, as will be described in greater detailed below, the method may be multiplexed in a way that a single planar sample can be interrogated by a plurality of different capture agents, where each antibody is linked to a different oligonucleotide (i.e., oligonucleotides of different sequence). In multiplex embodiments, the planar sample may be labeled using at least 5, at least 10, at least 20, at least 30, at least 50, or at least 100, up to 150 or more capture agents that are each linked to a different oligonucleotide, and binding of the capture agents can be separately read using a fluorescence microscope equipped with an appropriate filter for each fluorophore, or by using dual or triple band-pass filter sets to observe multiple fluorophores. See, e.g., U.S. Pat. No. 5,776,688. As noted below, the oligonucleotides linked to the capture agent may act as a splint for a padlock probe, and as a primer for initiating rolling circle amplification.

The capture agent used in some embodiments of the method may be linked to a double-stranded oligonucleotide that contains a 5' overhang (i.e., a recessed 3' end that can be extended by a polymerase or ligase) or a 3' overhang (i.e., a recessed 5' end that can be extended by a ligase). An example of such a capture agent is shown in FIGS. 1 and 2. In the example shown in FIG. 1B, the overhang is a single nucleotide overhang (e.g., an A), although a longer overhang (e.g., at least 2, at least 3, at least 4, at least 5, at least 6, at least 8, at least 10, at least 20, or at least at least 30, may be useful for other applications (e.g., multiplexed applications). As shown in FIG. 5 A-D, in certain cases, the overhang may contain a repeated sequence, e.g., 2, 3, 4, 5, or 6 or more repeats of the same sequence of 2, 3, 4, 5 or 6 nucleotides, thereby allowing the capture agent to be used in multiplexed applications as described below. In certain embodiments, the double stranded oligonucleotide may have a recessed 3' end at the other end of the oligonucleotide (i.e., at the end closest to the capture agent). However, this end may be designed to be not extendible. In certain circumstances, the double-stranded oligonucleotide may contain one or more third oligonucleotides that are hybridized to the overhang. In these embodiments, there will be a gap of 1, 2, 3, 4 or 5 or more nucleotides between the second strand of the double-stranded oligonucleotide and the oligonucleotide that is hybridized to the overhang (see, e.g., FIGS. 7 and 8). In multiplex embodiments, the plurality of capture agents may be distinguished by the sequence of the overhang and not by the sequence of the first strand of the double stranded oligonucleotide. In these embodiments, the second strand of the double stranded oligonucleotides is different for each of the capture agents. As shown in other figures, the method may also be implemented using capture agents that are linked to a primer that acts a splint for circularlizing a padlock probe and for priming amplification of circularlized padlock probe by rolling circle amplification. In these embodiments, the capture agents in the labeled sample may be linked to a rolling circle amplification product.

In certain cases, the fluorophore used may be a coumarin, a cyanine, a benzofuran, a quinoline, a quinazolinone, an indole, a benzazole, a borapolyazaindacene and or a xanthene including fluorescein, rhodamine and rhodol. In multiplexing embodiments, fluorophores may be chosen so that they are distinguishable, i.e., independently detectable, from one another, meaning that the labels can be independently detected and measured, even when the labels are mixed. In other words, the amounts of label present (e.g., the amount of fluorescence) for each of the labels are separately determinable, even when the labels are co-located (e.g., in the same tube or in the same area of the section).

Specific fluorescent dyes of interest include: xanthene dyes, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2', 7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G ($R6G^5$ or $G^5$), 6-carboxyrhodamine-6G ($R6G^6$ or $G^6$), and rhodamine 110; cyanine dyes, e.g., Cy3, Cy5 and Cy7 dyes; coumarins, e.g., umbelliferone; benzimide dyes, e.g. Hoechst 33258; phenanthridine dyes, e.g., Texas Red; ethidium dyes; acridine dyes; carbazole dyes; phenoxazine dyes; porphyrin dyes; polymethine dyes, e.g., BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, Napthofluorescein, Texas Red, Cy3, and Cy5, etc.

Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 and TOPRO3 (Molecular Probes, Eugene, Oreg.). Further suitable distinguishable detectable labels may be found in Kricka et al. (Ann Clin Biochem. 39:114-29, 2002), Ried et al. (Proc. Natl. Acad. Sci. 1992: 89: 1388-1392) and Tanke et al. (Eur. J. Hum. Genet. 1999 7:2-11) and others.

In addition to the labeling methods described above, the sample may be stained using a cytological stain, either before or after performing the method described above. In these embodiments, the stain may be, for example, phalloidin, gadodiamide, acridine orange, bismarck brown, barmine, Coomassie blue, bresyl violet, brystal violet, DAPI, hematoxylin, eosin, ethidium bromide, acid fuchsine, haematoxylin, hoechst stains, iodine, malachite green, methyl green, methylene blue, neutral red, Nile blue, Nile red, osmium tetroxide (formal name: osmium tetraoxide), rhodamine, safranin, phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, vanadyl sulfate, or any derivative thereof. The stain may be specific for any feature of interest, such as a protein or class of proteins, phospholipids, DNA (e.g., dsDNA, ssDNA), RNA, an organelle (e.g., cell membrane, mitochondria, endoplasmic recticulum, golgi body, nulear envelope, and so forth), a compartment of the cell (e.g., cytosol, nuclear fraction, and so forth). The stain may enhance contrast or imaging of intracellular or extracellular structures. In some embodiments, the sample may be stained with haematoxylin and eosin (H&E).

The structures of exemplary sulfhydryl-cleavable deoxynucleotide analogues that can be used in the present method are shown below. As would be recognized, these nucleotides are only exemplary and other nucleotides, including nucleotides that are cleavable by other stimuli (e.g., photocleavable nucleotides) can be used in the present method.

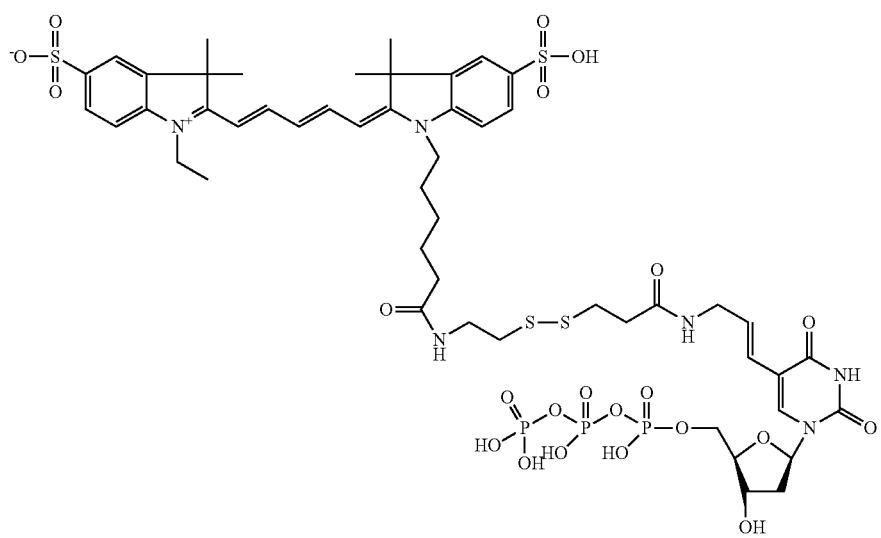

dUTP-SS-Cy5

Chemical Formula: C$_{50}$H$_{67}$N$_6$O$_{22}$P$_3$S$_4$
Molecular Weight: 1325.28

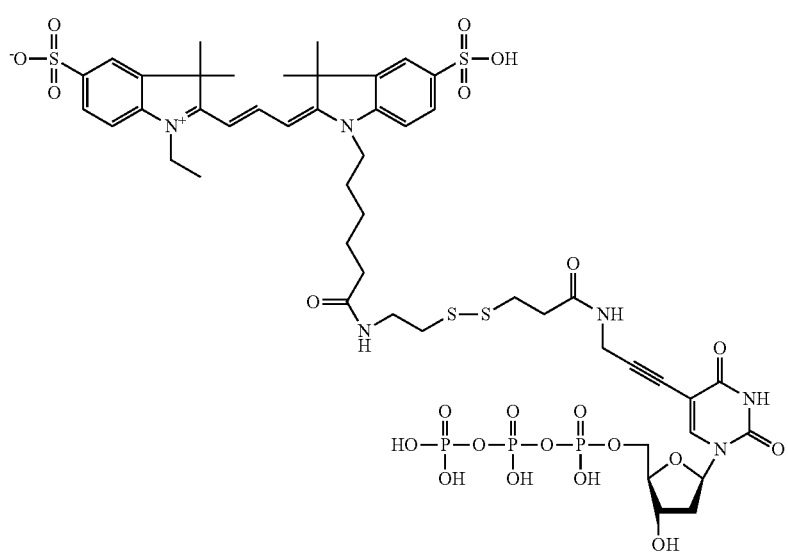

dCTP-SS-Cy3

Chemical Formula: C$_{48}$H$_{64}$N$_7$O$_{21}$P$_3$S$_4$
Molecular Weight: 1296.24

In order to further illustrate the present invention, the following specific examples are given with the understanding that they are being offered to illustrate the present invention and should not be construed in any way as limiting its scope.

Implementation I

In this example, the fluorescent signal may be produced by a fluorescent nucleotide that is added to (i.e., added by a polymerase or, if the fluorescent nucleotide is in an oligonucleotide, ligated onto) the 3' end of the primer. This method may comprise reading a signal from the added fluorescent nucleotide, or reading a FRET signal generated by energy transfer between two fluorescent nucleotides that are added to the primer.

The example shown in FIGS. 1 and 2 shows how an antibody can be linked to a oligonucleotide chemically, or via biotin/streptavidin interactions (FIG. 1B) and how a fluorescent signal can be generated by adding a fluorescent nucleotide to the end of the primer (FIG. 2). In this example, the antigen is stained by an antibody that is coupled to a DNA dimer with an overhanging 5' end (lower strand) and recessed 3' end (upper strand) either chemically (FIG. 1 top panel) or through streptavidin (FIG. 1 bottom and middle panels).

After binding the capture agent to the tissue sample, the pattern of binding of the capture agent may be determined using an on-slide end fill-in reaction by using a suitable polymerase (e.g., by exo⁻ Klenow, Bst, Taq, Klentaq, or an exo⁻ Klenow-Vent mixture) and fluorescently labeled nucleotide (FIG. 1 and FIG. 2 top panel).

If necessary, the signal-to-noise ratio can be increased by: a) multimerization of position complementary to labeling nucleotide (FIG. 2, middle panel); or b) by generating a FRET between two nucleotides are incorporated, whereby the emission wavelength of one of the nucleotides (FIG. 2, bottom panel C on the figure) serves as an excitation wavelength for another (FIG. 2, bottom panel U on the figure).

Fluorescence may be inactivated before addition of subsequent staining reagents by any convenient method including, but not limited to photobleaching, peroxide-based bleaching, inactivation by ozone, cleavage of fluorophore linked to nucleotide through cleavable linker (e.g. using TCEP as a cleaving reagent), base-exchange by exo+ polymerase such as Vent, subsequent incorporation of quencher.

In these embodiments, after fluorescence has been inactivated, the method can be repeated, i.e., the planar sample may be re-stained using a different antibody and fluorescence can be read.

Multiplexing

Figure 4:
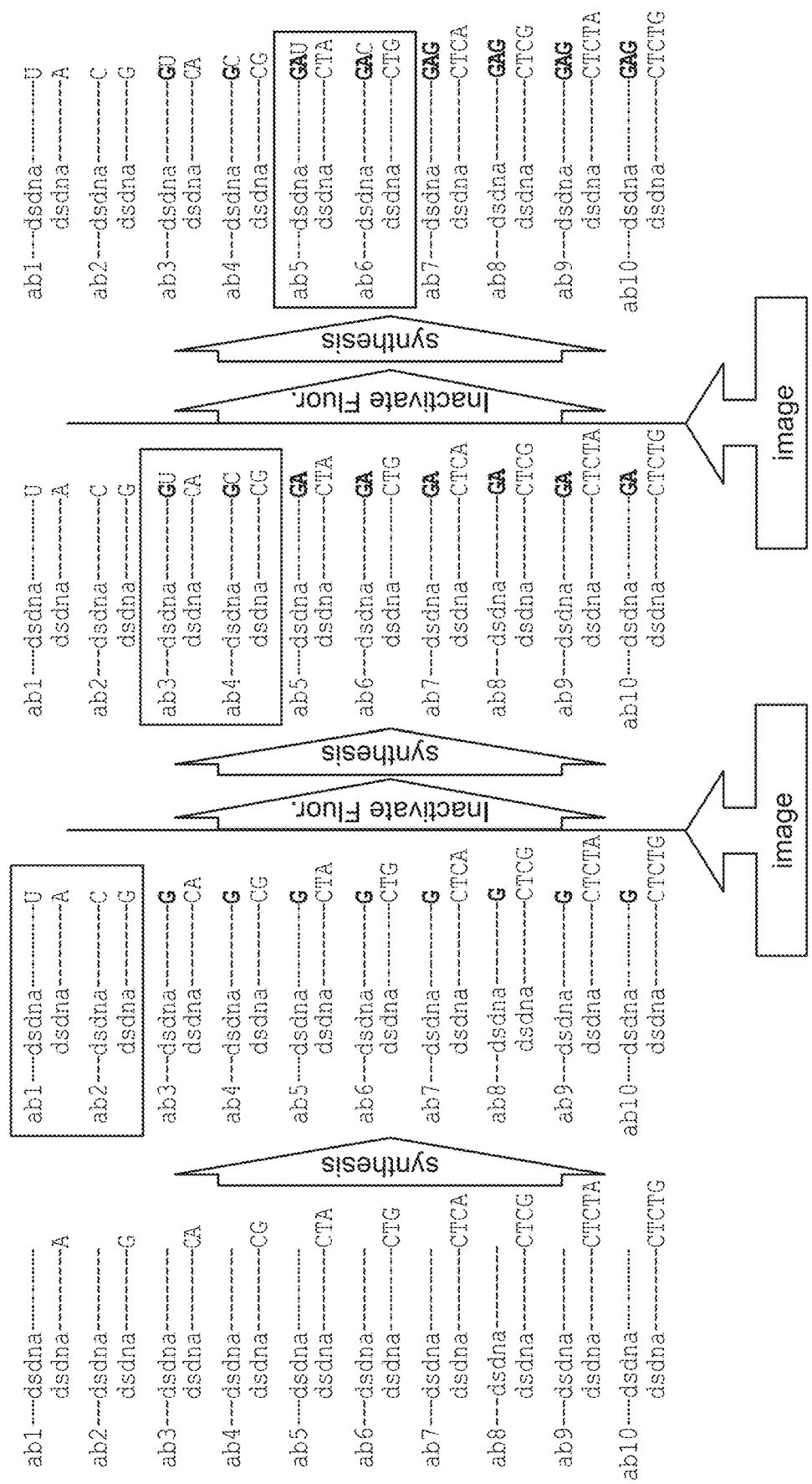
FIG. 4 schematically illustrates several cycles of a multiplexed detection method that relies on leaving out one of the four nucleotides per cycle.
Figure 5A:
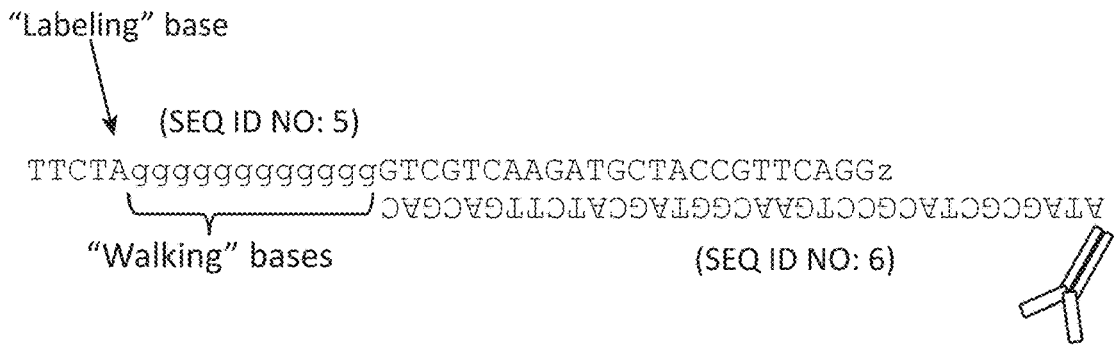
FIG. 5A-5D schematically illustrates an exemplary design of oligonucleotide duplexes for "reversible terminator" and "missing base" multiplexing methods. SEQ ID NOS: 5-12.
Figure 5B:
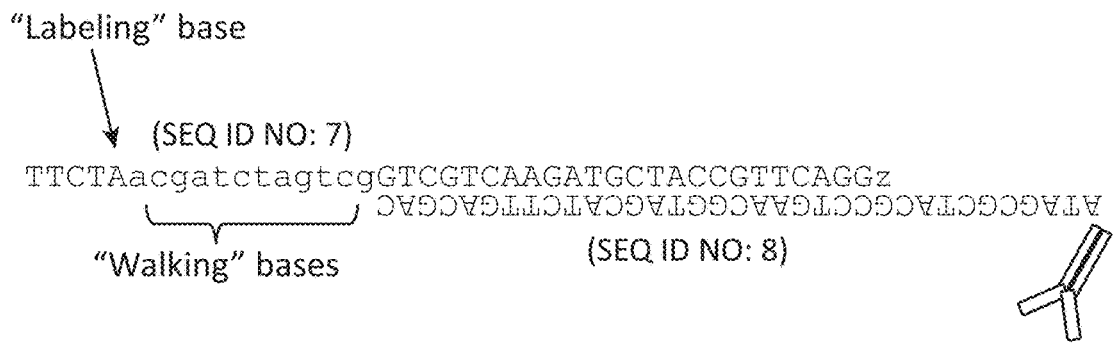
Figure 5C:
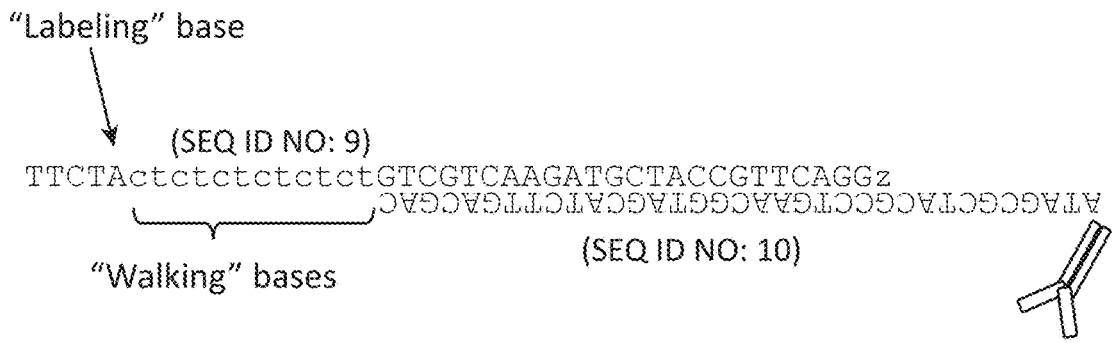
Figure 5D:
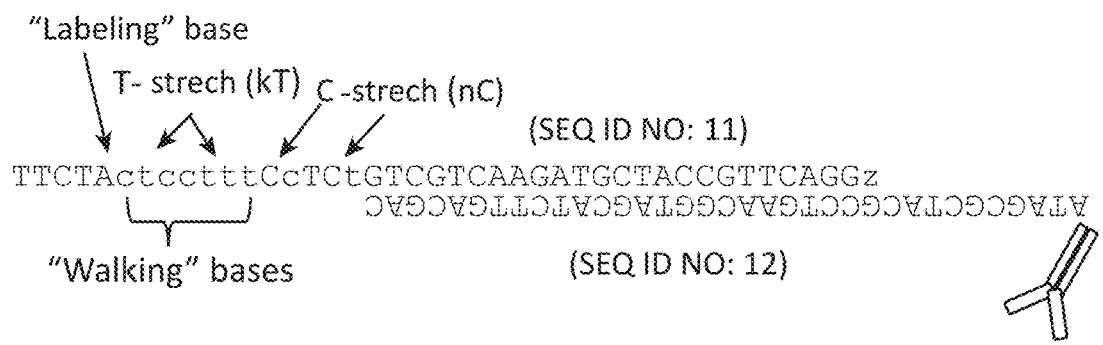

Multiplexing can be implemented using specially designed oligonucleotides using two different approaches, referred to as the "reversible terminator" and "missing base" approaches, which are described in greater detail below. Both of these methods rely on a composition comprising a plurality of (e.g., at least 5, at least 10, at least 20, at least 30, at least 50, or at least 100, up to 150 or more) capture agents that recognize different complementary sites, wherein: each of the capture agents is linked to a double-stranded nucleic acid (e.g., oligonucleotide) that comprises a first strand and a second strand; the capture agents are linked to a double-stranded nucleic acid by the (e.g., the 5' end of) the first strand; the 3' end of one of the strands in each of the double-stranded nucleic acids extendible using the other strand as a template, where the template is different for each of the capture agents. Examples of such compositions are illustrated in FIGS. 3 and 4, where the template is an overhang. The general principle shown in FIGS. 3 and 4 can be extended to double stranded nucleic acids that comprise RCA products. FIG. 3 shows a population of capture agents that have a template (e.g., overhang) defined by the formula: 3'-$N_{4n}N_1/N_2/N_3$-5' followed by short stretch of random composition on the 5' end to increase the overall polymerase residence on the DNA duplex, where $N_1$, $N_2$, $N_3$ and $N_4$ are different nucleotides selected from G, A, T and C and n is 0, 1 or more. FIG. 4, on the other hand, shows a population of capture agents that have an overhang defined by the formula 3'-$YN_1/N_2$-5', optionally followed by short stretch (e.g., 1-5 residues) of random nucleotides on the 5' end to increase the overall polymerase residence on the DNA duplex, wherein Y is a nucleotide sequence of length n (n is 0, 1 or more) composed of bases $N_3$ and $N_4$, wherein nucleotide $N_3$ is in odd positions and nucleotide $N_4$ is in even positions, counting from the start of the overhang and $N_1$, $N_2$, $N_3$ and $N_4$ are different nucleotides selected from G, A, T and C. As illustrated in FIGS. 3, 4 and 5, the sequence of the first strand is the same for each of the capture agents; and the sequence of the second strand is different for each of the capture agents. In these embodiments, the different second strands make the overhangs different between the different capture agents.

In some embodiments, the multiplex methods may generally comprise: (a) incubating a planar sample with an above-described antibody composition under conditions by which the capture agents bind to complementary sites in the planar sample; (b) cross-linking the capture agents to the planar sample; (c) contacting the planar sample with a polymerase and either an incomplete nucleotide mix of labeled and unlabeled nucleotides or a nucleotide mix where some or all nucleotides are fluorescent and some or all nucleotides are reversible terminator nucleotides or fluorescent reversible terminator nucleotides and optionally, contacting the planar sample with a mixture of labelled and unlabeled oligonucleotides and a DNA ligase enzyme that covalently attaches the short labelled oligonucleotides to the 3' end of the oligonucleotide duplexes that are attached to the specific capture agents. In these embodiments, oligonucleotides are only added to duplexes that an overhang that is complementary to the oligonucleotide. This method further comprises (d) reading, using fluorescence microscopy, a fluorescent signal generated by addition a nucleotide to some but not all of the capture agents. Following signal registration, this method may comprise (e) removing the fluorescent signals by chemical or photocleavage of a labeled nucleotide if the reversible terminator approach is used, followed by deprotecting the 3' ends of the oligonucleotides, enabling the addition of further nucleotides and/or oligonucleotides. Step (c) of this method may comprise (c) contacting the planar sample with a polymerase and: (i) a nucleotide mix that comprises fluorescent nucleotides that are complementary to $N_1$, $N_2$ and $N_3$ and a reversible terminator nucleotide that is complementary to $N_4$ or (ii) a nucleotide mix that comprises fluorescent reversible terminator nucleotides that are complementary to $N_1$, $N_2$ and $N_3$ and a reversible terminator nucleotide that is complementary to $N_4$ or (iii) a nucleotide mix that comprises fluorescent nucleotides that are complementary to $N_1$, and $N_2$, an unlabeled nucleotide that is complementary to $N_3$, and no nucleotide that is complementary to $N_4$, thereby adding fluorescent nucleotides onto the double-stranded oligonucleotides of some but not all of the capture agents thereby adding fluorescent nucleotides onto the double-stranded oligonucleotides of some but not all of the capture agents; and (d) reading, using fluorescence microscopy, a fluorescent signal generated by addition of a fluorescent nucleotide to some but not all of the capture agents. Step (c) can also be implemented by adding a labeled oligonucleotide to the duplex using a ligase. Examples of such methods are described in greater detail below.

Figure 6:
FIG. 6 schematically illustrates an exemplary design of oligonucleotide duplexes for a strategy that allows one to reduce the length of the lower strand oligonucleotide, creating an overhang in the case of highly multiplexed capture agent panels. SEQ ID NOS: 13-30.

With reference to FIG. 6 it is expected that in the case when larger panels of capture agents are to be employed (e.g. 100 and more) the length of the read over the oligonucleotide overhangs may increase accordingly. This may or may not reduce the efficiency of staining due to accumulation of primer extension errors along the length of the oligonucleotide duplex. To circumvent such potential source of signal loss a slight modification of design can be implemented. The plurality of capture agents can be divided in sets such that number of capture agents in the set does exceed the capacity of the multiplexing protocol to render staining without significant signal loss (e.g. 30). Each such set of capture agents will be conjugated to "terminated" (the last 3' base is dideoxy- or propyl-modified) upper strand oligonucleotide of the same sequence as in the original version of the "missing base" approach. The lower strand oligonucleotides will incorporate an additional set-specific region which will serve as a landing spot for an additional primer which is to be on-slide hybridized to the particular subset of the total plurality of the antibodies at the time when they are to be rendered. This approach allows not to extend the reads beyond certain threshold and at the same time have an unlimited potential number of capture agents in the sample.

Reversible Terminator Method

This implementation of the method relies on reversible terminators, i.e., chain terminator nucleotides that can be de-protected after incorporation, thereby allowing further nucleotides to be added to that nucleotide.

This method can be implemented using a composition comprising a plurality of capture agents that are linked to a double stranded nucleic acid (e.g., oligonucleotides), as illustrated in FIG. 3. In these embodiments, the top strand of the double stranded nucleic acid is linked to the capture agent and may be the same for each antibody, and the sequence of the bottom strand varies between capture agents. As shown on FIG. 5A, the 5' end of the lower strand of the double-stranded nucleic acid (which may form an overhang) is of the general 3'-$N_{4n}N_1/N_2/N_3$-5' followed by short stretch of random nucleotides on the 5' end to increase the overall polymerase residence on the DNA duplex, where $N_1$, $N_2$, $N_3$ and $N_4$ are different nucleotides selected from G, A, T and C and n is 0, 1 or more. As shown on FIG. 5B a more general formula of lower oligonucleotide overhang 3'-$XN_1/N_2/N_3$-5', where $N_1$, $N_2$, $N_3$ are different nucleotides selected from G, A, T and C and X is a nucleotide stretch of bases Xi (such that Xi are different nucleotides selected from G, A, T and C) of random composition and length is also applicable in this method.

In certain embodiments, this method may comprise: (a) incubating a planar sample with a multiplex antibody composition in which the overhangs are of the formula 5'-$N_1/N_2/N_3N_{4n}$, wherein $N_1$, $N_2$, $N_3$ and $N_4$ are different nucleotides selected from G, A, T and C and n is 1 or more; under conditions by which the capture agents specifically bind to complementary sites in the planar sample; (b) cross-linking the capture agent to the planar sample; (c) contacting the planar sample with a polymerase and a nucleotide mix that comprises fluorescent nucleotides that are complementary to $N_1$, $N_2$ and $N_3$ and a reversible terminator nucleotide that is complementary to $N_4$ and/or ligating a oligonucleotide that comprises a labeled nucleotide; and (d) reading, using fluorescence microscopy, a fluorescent signal generated by addition of a nucleotide to some but not all of the capture agents. This cycle may be repeated by (e) inactivating the fluorescent signal, deprotecting the reversible terminator nucleotide and (f) blocking the planar sample; and repeating steps (c) and (d). In certain embodiments, the method may comprise repeating steps (c), (d) (e) and (f) multiple times. The reagent used for blocking may vary depending on the chemistry used. In certain embodiments, the sample may be blocked with a thiol-reactive compounds such as cysteine, glutathione or iodoacetamide.

For example, this method can be implemented using a composition comprising: a first antibody linked to a first double stranded oligonucleotide, wherein the first double stranded oligonucleotide comprises a single nucleotide 5' overhang comprising base $N_1$; a second antibody linked to a second double stranded oligonucleotide, wherein the second double stranded oligonucleotide comprises a single nucleotide 5' overhang comprising base $N_2$; a third antibody linked to a third double stranded oligonucleotide, wherein the third double stranded oligonucleotide comprises a single nucleotide 5' overhang comprising base $N_3$; a fourth antibody linked to a fourth double stranded oligonucleotide comprises a two nucleotide 5' overhang, wherein the first position of the overhang comprises base $N_4$ and the second position of the overhang is base $N_1$; a fifth antibody linked to a fifth double stranded oligonucleotide, wherein the fifth double stranded oligonucleotide comprises a two nucleotide 5' overhang, wherein the first position of the overhang comprises base $N_4$ and the second position of the overhang is base $N_2$; and a sixth antibody linked to a sixth double stranded oligonucleotide, wherein the sixth double stranded oligonucleotide comprises a two nucleotide 5' overhang, wherein the first position of the overhang comprises base $N_4$ and the second position of the overhang is base $N_3$, wherein $N_1$, $N_2$, $N_3$ and $N_4$ are different nucleotides selected from G, A, T and C. An example of such a population of capture agents is shown in FIG. 3.

In RCA embodiments, the strand linked to the antibodies may be different for each of the antibodies, where the RCA product contains a sequence conforming to the formula described above in each repeat of the RCA product.

In certain implementations, the composition may also contain a seventh antibody linked to a seventh double stranded oligonucleotide, wherein the seventh double stranded oligonucleotide comprises a multiple nucleotide 5' overhang, wherein the first position of the overhang comprises base $N_4$, the second position of the overhang is base $N_4$ and third is selected from $N_1$, $N_2$, and $N_3$. The same principle may be applied to overhangs that have more than 7 positions (e.g., 9, 10, 11 up to 20, 30, or 40 ore more) positions.

In this implementation of the method, the planar sample can be co-stained simultaneously using a panel of capture agents, each labeled with one oligonucleotide duplex designed according to the strategy outlined on FIG. 3. The duplexes are designed in such a way that each antibody has the same upper strand sequence linked, covalently or through streptavidin, to an antibody through the 5' end. The lower strand changes from antibody to antibody. In this implementation, the general formula for the lower strand is 3'-dideoxydC-sequence-complimentary-to-upper-strand $G_n$A/T/C-5'. One type of lower strand base (nucleotide G in this example) is reserved for step-wise progression and its complementary pair on the upper strand is never used in labeled form. The other three bases are complementary to labeled nucleotides and can be used to identify three capture agents per cycle. In a more general case the general formula for the lower strand is 3'-dideoxydC-sequence-complimentary-to-upper-strand-X—$N_1/N_2/N_3$-5' where $X_i$ of X is any nucleotide excluding one reserved for "walking base" of this particular cycle and X is any base as shown on FIG. 5B. This design ensures that: a) no two antibody species contain the same duplex and b) only three different capture agents are detected at a time. Each cycle includes: (a) a labeling step in which the three capture agents are labeled and duplexes on the rest are extended one base at a time, (b) an imaging step and (c) a destaining/deprotection step. During cycle to cycle transition the added fluorescent labels from the previous cycle are inactivated by any of the suitable methods, including but not limited to: cleavage of fluorophore off the nucleotide (if the labeled nucleotide is linked to the fluorophore through a cleavable linker); peroxide based bleaching; photobleaching; chemically-assisted photobleaching; labeled base replacement by exo+ polymerase, etc. After or simultaneously with inactivation of the fluorophores added in the previous reaction, the unlabeled "extension" nucleotide that has been added to the remainder of the capture agents is activated by cleavage of the protective group off its 3' end. Cleavage of the protective group, in turn, allows that nucleotide to be extended in the next cycle. Since the A, T and C are reserved for incorporation of a labelled nucleotide, those nucleotides only occur at the end of each lower strand of the duplex. This approach is based on the chemical nature of reversible terminators, which precludes upper strand extension for more than one nucleotide at a time even on polyG stretches of the lower strand. Optionally, a quencher labeled nucleotide can be incorporated following the labeled nucleotide. The performance of "reversible terminator method" as exemplified in sequential detection of CD4 and CD8 positive T-cells in smears of mouse splenocytes is illustrated in FIG. 13A-D.

Missing Base Method

This implementation of the method relies on a "missing" base design in which, in each cycle, two labeled and one unlabeled nucleotides are added to the reaction, and the "missing base" prevents the primers from being extended by more than a single nucleotide.

This method can be implemented using a composition comprising a plurality of capture agents that are linked to double stranded nucleic acids, as illustrated in FIG. 4. In these embodiments, the top strand of the double stranded nucleic acids is linked to the capture agent and may be the same for each antibody, and the sequence of the bottom strand varies between capture agents. As shown in FIG. 4, the 5' end of the lower strand of the double-stranded oligonucleotide (which forms the overhang) is of the general formula 3'-$YN_1/N_2$-5', optionally followed by short stretch (e.g., 1-5 residues) of random nucleotides on the 5' end to increase the overall polymerase residence on the DNA duplex, wherein Y is a nucleotide sequence of length n (n is 0, 1 or more) composed of bases $N_3$ and $N_4$, wherein nucleotide $N_3$ is in odd positions and nucleotide $N_4$ is in even positions, counting from the start of the overhang and $N_1$, $N_2$, $N_3$ and $N_4$ are different nucleotides selected from G, A, T and C.

Also a more general formula 3'-$YN_1/N_2$-5', wherein $N_1$, $N_2$, $N_3$ and $N_4$ are different nucleotides selected from G, A, T and C and Y is a nucleotide sequence of length n (n is 0, 1 or more) composed of alternating random length stretches of bases $N_3$ and $N_4$ such that the order number of $N_3$—stretches is odd and of $N_4$ stretches is even, may be applicable in this method In certain embodiments, this method may comprise: (a) incubating a planar sample with a multiplex antibody composition in which the overhangs are of the formula (3'-$YN_1/N_2$-5') described in the prior paragraph; under conditions by which the capture agents specifically bind complementary sites in the planar sample; (b) cross-linking the capture agent to the planar sample; (c) contacting the planar sample with a polymerase and a nucleotide mix that comprises fluorescent nucleotides that are complementary to $N_1$, and $N_2$, an unlabeled nucleotide that is complementary to $N_3$ and no nucleotide that is complementary to $N_4$ and/or ligating an oligonucleotide that has a labeled nucleotide; and (d) reading, using fluorescence microscopy, a fluorescent signal generated by addition of a nucleotide to some but not all of the capture agents. This cycle may be repeated by (e) inactivating the fluorescent signal, (f) blocking the sample and contacting the planar sample with a polymerase and an unlabeled nucleotide that is complementary to $N_4$ and/or contacting the sample with a labeled oligonucleotide and a ligase; and repeating steps (c) (d). In certain embodiments, the method may comprise repeating steps (c), (d), (e) and (f) multiple times.

This method can be implemented using a capture agent composition that comprises: a first antibody linked to a first double stranded oligonucleotide, wherein the first double stranded oligonucleotide comprises a single nucleotide 5' overhang comprising base $N_1$; a second antibody linked to a second double stranded oligonucleotide, wherein the second double stranded oligonucleotide comprises a single nucleotide 5' overhang comprising base $N_2$; a third antibody linked to a fourth double stranded oligonucleotide, wherein the third double stranded oligonucleotide comprises a two nucleotide 5' overhang, wherein the first from the 3' position of the overhang comprises base $N_4$ and the second position comprises $N_1$; and a fourth antibody linked to a fourth double stranded oligonucleotide, wherein the fourth double stranded oligonucleotide comprises a two nucleotide 5' overhang, wherein the first position of the overhang comprises base $N_4$ and the second position comprises base $N_2$, wherein $N_1$, $N_2$, $N_3$ and $N_4$ are different nucleotides selected from G, A, T and C. An example of such a population of capture agents is shown in FIG. 4.

In certain implementations, the composition may also contain a fifth antibody linked to a fifth double stranded oligonucleotide, wherein the fifth double stranded oligonucleotide comprises a multiple nucleotide 5' overhang, wherein the first position of the overhang comprises base $N_4$, the second position comprises base $N_3$, and the third position comprises $N_1$ or $N_2$.

Overall there is no theoretical limits to the number of co-detected complementary sites, e.g., antigens, both in the case of "reversible terminator" and of "missing base" approach The missing base approach does not use reversible terminators. Instead, extension of a single nucleotide is ensured by using two interchanging bases (e.g., T and C as shown in FIG. 4 instead of the corresponding G in the "reversible terminators" approach) and adding only one of the two dNTPs at a time in the primer extension reaction. After the incorporation of the first nucleotide, the absence of the second dNTP causes strand elongation to stall, thereby ensuring that the primers are extended by only a single nucleotide. As in the previous strategy, all complementary sites can be co-stained simultaneously using capture agents, each labeled with a specific oligonucleotide duplex.

In this embodiment, the duplexes can be designed using the strategy shown in FIG. 4, i.e., in such a way that each antibody has the same upper stand oligonucleotide sequence linked to it via covalent bond or through a streptavidin-biotin interaction. In this implementation, the lower strand changes from antibody to antibody. In this method, the general formula for the lower strand is 3' ddC-sequence-complimentary-to-upper-strand-YA/$N_2$-5' where Y is composed of bases T and C such that T can be found only in even and C only at odd positions. Or in the more general case 3'-$YN_1/N_2$-5', wherein $N_1$, $N_2$, $N_3$ and $N_4$ are different nucleotides selected from G, A, T and C and Y is a nucleotide sequence of length n (n is 0, 1 or more) composed of alternating random length stretches of bases $N_3$ and $N_4$ such that the order number of $N_3$—stretches is odd and of $N_4$ stretches is even. In the first simple implementation two base pairs of the lower strand (T and C as in exemplary design on FIG. 4) are reserved for step-wise progression and their complementary pair on the upper strand is never labeled. The other two bases are complementary to labeled nucleotides and can render the staining with two different capture agents per cycle. Such design ensures that a) no two capture agents contain the same duplex and b) only two different antibody are read per cycle. In this implementation, each cycle can have three steps: a labeling step in which the two capture agents are labeled by incorporation of fluorescent dNTPs and all of the other duplexes are extended one base at a time, an imaging step, and a de-staining/reactivation step.

In RCA embodiments, the strand linked to the antibodies may be different for each of the antibodies, where the RCA product contains a sequence conforming to the formula described above in each repeat of the RCA product.

Figure 15:
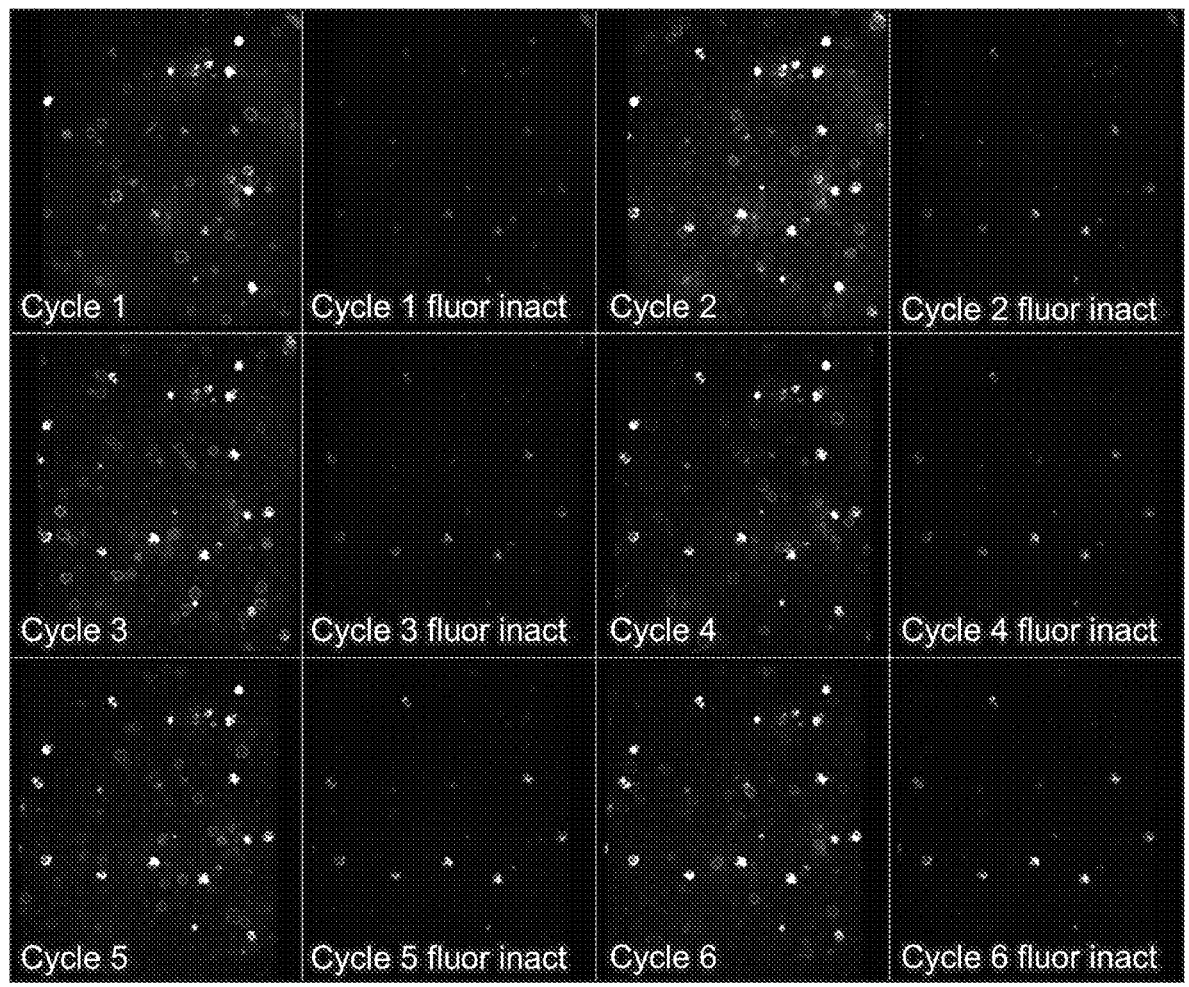
FIG. 15 is 12 panels of images showing the first 6 cycles of rendering the 30 populations barcoded by CD45 (as per scheme on FIG. 14). Two populations were co-detected per cycle of rendering. In each cycle control image was acquired after fluorescence inactivation.

During cycle-to-cycle transition the labeled capture agents from the prior cycle can be bleached/destained in the same way as described above. Optionally, instead of bleaching, a quencher labeled nucleotide can be incorporated after the labeled base. Because, in this embodiment, the position that is labeled is the last position in the overhang, the labeled capture agents from prior cycle cannot be re-labeled in later cycles because all nucleotide positions in the overhang have been filled in. The performance of "reversible terminator method" as exemplified in sequential detection of CD4 and CD8 positive T-cells in smears of mouse splenocytes is illustrated in FIG. 13, 15 and FIG. 16.

Implementation II

Figure 7:
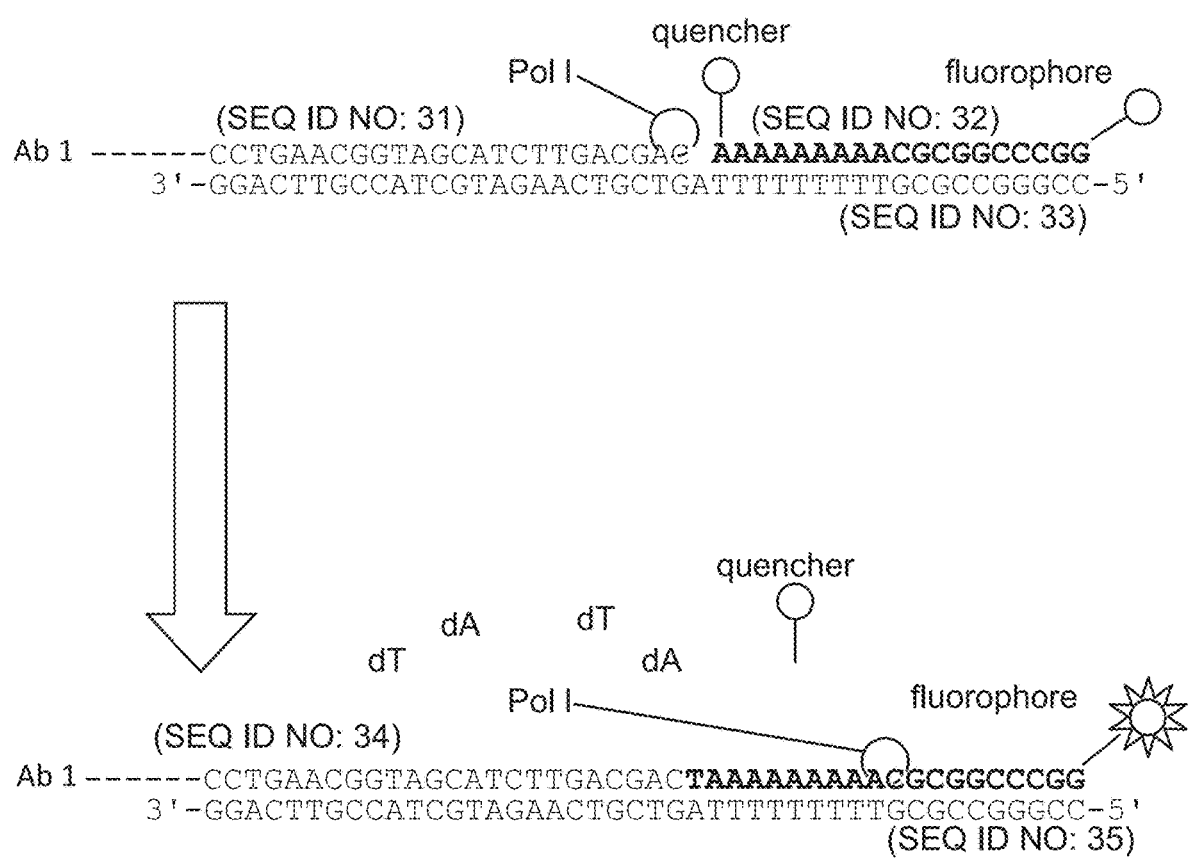
FIG. 7 schematically illustrates an example of a detection method that relies on removing a quencher from a labeled oligonucleotide by nick translation. SEQ ID NOS: 31-35.

In this method, extension of a primer by nick translation removes a quencher from a fluorescently labeled "detector" oligonucleotide that is hybridized to the lower strand oligonucleotide in such a way that is positioned downstream from the upper strand primer. The principles of this method are illustrated in FIG. 7. A multiplexed version of this method is shown in FIG. 8.

In certain embodiments, the multiplexed implementations may comprise: (a) incubating the planar sample with a plurality of capture agents that are linked to a double-stranded oligonucleotide; (b) crosslinking the capture agents to the planar sample; (c) extending a primer that is hybridized to the oligonucleotide of a first set of capture agents of the plurality, thereby generating a first set of fluorescent signals (e.g., by removing the quencher from a labeled oligonucleotide that is hybridized to the oligonucleotide downstream from the primer), e.g., by adding a nucleotide using a polymerase or by adding an oligonucleotide using a ligase; (d) reading the first set of fluorescent signals using fluorescence microscopy; (e) inactivating the fluorescence; (f) extending a primer that is hybridized to the oligonucleotide of a second set of capture agents of the plurality, thereby generating a second set of fluorescent signals (e.g., by removing the quencher from a labeled oligonucleotide that is hybridized to the oligonucleotide downstream from the primer); (g) reading the second set of fluorescent signals using fluorescence microscopy; and (h) comparing the images produce in steps (d) and (g).

In this method, the architecture of the double-stranded oligonucleotides linked to the capture agent has a specific design which is effectively enabling rendering of the capture agent binding pattern by "nick translation". In particular the duplex of the upper strand and the lower strand oligonucleotide with long 5' overhang of the lower strand is further hybridized to a small detector oligonucleotide labeled both by fluorescent and the quencher. There is a predesigned gap between the initial upper strand and the upper strand detector oligo. During cyclic staining this gap is "walked" by either "reversible terminator" or "missing base" (similar to described in previous sections) until the gap is reduced to a single base nick. Extension and progression through the nick on the upper strand by "nick translating" polymerase such as DNA pol I removes the quencher from some but not all of the quenched fluorescently labeled oligonucleotides, thereby generating a fluorescent signal for some but not all of the capture agents.

In some embodiments the method generally comprises: (i) labeling a planar sample with: i. a first antibody, wherein the first antibody is linked to a first oligonucleotide duplex comprising, lower strand oligonucleotide with a unique sequence hybridized thereto: (i) an oligonucleotide upper strand "primer" and (ii) a labeled upper strand oligonucleotide comprising a 5' quencher at a site that is downstream from the primer; and a fluorophore downstream from the quencher and ii. a second antibody, wherein the second antibody is linked to a second oligonucleotide duplex comprising, lower strand oligonucleotide with unique sequence hybridized thereto: (i) an oligonucleotide upper strand "primer" and (ii) an upper strand oligonucleotide labeled both by fluorophore and a quencher; wherein the gap between the 3' end of the primer and the 5' end of the labeled oligonucleotide is different for the first and second oligonucleotides; (ii) incubating the tissue sample with a first nucleotide mix and a polymerase, thereby removing the quencher from only the labeled oligonucleotide that is hybridized to the first oligonucleotide and producing a first fluorescent signal; (iii) reading the first fluorescent signal using fluorescence microscopy; (iv) inactivating the fluorescent signal by further progression of nick-translating polymerase; (v) incubating the tissue sample with a second nucleotide mix and a polymerase, thereby removing the quencher from only the labeled oligonucleotide that is hybridized to the second oligonucleotide and producing a first fluorescent signal; and (vi) reading the second fluorescent signal from the planar sample using fluorescence microscopy.

FIGS. 7 and 8 show an example of this method. The multiplexing method shown in FIG. 8 has the following steps:

Step 1: The planar sample is stained by capture agents that are coupled to a DNA double-stranded oligonucleotide chemically or through streptavidin (as described in FIG. 1) such that the top strand of the duplex contains a nick or a single base deletion followed by a nucleotide stretch bordered by a fluorophore and its quencher on two ends ("molecular beacon" or Taqman based design).

Step 2: Staining pattern is rendered by a nick-translation reaction carried out by any 5' exo+ polymerase such as DnaPolI Klenow fragment in the presence of a single letter (A as in FIG. 5 for example). Nick translation removes the quencher but stops before removing the part of the duplex with the fluorophore.

Step 3: For rendering of other staining reagents, the fluorescence is removed by continuing nick translation in the presence of the letters of the stretch bearing the fluorophore.

Step 4: When multiplexing is desired, multiplexing can be achieved by special design of oligonucleotide duplexes attached to detection reagents. In particular each antibody set (two or three per cycle) has a gap of an increasing length between the top strand priming and the detector oligonucleotide. This sequence gap on the strand bearing the quencher/fluorophore pair is filled up to final nick in such a way that single base is extended per cycle, similar to how it is achieved in method 1 (see FIG. 8).

Implementation III

Figure 10:
FIG. 10 schematically illustrates an embodiment that relies on cyclical re-annealing of polymerase priming nucleotides and a variant of the same approach that utilizes FRET. SEQ ID NOS: 81-86.

In this implementation, the method comprises rending antibody staining by primer extension with a fluorophore labeled base or otherwise reading a FRET signal generated by energy transfer between a first fluorescent nucleotide added to the primer by primer extension and a second nucleotide that is present in the oligonucleotide FIG. 10. The principles of this method are illustrated in FIG. 9A. The multiplexing is achieved by removing the extension priming oligonucleotide by melting the duplex or by exonuclease and reannealing another primer oligonucleotide which is extendable on a different antibody. A multiplexed version of this method is shown in FIG. 9B. In certain embodiments, the multiplexed implementations may comprise: (a) incubating the planar sample with a plurality of capture agents; (b)

cross-linking the capture agents to the planar sample; (c) extending a primer that is hybridized to the oligonucleotide of a first set of capture agents of the plurality (e.g., wherein the 3' end of the first primer anneals to only the oligonucleotide of the first population), thereby generating a first set of fluorescent signals (which step can be done by adding a labeled nucleotide using polymerase and/or contacting the sample with a labeled oligonucleotide and a ligase); (d) reading the first set of fluorescent signals using fluorescence microscopy; (e) inactivating the fluorescence; (f) extending a primer that is hybridized to the oligonucleotide of a second set of capture agents of the plurality (e.g., wherein the 3' end of the first primer anneals to only the oligonucleotide of the second population), thereby generating a second set of fluorescent signals (which step can also be done by adding a labeled nucleotide using polymerase and/or contacting the sample with a labeled oligonucleotide and a ligase); (g) reading the second set of fluorescent signals using fluorescence microscopy; and (h) comparing the images produce in steps (d) and (g).

In certain embodiments, this method comprises: (a) incubating the planar sample with (i) a first antibody that is linked to a first labeled oligonucleotide and (ii) a second antibody that is linked to a second labeled oligonucleotide, (b) cross-linking the capture agents to the planar sample; (c) hybridizing the first and second labeled oligonucleotides with a first primer, wherein the 3' end of the first primer anneals to only the first labeled oligonucleotide; (d) extending the primer with a fluorescent nucleotide (which step can be done by adding a labeled nucleotide using polymerase and/or contacting the sample with a labeled oligonucleotide and a ligase); (e) reading, by fluorescence microscopy, a FRET signal generated by energy transfer between the label of the first oligonucleotide and the fluorescent nucleotide added to the first primer; (f) inactivating the fluorescent nucleotide added to the first primer; (g) hybridizing the first and second labeled oligonucleotides with a second primer, wherein the 3' end of the second primer anneals to only the second labeled oligonucleotide; (h) extending the second primer with a fluorescent nucleotide; and (i) reading, by fluorescence microscopy, a FRET signal generated by energy transfer between the label of the second oligonucleotide and the fluorescent nucleotide added to the second primer.

FIGS. 9-10 shows an example of this method. The method shown in FIGS. 8-11 has the following steps:

Step 1: The planar sample is stained using a capture agent that is coupled to a single stranded oligonucleotide. The oligonucleotide could be either unlabeled or labeled by FRET acceptor (e.g. Cy5) fluorophore on the 3' end.

Step 2: The binding pattern can be determined by an on-slide hybridization of a complementary probe followed a primer extension reaction in which a fluorescently labeled nucleotide fills in the overhang in the extended strand. In this example (see FIG. 10) the extended base is labeled by a FRET donor (e.g. Cy3), which can increase the signal to noise ratio. If the oligonucleotide that is linked to the capture agent is unlabeled, then the fluorescent emission of the nucleotide that has been incorporated by DNA synthesis can be detected directly, without FRET FIG. 9.

Step 3: The binding pattern of other capture agents can be determined by removing the fluorescence by cleavage of lower strand by exo+ DNA polymerase such as Vent (FIG. 9). Alternatively, the fluorescence can be removed by raising the temperature beyond the melting point of the DNA strands or by one of the de-staining techniques described previously.

Figure 11A:
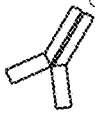
FIGS. 11A-11C shows an anti-CD4 antibody linked to oligonucleotide duplex designed for rendering staining by primer extension (panel A) and data obtained from labeled population of spleen cells in suspension in the absence of polymerase (panel B) and in the presence of polymerase (panel C). SEQ ID NOS: 87 and 88.
Figure 11B:
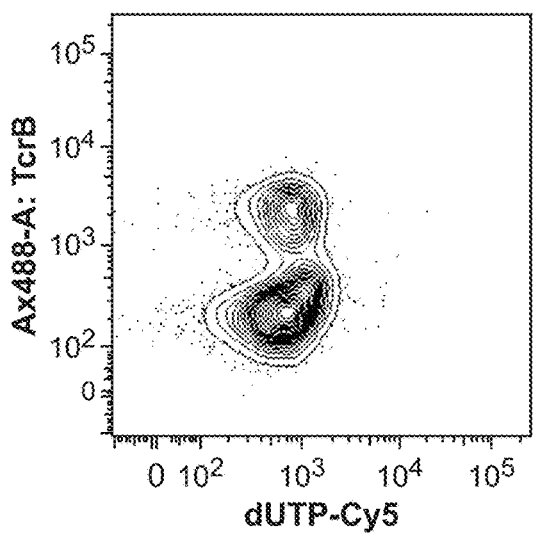
Figure 11C:
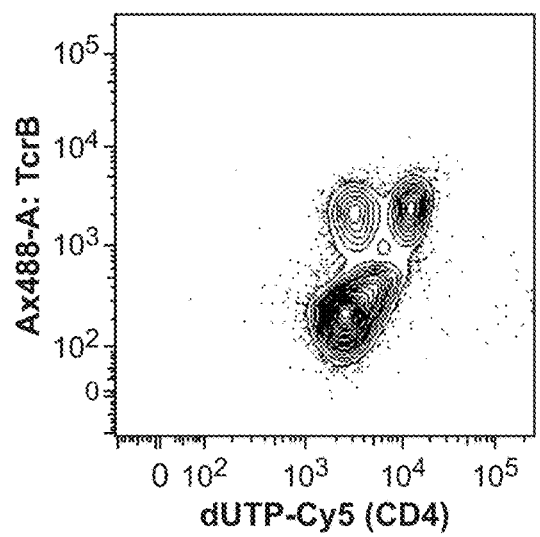
Figure 12A:
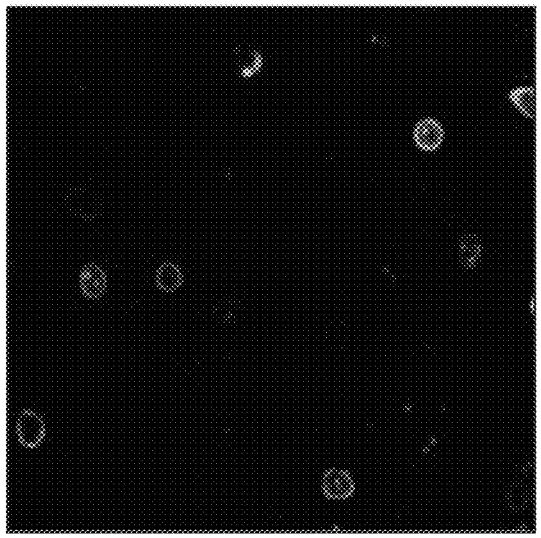
FIGS. 12A-12D shows data obtained from labeling by primer extension a population of spleen cells preattached on the slide. Cells were co-stained with "regular" TCRb-FITC antibody and CD4 antibody linked to oligonucleotide duplex designed for rendering staining by primer extension.
Figure 12B:
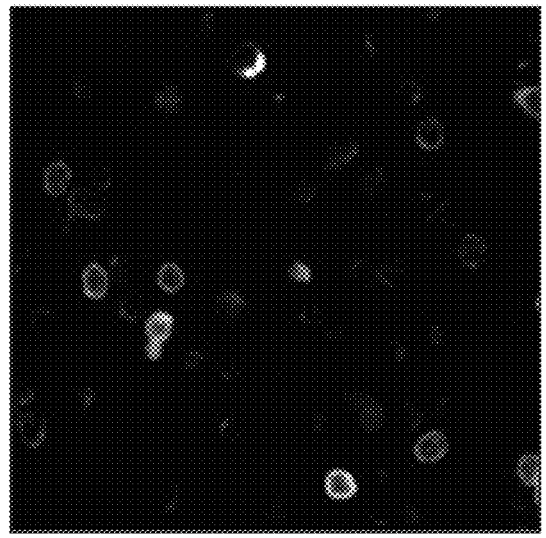
Figure 12C:
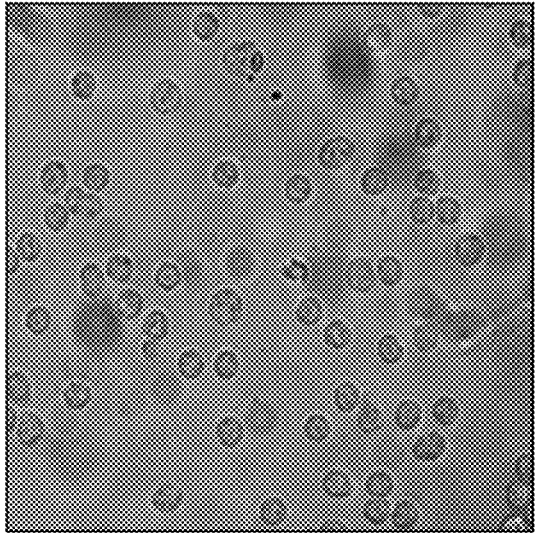
Figure 12D:
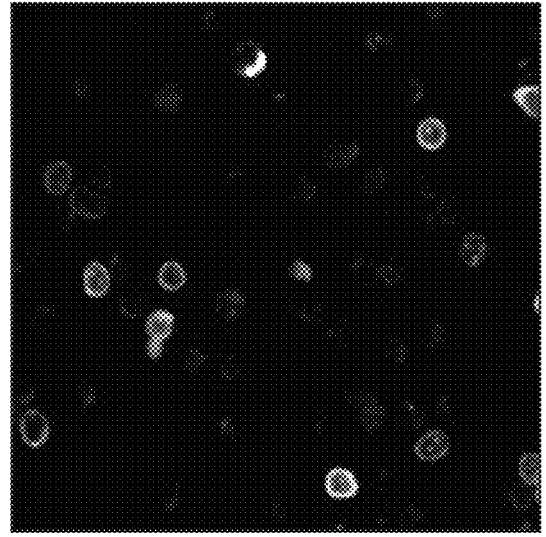

Step 4: Multiplexing can be achieved by staining of the sample with a library of capture agents each labeled with specific oligonucleotides and cycling through Steps 1-3, as described above, each time using a different detection oligonucleotide that is complementary to one of the capture agent-conjugated oligonucleotides. Only duplexes where primers are annealed specifically will be properly extended (FIG. 11). In these embodiments, each primers is designed so that its 3' end hybridizes to only one of the oligonucleotides that are linked to a capture agent.

Further Implementations

As schematically illustrated in FIG. 16, the signal may be amplified using rolling circle amplification. In these embodiments, a capture agent that is linked to an oligonucleotide is hybridized to a padlock probe that hybridizes to the oligonucleotide in such a way that the ends of the padlock probe are ligatably adjacent. In this embodiment, after ligation, the padlock probe (which is now circularized) can be copied by a rolling circle amplification reaction that is primed by the oligonucleotide. This reaction results in a concatamer of the padlock probe that contains several (in many cases hundreds or thousands) of copies of the same sequence in tandem that is linked to the capture agent. The rolling circle amplification product (which is linked to the antibody) can be detected using methods described above and, as illustrated, the signal is amplified because the sequence being detected is repeated. In these embodiments, the (i) the capture agent is linked to a double-stranded nucleic acid that comprises a first strand (i.e., the RCA product) and a second strand (comprising the detection oligonucleotides). Single molecules can be detected using such methods.

Figure 19:
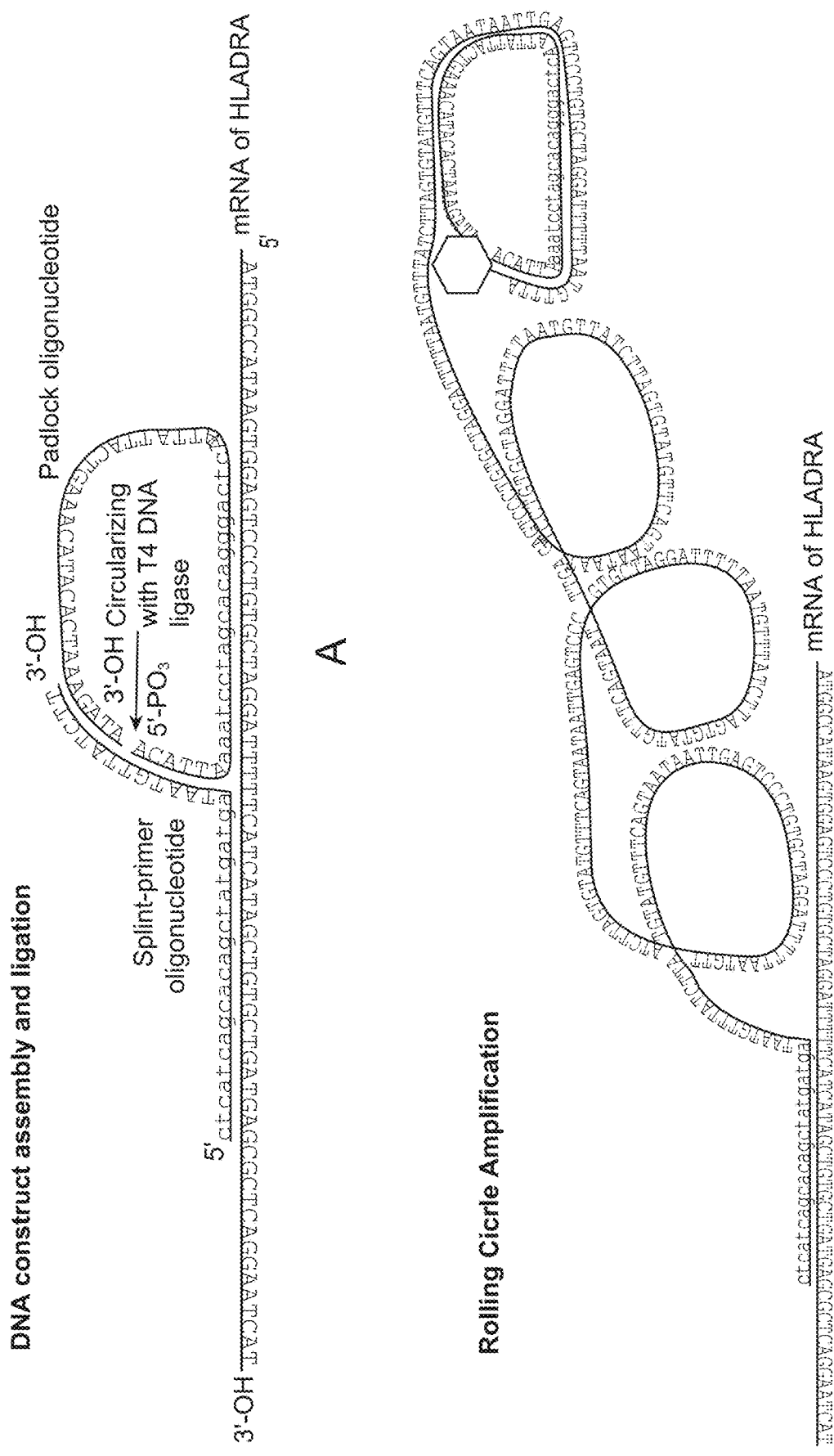
FIG. 19 shows A: A pair of coincidence detection probes is hybridized to the target RNA. Upstream oligonucleotide probe (Splint-primer) serves as a splint for circularization and ligation of the downstream oligonucleotide probe (padlock). Padlock probe contains a detection primer sequence (lilac) followed by the fluorescent nucleotide incorporation site (red) B. Rolling circle amplification is initiated at the 3' end of the upstream probe and creates multiple copies of the reverse-complement of detection primer sequence (lilac). C. Detection primer is annealed to the multiple sites of the amplification product. D. Polymerase reaction with dUTP-Cy5 results incorporations. E-F: small and bright puncta in NALM cells correspond to single HLADRA RNA molecules, which are absent in the negative control Jurkat cells. Large red blobs present in both panels correspond to apoptotic cells that nonspecifically bind the fluorescent nucleotide.

FIG. 19 shows how RNA molecules can be detected using a padlock probe/RCA amplification approach. In this method, the padlock probe hybridizes to the same mRNA as the capture agent (the "splint-primer"), thereby ensuring that the padlock probe circularizes only in the presence of the target RNA. In this embodiment, the splint-primer hybridizes to the target RNA, acts as a splint for the padlock probe, and also acts as a primer for rolling circle amplification, thereby allowing the signal to be amplified in a similar to FIG. 16.

Figure 20:
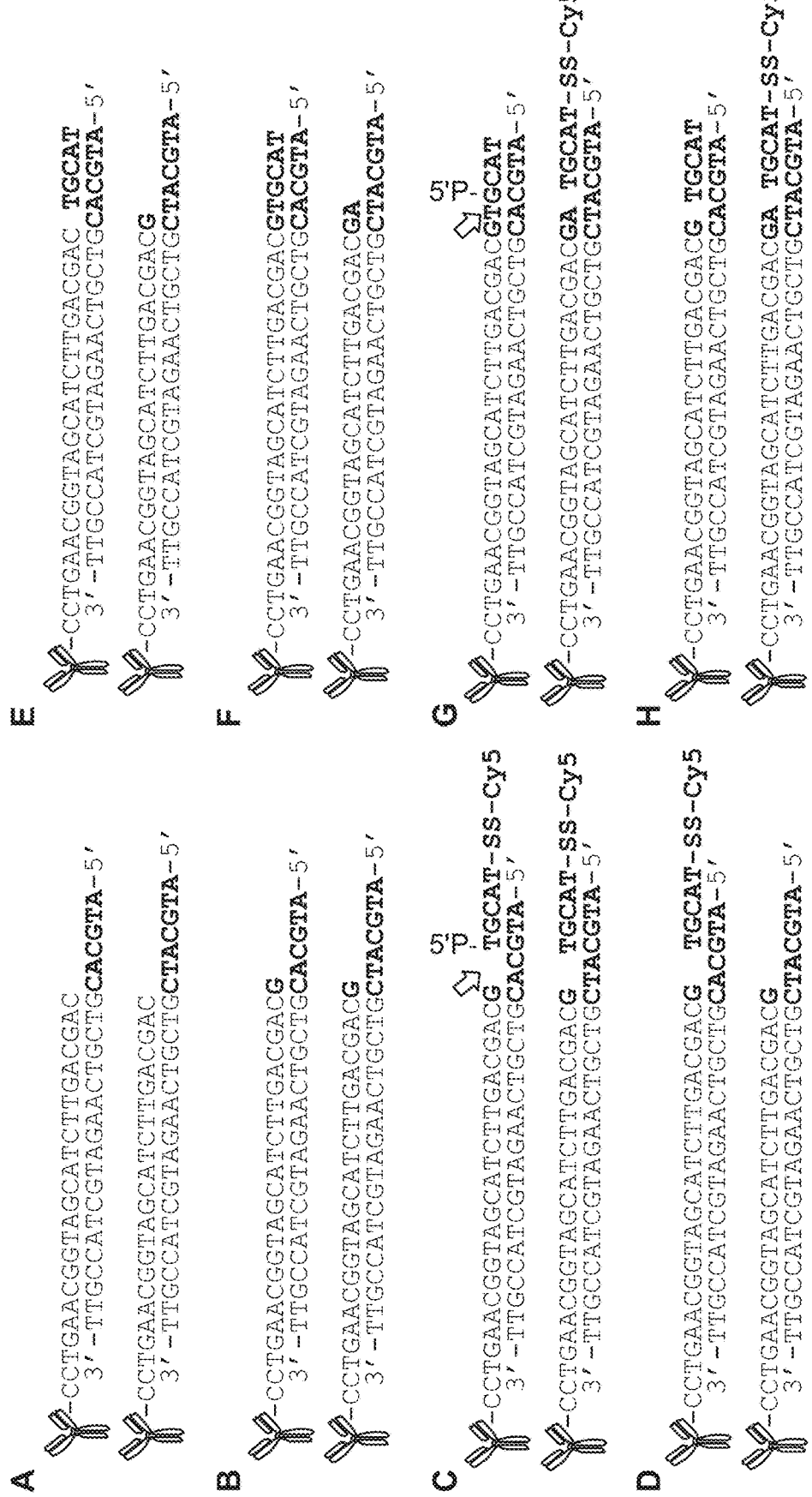
FIG. 20 shows an alternative method that relies on primer extension and the ligation of a short, labeled oligonucleotide. Left side, from top to bottom: SEQ ID NOS: 93-108; right side, from top to bottom: SEQ ID NOS: 109-124.

FIG. 20 shows an alternative method that relies on primer extension and the ligation of a short, labeled oligonucleotide. In this embodiment, ligation of short labeled oligonucleotide to the top strand oligonucleotide only occurs after the overhang has been filed in to a certain point. In embodiments that rely on ligation, a labeled oligonucleotide can be added to either the 3' end or the 5' end of the extendible end.

Utility

The methods and compositions described herein find general use in a wide variety of application for analysis of any planar sample (e.g., in the analysis of tissue sections, sheets of cells, spun-down cells, blots of electrophoresis gels, Western blots, dot-blots, ELISAs, antibody microarrays, nucleic acid microarrays etc).

In particular embodiments, the planar sample may be a section of a tissue biopsy obtained from a patient. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc.

In certain embodiments, capture agents specifically bind to biomarkers, including cancer biomarkers, that may be proteinaceous or a nucleic acid. Exemplary cancer biomarkers, include, but are not limited to carcinoembryonic antigen (for identification of adenocarcinomas), cytokeratins (for identification of carcinomas but may also be expressed in some sarcomas), CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumour identification), CD20 (for identification of B-cell lymphomas) and CD3 (for identification of T-cell lymphomas).

The above-described method can be used to analyze cells from a subject to determine, for example, whether the cell is normal or not or to determine whether the cells are responding to a treatment. In one embodiment, the method may be employed to determine the degree of dysplasia in cancer cells. In these embodiments, the cells may be a sample from a multicellular organism. A biological sample may be isolated from an individual, e.g., from a soft tissue. In particular cases, the method may be used to distinguish different types of cancer cells in FFPE samples.

The method described above finds particular utility in examining planar samples using a plurality of antibodies, each antibodies recognizing a different marker. Examples of cancers, and biomarkers that can be used to identify those cancers, are shown below. In these embodiments, one does not need to examine all of the markers listed below in order to make a diagnosis.

In some embodiments, the method may be employed to detect the location and, optionally, the abundance of DNA molecules and/or RNA molecules in situ. In one exemplary embodiment, the method may be used to detect intracellular RNAs. In these embodiments, the capture agent may be a nucleic acid, and the intracellular location and, optionally, the abundance of RNA molecules (e.g., mRNAs or lncRNAs) may be detected in situ. Such hybridization methods may be adapted from known RNA or DNA FISH methods (see, e.g., Mahadevaiah et al (Methods Mol Biol. 2009 558:433-44), Shaffer et al (PLoS One. 2013 8:e75120) and Pollex et al (Methods Mol. Biol. 2013 1042:13-31), which are incorporated by reference herein.

In some embodiments, the method may involve obtaining an image as described above (an electronic form of which may have been forwarded from a remote location) and may be analyzed by a doctor or other medical professional to determine whether a patient has abnormal cells (e.g., cancerous cells) or which type of abnormal cells are present. The image may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

The compositions and methods described herein can be used to diagnose a patient with a disease. In some cases, the presence or absence of a biomarker in the patient's sample can indicate that the patient has a particular disease (e.g., cancer). In some cases, a patient can be diagnosed with a

| | |
|---|---|
| Acute Leukemia IHC Panel | CD3, CD7, CD20, CD34, CD45, CD56, CD117, MPO, PAX-5, and TdT. |
| Adenocarcinoma vs. Mesothelioma IHC Panel | Pan-CK, CEA, MOC-31, BerEP4, TTF1, calretinin, and WT-1. |
| Bladder vs. Prostate Carcinoma IHC Panel | CK7, CK20, PSA, CK 903, and p63. |
| Breast IHC Panel | ER, PR, Ki-67, and HER2. Reflex to HER2 FISH after HER2 IHC is available. |
| Burkitt vs. DLBC Lymphoma IHC panel | BCL-2, c-MYC, Ki-67. |
| Carcinoma Unknown Primary Site, Female (CUPS IHC Panel - Female) | CK7, CK20, mammaglobin, ER, TTF1, CEA, CA19-9, S100, synaptophysin, and WT-1. |
| Carcinoma Unknown Primary Site, Male (CUPS IHC Panel - Male) | CK7, CK20, TTF1, PSA, CEA, CA19-9, S100, and synaptophysin. |
| GIST IHC Panel | CD117, DOG-1, CD34, and desmin. |
| Hepatoma/Cholangio vs. Metastatic Carcinoma IHC Panel | HSA (HepPar 1), CDX2, CK7, CK20, CAM 5.2, TTF-1, and CEA (polyclonal). |
| Hodgkin vs. NHL IHC Panel | BOB-1, BCL-6, CD3, CD10, CD15, CD20, CD30, CD45 LCA, CD79a, MUM1, OCT-2, PAX-5, and EBER ISH. |
| Lung Cancer IHC Panel | chromogranin A, synaptophysin, CK7, p63, and TTF-1. |
| Lung vs. Metastatic Breast Carcinoma IHC Panel | TTF1, mammaglobin, GCDFP-15 (BRST-2), and ER. |
| Lymphoma Phenotype IHC Panel | BCL-2, BCL-6, CD3, CD4, CD5, CD7, CD8, CD10, CD15, CD20, CD30, CD79a, CD138, cyclin D1, Ki67, MUM1, PAX-5, TdT, and EBER ISH. |
| Lymphoma vs. Carcinoma IHC Panel | CD30, CD45, CD68, CD117, pan-keratin, MPO, S100, and synaptophysin. |
| Lymphoma vs. Reactive Hyperplasia IHC Panel | BCL-2, BCL-6, CD3, CD5, CD10, CD20, CD23, CD43, cyclin D1, and Ki-67. |
| Melanoma vs. Squamous Cell Carcinoma IHC Panel | CD68, Factor XIIIa, CEA (polyclonal), S-100, melanoma cocktail (HMB-45, MART-1/Melan-A, tyrosinase) and Pan-CK. |
| Mismatch Repair Proteins IHC Panel (MMR/Colon Cancer) | MLH1, MSH2, MSH6, and PMS2. |
| Neuroendocrine Neoplasm IHC Panel | CD56, synaptophysin, chromogranin A, TTF-1, Pan-CK, and CEA (polyclonal). |
| Plasma Cell Neoplasm IHC Panel | CD19, CD20, CD38, CD43, CD56, CD79a, CD138, cyclin D1, EMA, kappa, lambda, and MUM1. |
| Prostate vs. Colon Carcinoma IHC Panel | CDX2, CK 20, CEA (monoclonal), CA19-9, PLAP, CK 7, and PSA. |
| Soft Tissue Tumor IHC Panel | Pan-CK, SMA, desmin, S100, CD34, vimentin, and CD68. |
| T-Cell Lymphoma IHC panel | ALK1, CD2, CD3, CD4, CD5, CD7, CD8, CD10, CD20, CD21, CD30, CD56, TdT, and EBER ISH. |
| T-LGL Leukemia IHC panel | CD3, CD8, granzyme B, and TIA-1. |
| Undifferentiated Tumor IHC Panel | Pan-CK, S100, CD45, and vimentin. | disease by comparing a sample from the patient with a sample from a healthy control. In this example, a level of a biomarker, relative to the control, can be measured. A difference in the level of a biomarker in the patient's sample relative to the control can be indicative of disease. In some cases, one or more biomarkers are analyzed in order to diagnose a patient with a disease. The compositions and methods of the disclosure are particularly suited to identifying the presence or absence of, or determining expression levels, of a plurality of biomarkers in a sample.

In some cases, the compositions and methods herein can be used to determine a treatment plan for a patient. The presence or absence of a biomarker may indicate that a patient is responsive to or refractory to a particular therapy. For example, a presence or absence of one or more biomarkers may indicate that a disease is refractory to a specific therapy and an alternative therapy can be administered. In some cases, a patient is currently receiving the therapy and the presence or absence of one or more biomarkers may indicate that the therapy is no longer effective.

In any embodiment, data can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the image may be analyzed by an MD or other qualified medical professional, and a report based on the results of the analysis of the image may be forwarded to the patient from which the sample was obtained.

In some cases, the method may be employed in a variety of diagnostic, drug discovery, and research applications that include, but are not limited to, diagnosis or monitoring of a disease or condition (where the image identifies a marker for the disease or condition), discovery of drug targets (where the a marker in the image may be targeted for drug therapy), drug screening (where the effects of a drug are monitored by a marker shown in the image), determining drug susceptibility (where drug susceptibility is associated with a marker) and basic research (where is it desirable to measure the differences between cells in a sample).

In certain embodiments, two different samples may be compared using the above methods. The different samples may be composed of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment, the sample pair is represented by undifferentiated cells, e.g., stem cells, and differentiated cells.

The images produced by the method may be viewed side-by-side or, in some embodiments, the images may be superimposed or combined. In some cases, the images may be in color, where the colors used in the images may correspond to the labels used.

Cells any organism, e.g., from bacteria, yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

Computer Systems

Figure 21:
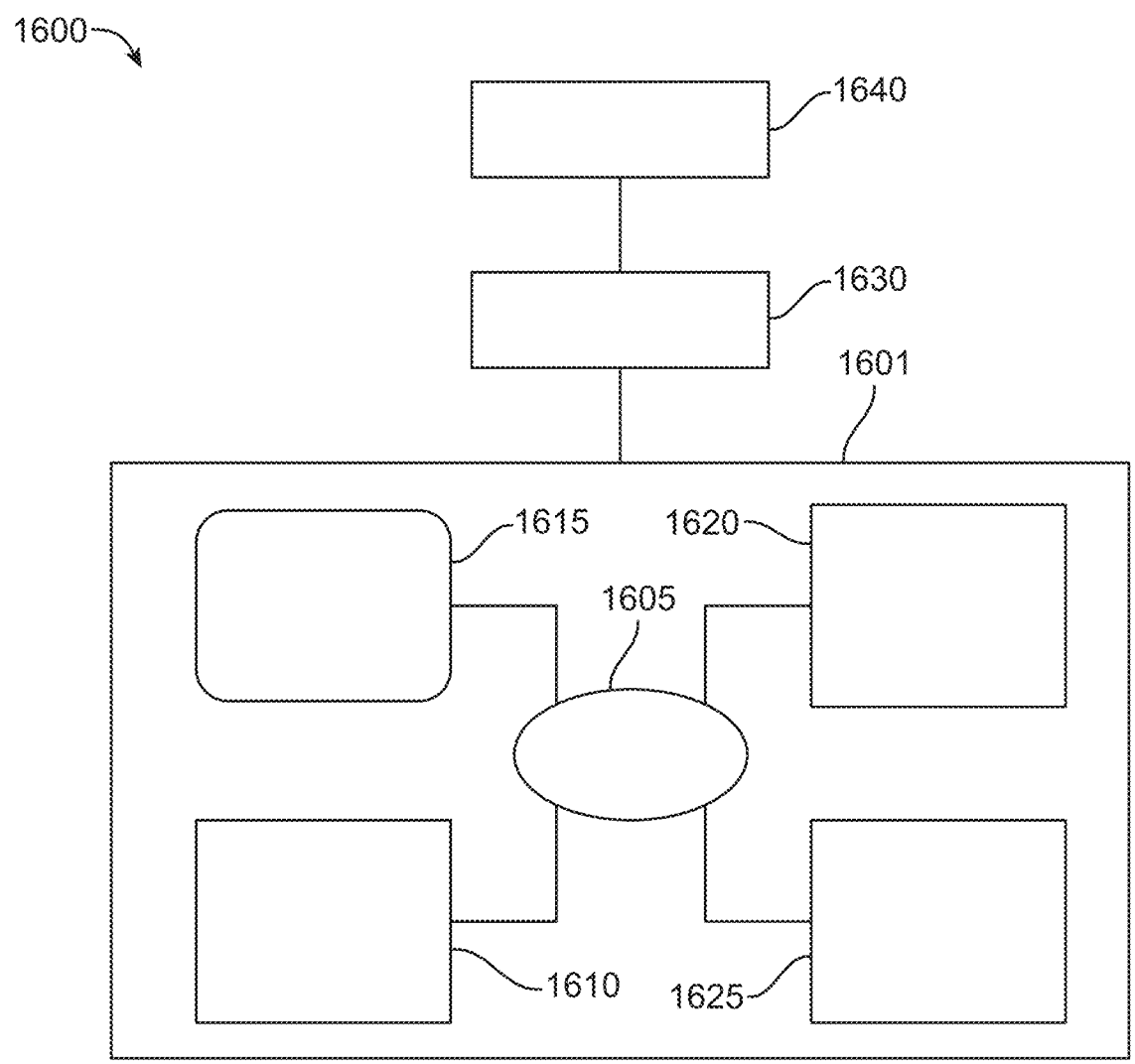
FIG. 21 depicts a system to enable a user to detect, analyze, and process images of samples.

The invention also provides a computer system that is configured to implement the methods of the disclosure. The system can include a computer server ("server") that is programmed to implement the methods described herein. FIG. 21 depicts a system 1600 adapted to enable a user to detect, analyze, and process images of samples. The system 1600 includes a central computer server 1601 that is programmed to implement exemplary methods described herein. The server 1601 includes a central processing unit (CPU, also "processor") 1605 which can be a single core processor, a multi core processor, or plurality of processors for parallel processing. The server 1601 also includes memory 1610 (e.g. random access memory, read-only memory, flash memory); electronic storage unit 1615 (e.g. hard disk); communications interface 1620 (e.g. network adaptor) for communicating with one or more other systems; and peripheral devices 1625 which may include cache, other memory, data storage, and/or electronic display adaptors. The memory 1610, storage unit 1615, interface 1620, and peripheral devices 1625 are in communication with the processor 1605 through a communications bus (solid lines), such as a motherboard. The storage unit 1615 can be a data storage unit for storing data. The server 1601 is operatively coupled to a computer network ("network") 1630 with the aid of the communications interface 1620. The network 1630 can be the Internet, an intranet and/or an extranet, an intranet and/or extranet that is in communication with the Internet, a telecommunication or data network. The network 1630 in some cases, with the aid of the server 1601, can implement a peer-to-peer network, which may enable devices coupled to the server 1601 to behave as a client or a server. A microscope can be a peripheral device 1625 or a remote computer system 1640.

The storage unit 1615 can store files, such as individual images, time lapse images, data about individual cells, data about individual biomarkers, images showing a pattern of binding of capture agents to a sample, or any aspect of data associated with the invention. The data storage unit 1615 may be coupled with data relating to locations of cells in a virtual grid.

The server can communicate with one or more remote computer systems through the network 1630. The one or more remote computer systems may be, for example, personal computers, laptops, tablets, telephones, Smart phones, or personal digital assistants.

In some situations the system 1600 includes a single server 1601. In other situations, the system includes multiple servers in communication with one another through an intranet, extranet and/or the Internet.

Methods as described herein can be implemented by way of machine (e.g., computer processor) computer readable medium (or software) stored on an electronic storage location of the server 1601, such as, for example, on the memory 1610, or electronic storage unit 1615. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610. Alternatively, the code can be executed on a second computer system 1640.

Aspects of the systems and methods provided herein, such as the server 1601, can be embodied in programming Various aspects of the technology may be thought of as "products" or "articles of manufacture" typically in the form of machine (or processor) executable code and/or associated data that is carried on or embodied in a type of machine readable medium (e.g., computer readable medium). Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

The results of the sample staining or labeling can be presented to a user with the aid of a user interface, such as a graphical user interface.

Kits

In some aspects, the disclosure herein provides for kits. The kits can comprise any number of compositions to perform the methods of the disclosure, each of which have been described herein. For example, a kit may comprise at least one capture agent. The capture agent can be an antibody, an aptamer, or an oligonucleotide probe. The capture agent can be custom-made to specifically bind to a desired target. For example, a user may custom-order one or more capture agents to be included in the kit. In some cases, the capture agents can be sold separately. The capture agents can specifically bind to a target molecule of interest. Additionally or alternatively, capture agents can be ordered as a panel (i.e., a pre-determined selection of capture agents). The panel can be specific for a particular type of disease (e.g., cancer) or a particular sub-type of a disease (e.g., colon cancer). A kit of the disclosure can also include one or more oligonucleotides. The oligonucleotides can comprise a first strand and a double strand, as described herein. The oligonucleotides can be provided as single-stranded oligonucleotides or as double-stranded oligonucleotides. In the latter case, the kit can include reagents and/or instructions for annealing the first strand and the second strand of oligonucleotides to produce double-stranded oligonucleotides. The single- or double-stranded oligonucleotides can be conjugated to the capture agents or can be provided unconjugated. In the latter case, reagents can be included in the kit for conjugating the double-stranded oligonucleotides to the capture agents (e.g., reagents to perform Click chemistry). In some cases, the kit may provide a plurality of oligonucleotides wherein each of the first strands is the same and each of the second strands is different. The kit can further comprise any nucleotide mixture disclosed herein. Nucleotide mixtures can comprise any combination of fluorescent nucleotides, unlabeled nucleotides, reversible terminator nucleotides, and the like. Generally, the nucleotide mixture provided in the kit will be compatible with the provided oligonucleotides. The kit can further comprise, without limitation, a polymerase for performing primer extension, a reagent for inactivating a signal (e.g., TCEP), a blocking solution (e.g., iodoacetamide solution), and any buffer or solution suitable to perform the methods herein. The kit can comprise any reagent for preparing a sample for labeling such as a fixative (e.g., formaldehyde) or reagents for embedding a sample (i.e., paraffin wax). The kit can further comprise a control sample for comparison with a test sample. The control sample can be a healthy sample or a diseased sample. The control sample may be matched to the tissue or cell type under investigation or to the disease being studied. In some cases, the control sample may be a positive control or a negative control.

EMBODIMENTS

A method for analyzing a planar sample is provided. In certain embodiments, the method comprises: (a) incubating the planar sample with a capture agent under conditions by which the capture agent specifically binds to complementary sites in the planar sample, wherein: (i) the capture agent is linked to a double-stranded oligonucleotide that comprises a first strand and a second strand; (ii) the capture agent is linked to a double-stranded oligonucleotide by the 5' end of the first strand; and (iii) the 3' end of the first strand is recessed relative to the 5' end of the second strand, thereby producing an overhang; (b) crosslinking the capture agent to planar sample; (c) contacting the planar sample with a polymerase and a nucleotide mix, thereby adding one or more nucleotides to the overhang; and/or contacting the planar sample with a mixture of short oligonucleotides, some of which may be labelled or not, and a DNA ligase and (d) reading a fluorescent signal generated by addition of the one or more nucleotides to the overhang using fluorescence microscopy, thereby producing an image showing the pattern of binding of the capture agent to the planar sample. In some embodiments, after the sample has been read, this method may involve removing the fluorescent moiety and deprotecting an added fluorescent nucleotide, thereby allowing the method to be repeated.

In any embodiment, step (c) may comprise contacting the planar sample with a polymerase and a nucleotide mix that comprises a fluorescent nucleotide, thereby adding the fluorescent nucleotide to the overhang, or contacting to planar sample with one or more fluorescently labeled oligonucleotides, thereby adding a fluorescently labeled oligonucleotide to the overhang; and step (d) comprises reading a fluorescent signal generated by addition of the fluorescent nucleotide or oligonucleotide to the overhang. In this embodiment, the fluorescent signal may be: emitted directly from the added nucleotide or oligonucleotide, a FRET signal generated by energy transfer between two fluorescent nucleotides that are added to the overhang or a FRET signal generated by energy transfer between a first fluorescent nucleotide added to overhang and a second fluorescent nucleotide that is present in the second strand.

In some embodiments, extension of the first strand removes a quencher from a quenched fluorescently labeled oligonucleotide that is hybridized to the second strand, downstream from the first strand.

In any embodiment, the sample may be a formalin-fixed, paraffin-embedded (FFPE) section.

Also provided herein is a capture agent that is linked to a double-stranded oligonucleotide, wherein: (i) the double-stranded oligonucleotide comprises a first strand and a second strand; (ii) the capture agent is linked to the 5' end of the first strand; and (iii) the 3' end of the first strand is recessed relative to the 5' end of the second strand, thereby producing an overhang or (iiii) the 5' end is recessed relative to the 3' end of the second strand, there producing and overhang Also provided herein is a capture agent composition comprising a plurality of capture agents that recognize different complementary sites, wherein: each of the capture agents is linked to a double-stranded oligonucleotide that comprises a first strand and a second strand; the capture agents are linked to a double-stranded oligonucleotide by the 5' end of first strand; the 3' end of the first strand in each of the double-stranded oligonucleotides is recessed relative to the 5' end of the second strand, thereby producing an overhang; and the overhang is different for each of the capture agents. Alternatively, the 5' end is recessed relative to the 3' end of the second strand, there producing and overhang that is specific to each capture agent. In this embodiment, the sequence of the first strand may be the same for each of the capture agents; and the sequence of the second strand may be different for each of the capture agents.

In these embodiments, the overhangs may be of the formula $3'-N_{4n}N_1/N_2/N_3$, wherein $N_1$, $N_2$, $N_3$ and $N_4$ are different nucleotides selected from G, A, T and C and n is 1 or more, or the formula $3'-YN_1/N_2-5'$, optionally followed by short stretch of random nucleotides on the 5' end to increase the overall polymerase residence on the DNA duplex, wherein Y is composed of alternating stretches of bases $N_3$ and $N_4$, and wherein $N_1$, $N_2$, $N_3$ and $N_4$ are different nucleotides selected from G, A, T and C.

A method for analyzing a tissue sample is also provided. In these embodiments, the method may comprise (a) incubating a planar sample with a capture agent composition of a prior embodiment under conditions by which the capture agents specifically bind to sites in the planar sample; (b) crosslinking capture agents to planar sample; (c) contacting the planar sample with a polymerase and either an incomplete nucleotide mix or a nucleotide mix that comprises a reversible terminator nucleotide and/or a ligase and a labeled oligonucleotide; and (d) reading, using fluorescence microscopy, a fluorescent signal generated by addition a nucleotide to some but not all of the capture agents.

In this embodiment, the method may comprise: (c) contacting the planar sample with a polymerase and: (i) a nucleotide mix that comprises fluorescent nucleotides that are complementary to $N_1$, $N_2$ and $N_3$ and a reversible terminator nucleotide that is complementary to $N_4$ or (ii) a nucleotide mix that comprises fluorescent nucleotides that are complementary to $N_1$, and $N_2$, an unlabeled nucleotide that is complementary to $N_3$, and no nucleotide that is complementary to $N_4$, thereby adding fluorescent nucleotides onto the double-stranded oligonucleotides of some but not all of the capture agents. This step can also be done by ligation, i.e., by contacting the planar sample with a labeled oligonucleotide (or a mixture of the same), where addition of the labeled oligonucleotide depends on the underlying sequence of the overhang. This method also comprises: (d) reading, using fluorescence microscopy, a fluorescent signal generated by addition of a fluorescent nucleotide to some but not all of the capture agents. In these embodiments, the overhangs may be of the formula $3'-N_{4n}/N_2/N_3$, wherein $N_1$, $N_2$, $N_3$ and $N_4$ are different nucleotides selected from G, A, T and C and n is 1 or more; and step (c) comprises contacting the planar sample with a polymerase and a nucleotide mix that comprises fluorescent nucleotides that are complementary to $N_1$, $N_2$ and $N_3$ and a reversible terminator nucleotide that is complementary to $N_4$. This step can also be implemented by addition of a labeled oligonucleotide using a ligase. In these embodiments, the method may comprise (e) inactivating the fluorescent signal, deprotecting the reversible terminator nucleotide and blocking the sample; and (f) repeating steps (c) and (d). In some cases, step (f) may comprise repeating steps (c), (d) and (e) multiple times. Alternatively, the overhangs may be of the formula 3'-$YN_1$/$N_2$-5', optionally followed by short stretch of random nucleotides on the 5' end to increase the overall polymerase residence on the DNA duplex, wherein Y is composed of alternating stretches of bases $N_3$ and $N_4$, and wherein $N_1$, $N_2$, $N_3$ and $N_4$ are different nucleotides selected from G, A, T and C. In these embodiments, the method may further comprise (e) inactivating the fluorescent signal and contacting the planar sample with a polymerase and an unlabeled nucleotide that is complementary to $N_4$; and (f) repeating steps (c) and (d). In some cases, step (f) may comprise repeating steps (c), (d) and (e) multiple times.

In some embodiments, the double-stranded oligonucleotides each comprise a fluorescently labeled oligonucleotide hybridized to the second strand downstream from first strand, wherein the fluorescently labeled oligonucleotide comprises a quencher and extension of the first strand removes the quencher from some but not all of the quenched fluorescently labeled oligonucleotides, thereby generating a fluorescent signal for some but not all of the capture agents.

Example I

Materials and Methods

Spleen cells fixed in 2% formaldehyde, permeablized and stored in methanol at −80 were spun from methanol, resuspended and washed with buffer 4 (10 mM Tris & 0.5, 10 mM MgCl2, 150 mM NaCl, 0.1% Triton x100) for 5 min on a rotator. To block against non-specific binding of ab-oligonucleotide complexes cells were further spun, resuspended in 1 ml PBS, 0.5% BSA (SM) and supplemented up to additional 0.5M NaCl (0.9 ml SM+100 ul 5M NaCl). 20 ul of sheared ssDNA (10 mg/ml), 50 ul of mouse IgG (10 mg/ml) and 20 ul of 0.5M EDTA were further added to 1 ml of cells and the mix was incubated for 30 min on a rotator. For staining cells were redistributed into 30 250 ul tubes (PCR strip tubes is a convenient choice for that matter) with premade antibody/oligonucleotide complexes (0.2 ug of CD45-146 complex was annealed with 1 ul of specific oligonucleotide (147 etc) per tube 30 min at 40 C) and incubated for 1 h with rotation. Cells were washed in (PBS, 0.1% Triton 0.5M salt 5 mM EDTA) twice, placed on poly-lysine treated glass coverslips, allowed to stand/attach for 10 min and further fixed with 5 mM BS3 (7.4 mg per 4 ml) in PBS, 0.1% Triton, 0.5M NaCl, 5 mM EDTA for 1 hour.

Staining was rendered in cycles. For odd cycles (1, 3, 5, 7, 9, 11, 13, 15) coverslips were incubated for 2 min in dG/dU mix (150 nM dG, 150 nM dUssCy5, 150 nM dCssCy3, 25 ul NEB exo– Klenow per ml in buffer #4 (10 mM Tris 7.5, 0.5M NaCl, 0.1% Triton x100, 10 mM MgCl2)), washed twice with 405 (buffet #4 supplemented up to 0.65M NaCl); and imaged by confocal microscopy. Following imaging the fluorophores were cleaved off cells by incubation in 50 mM TCEP for 2 min in buffer 405E (10 mM Tris 7.5, 0.5M NaCl, 0.1% Triton x100, 5 mM EDTA). After cleavage cells were washed in 405E and blocked for for 1 min in iodoacetamide solution (FRESHLY made 100 mM iodoacetamide in buffer 405E). The blocking solution was removed by two washes with buffer #4. Before proceeding to next cycle cells were again imaged by confocal microscopy. Even cycles (2, 4, 6, 8, 10, 12, 14) were performed same as odd cycles except for substitution of dG with dA in labeling step and extension of cleavage to 4 min at room temperature.

Preliminary Data.

To explore the possibility of in situ staining by primer extension expression of CD4 was visualized in mouse spleen cells in suspension (FIG. 11) or immobilized on a slide. (FIG. 12). To visualize the T lymphocytes spleen cells were co-stained with conventional TcrB-Ax488 antibody. Both samples were stained with CD4 antibody conjugated to oligonucleotide duplex as in (FIG. 11 A). No Klenow polymerase was added in control samples which results in no separation of TcrB positive T-cells into subsets (FIG. 11 B). When Klenow polymerase was supplied. CD4 positive T-cells could be observed as a Cy5 positive subset of TcrB positive T-cells (FIG. 11 C and FIG. 12). Clear membrane staining pattern was observed by confocal imaging of cells stained on-slide (FIG. 12 A). Taken together this data shows that on-slide primer extension reaction can be used for rendering the capture agent binding pattern FIG. 11. Flow cytometric analysis of mouse spleen cells stained by primer extension. Mouse spleen cells were fixed and permeabilized with methanol as done for intracellular protein staining. Cells were co-stained with conventional TcrB-Ax488 antibody and CD4 antibody conjugated to oligonucleotide duplex as in (A). After staining cells were either incubated in extension buffer with dUTP-Cy5 without (B) or with (C) Klenow exo⁻ polymerase. Note that TcrB positive T-cells in (B) are indicated by Ax-488 staining. Dependent upon the addition of Klenow, TcrB positive CD4 positive T-cells are seen as a Cy5 positive subset of TcrB positive T-cells in (C).

FIG. 12. On-slide analysis of mouse spleen cells stained by primer extension. Mouse spleen cells were fixed and permeabilized with methanol as done for intracellular protein staining. Cells were attached to poly-Lysine coated slide and co-stained with conventional TcrB-Ax488 antibody and CD4 antibody conjugated to oligonucleotide duplex as in FIG. 12 A. After staining, cells were incubated in extension buffer with dUTP-Cy5 Klenow exo⁻ polymerase and visualized by confocal microscopy. Shown are DIC image in C, Cy5 channel in A, Ax488 channel in B and merged Ax488 and Cy5 channels in D. Note that only a subset of TcrB-Ax488 positive T-cells in (B) are rendered Cy5 positive CD4 positive T-cells by primer extension as seen in (A). The membrane pattern of CD4 points to specificity of staining by primer extension as it takes place at a particular expected subcellular localization.

Figure 14:
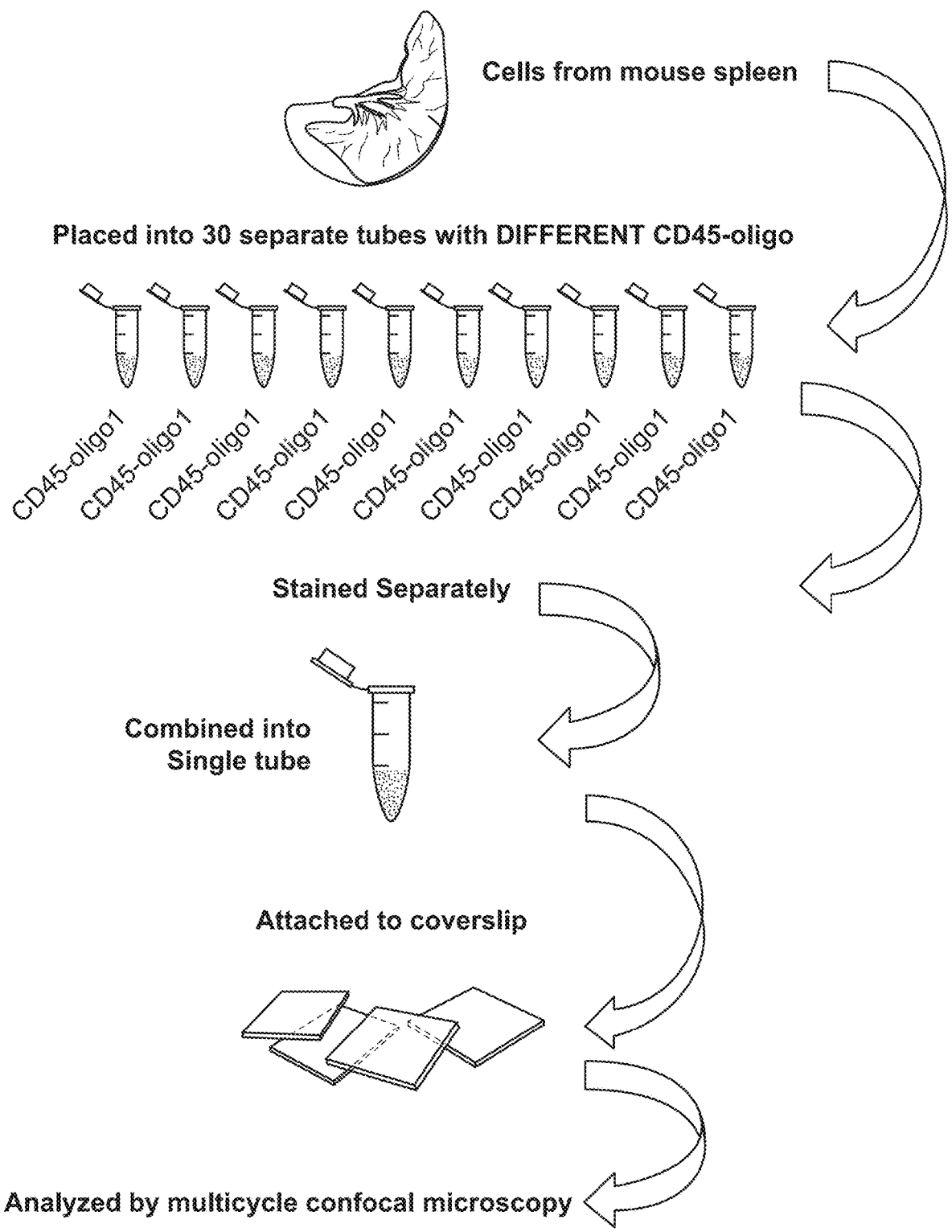
FIG. 14 shows a schematic diagram of an experiment testing multiplexed staining by "missing base" approach. Mouse spleen samples were barcoded by pan-leukocytic CD45 antibody conjugated to per sample specific oligonucleotide duplexes. Samples were mixed after staining and mixture was resolved by sequential rendering of CD45-oligonucleotide variants.

To prove the possibility of multiplexed detection of several antigens by primer extension, the expression of CD4 and CD8 was co-analyzed in mouse spleen cells immobilized on a slide by Method 1 and, specifically, the multiplexing approach based on "reversible terminators". The cells were simultaneously stained by CD4 and CD8 antibodies conjugated to oligonucleotide duplexes as in (FIG. 14, A) simultaneously. Two cycles of rendering were performed such that CD8 was visualized in the first cycle (FIG. 14, C) and CD4 in the second (FIG. 14, D). Cells were counterstained with TcrB-Ax488 to delineate T-lynphocytes in the spleen cells. As expected CD4 positive cells were rendered as a subset of TcrB positive T-cells mutually exclusive with CD8-positive subset of T-lymphocytes (FIG. 14, A-D). The data suggests that rendering antibody staining by polymer (DNA-duplex) extension is an approach enabling sensitive antigen detection and multiplexing.

FIG. 13. Two cycle analysis of CD4 and CD8 staining in mouse spleen using Method 1 with reversible terminators. Mouse spleen cells were fixed and permeabilized with methanol as done for intracellular protein staining. Cells were attached to poly-Lysine coated slide and co-stained with conventional TcrB-Ax488 antibody and a mixture of CD4 and CD8 antibodies conjugated to oligos as indicated on (A). For the first cycle of staining the cells were incubated in extension buffer with Illumina reversible terminators and Klenow exo⁻ polymerase and visualized by confocal microscopy (C). Following the imaging after the first cycle, cells were destained by Illumina cleavage buffer containing TCEP. Following destaining-terminator reactivation, cells were again incubated in extension buffer with Illumina reversible terminators and Klenow exo⁻ polymerase and visualized by confocal microscopy (D) Note that four T-cells identified by high levels of TcrB and marked by four white arrows on (B). It becomes evident after the first cycle of staining that two of these cells are CD8a positive (marked by purple arrows on (C). Second cycle of staining reveals that the other two cells are CD4 positive (marked by green arrows on (D). The expected mutual exclusivity of CD4 and CD8a as well as membrane pattern of incorporated labeled nucleotide further supports the specificity of staining by cycles of primer extension.

The "missing base" multiplexing approach was tested on a model of heterogeneous tissue containing multiplicity of distinct cellular subsets (FIG. 14). To this end leukocytes from homogenized mouse spleen were divided into 30 samples. 30 different versions of CD45 were made by conjugating purified CD45 to common upper strand oligonucleotide and then separately annealing 30 different lower strand oligonucleotides designed to create overhangs that can be sequentially rendered (two per cycle) in the multiplexed version of "missing base approach". The samples were individually stained (barcoded) by 30 CD45 antibody conjugates, the unbound CD45 was washed off the barcoded samples were mixed and attached to a slide. The staining of this mixture of pseudotyped cells was rendered by "missing base" approach. Six first cycles (12 populations, 2 red and green per cycle) as well as inactivation of fluorescence by cleaving the fluorophore off the modified base by TCEP between the cycles is shown on FIG. 15. As can be seen no same two cells are stained in each cycle and between the cycles proving that on-cell primer extension reliably renders the specific antibody staining.

In order to test the performance and multiplexing capacity of "missing base" method the following model approach was employed, as shown in FIGS. 14 and 15. Mouse CD45 antibody was chemically conjugated to an "upper strand" oligonucleotide (oligonucleotide id-146). The conjugated antibody was further divided and separately annealed (by 30 min co-incubation at 40 C) to 30 different "lower strand" oligonucleotides—thus effectively creating 30 different species of CD45 antibody. The 30 "lower strand" oligonucleotides were designed in accordance with "missing base" strategy and in addition in such a way that 2 antibodies could be rendered per cycle using two bases (dUTP and dCTP) reversibly (through s-s linker) coupled with distinct fluorophores (Cy5 and Cy3). 30 samples of homogenized mouse spleen have been "barcoded" with these CD45-oligonucleotide duplex complexes such way that majority of cells in each sample became labeled with a particular CD45-upper/lower oligonucleotide combination. Following staining and washing the samples were combined to mimic a tissue with 30 different cellular subsets. The mixture was smeared on a slide and rendered by cycling staining with a "missing base" approach such that two subsets per staining cycle were co-visualized on different imaging channels.

Example 2

Antibody Signal Amplification In Situ with Rolling Circle Amplification

Materials and Methods

Rat anti-mouse B220 antibody conjugate to oligonucleotide 146v2 was prepared as described. The conjugate were hybridized to a padlock oligonucleotide (PatgctaccgttAAT-TATTACTGAAACATACACTAAAGATAACATTA ttctgcaag: SEQ NO:125) that is designed to form a circular hybrid on 146v2. Mouse spleen cells were stained with either of the conjugates and then those cells that were stained with the padlock construct were incubated with T4 RNA ligase (NEB) in manufacturer's ligation buffer at 37 C for 1 hour and then with phi29 polymerase and dNTP mix for 15 minutes. Cells were washed 3 times with PBS and then incubated with 10 nM RCA product detection oligonucleotide (TGAAACATACACTAAAGA; SEQ ID NO:126) for 10 minutes. After that, cells were incubated with fluorescent dUTP-Cy5 (Jena Biosciences) was incorporated into the cells by incubating with 200 nM dUTP-Cy in buffer #4 and 1 ul of exo– Klenow polymerase (Thermo Scientific). An aliquot of cells was left out and not subject to the rolling circle amplification (RCA) step and then used as a reference to assess the effect of RCA on staining.

Results

The efficiency of rolling circle amplification of multiplexing DNA barcode attached to the antibody for enhancing antibody staining was tested. A special antibody-DNA conjugate based on anti-B220 antibody that contained a circularized 'padlock' oligonucleotide annealed to the linker (146v2) oligonucleotide hybrid was assembled and mouse cells were stained with it. After staining, the padlock oligonucleotide was ligated with T4 ligase and amplified using the rolling circle protocol with phi29 polymerase, resulting in a long repetitive DNA stretch attached to each antibody that contained the repetitive sequence complementary to the detection primer. After annealing of the primer, multiple molecules of dUTP-Cy5 could be incorporated into the amplified DNA molecule, due to its repetitive nature. FIG. 16 panels A-E schematically illustrate this method. FIG. 16 panels F-G shows that the cells staining with the rolling circle amplification is much stronger than without it.

Example 3

Co-Detecting 22 Antigens on Dispersed Spleen Cells

Materials and Methods

Antibody conjugates were prepared using the following protocol. Antibodies were subject to partial reduction of disulfide by 30 min incubation at room temperature with TCEP (final concentration 1 mM) in PBS pH 7.4. The antibodies were purified from TCEP by buffer exchange on BioGel P-30 spin-columns saturated with conjugation buffer (PBS pH 7.0). Oligonucleotide 146v2 (5' Maleimide-ATAGCAGTCCAGCCGAACGGTA GCATCTTGCAGAA; SEQ ID NO: 27) bearing a protected maleimide group were ordered from Trilink Inc. To prepare for covalent crosslinking to antibodies per instruction from manufacturer the maleimide group residing on an oligonucleotide was de-protected/activated by Adler reaction (4 h at 90 C in toluene). Toluene was removed from the oligonucleotide by several washes in absolute ethanol. Activated oligonucleotides were dissolved in conjugation buffer and mixed with reduced antibodies at a molar ratio of 50:1. Sodium Chloride was added to conjugation reaction to final concentration of 1M. Conjugation reaction was allowed to proceed for 1 h. To remove the unbound oligonucleotide the conjugated antibodies were filtered 4 times on molecular weight cutoff filters (Amicon 50 KDa). Final wash and storage were performed in phosphate buffer with 0.5M sodium chloride and 0.1% Tween-20.

To assemble DNA duplex tag 0.2 ug of conjugated antibodies was mixed with 100 pmoles of bottom strand oligonucleotide in phosphate buffer with 0.6M Sodium Chloride and incubated for 30 min at 40° C.

```
v2_C_cycle1
                                          SEQ ID NO: 128:
TTTTGTTCTGCAAGATGCTACCGTTCGGz v2_C_cycle2
                                          SEQ ID NO: 129:
TTTTGtTTCTGCAAGATGCTACCGTTCGGz v2_C_cycle3
                                          SEQ ID NO: 130:
TTTTGCtTTCTGCAAGATGCTACCGTTCGGz v2_C_cycle4
                                          SEQ ID NO: 131:
TTTTGTCtTTCTGCAAGATGCTACCGTTCGGz v2_C_cycle5
                                          SEQ ID NO: 132:
TTTTGCcTCtTTCTGCAAGATGCTACCGTTCGGz v2_C_cycle6
                                          SEQ ID NO: 133:
TTTTGttttCcTCtTTCTGCAAGATGCTACCGTTCGGz v2_C_cycle7
                                          SEQ ID NO: 134:
TTTTGccttttCcTCtTTCTGCAAGATGCTACCGTTCGGz v2_C_cycle8
                                         (SEQ ID NO: 135)
TTTTGttcctttCcTCtTTCTGCAAGATGCTACCGTTCGGz v2_C_cycle9
                                         (SEQ ID NO: 136)
TTTTGcttcctttCcTCtTTCTGCAAGATGCTACCGTTCGGz v2_C_cycle10
                                         (SEQ ID NO: 137)
TTTTGtcttcctttCcTCtTTCTGCAAGATGCTACCGTTCGGz v2_C_cycle11
                                         (SEQ ID NO: 138)
TTTTGcctcttcctttCcTCtTTCTGCAAGATGCTACCGTTCGGz v2_U_cycle1
                                          SEQ ID NO: 139:
TTTTATTCTGCAAGATGCTACCGTTCGGz v2_U_cycle2
                                          SEQ ID NO: 140:
TTTTAtTTCTGCAAGATGCTACCGTTCGGz v2_U_cycle3
                                          SEQ ID NO: 141:
TTTTACtTTCTGCAAGATGCTACCGTTCGGz v2_U_cycle4
                                          SEQ ID NO: 142:
TTTTATCtTTCTGCAAGATGCTACCGTTCGGz
```

-continued

```
v2_U_cycle5
                                          SEQ ID NO: 143:
TTTTACcTCtTTCTGCAAGATGCTACCGTTCGGz v2_U_cycle6
                                          SEQ ID NO: 144:
TTTTAtttCcTCtTTCTGCAAGATGCTACCGTTCGGz v2_U_cycle7
                                          SEQ ID NO: 145:
TTTTAcctttCcTCtTTCTGCAAGATGCTACCGTTCGGz v2_U_cycle8
                                         (SEQ ID NO: 146)
TTTTAttcctttCcTCtTTCTGCAAGATGCTACCGTTCGGz v2_U_cycle9
                                         (SEQ ID NO: 147)
TTTTActtcctttCcTCtTTCTGCAAGATGCTACCGTTCGGz v2_U_cycle10
                                         (SEQ ID NO: 148)
TTTTAtcttcctttCcTCtTTCTGCAAGATGCTACCGTTCGGz v2_U_cycle11
                                         (SEQ ID NO: 149)
TTTTAcctcttcctttCcTCtTTCTGCAAGATGCTACCGTTCGGz
```

Mouse spleen and bone marrow cells were prepared according to standard procedure and fixed in 2% formaldehyde for 10 min at room temperature. Following fixation, cells were spun and either stored frozen at −80 in PBS with 5% DMSO or permeabilized by incubation in ice-cold methanol for 10 min. and further stored at −80° C. in methanol.

Before staining stored cells were washed with SM (0.5% BSA in PBS, 5mMEDTA) once and blocked for 30 min at room temperature in staining buffer (0.6M NaCl, 0.5% BSA, 50 ug/ml rat IgG, 200 ug/ml ssDNA, 5mMEDTA, 3 nmoles per ml of blocking oligonucleotide TTTTccctctcctcttcctttCcTCt-ddC in phosphate buffer pH 7.4). In case frozen sections were used tissue sections were picked by warm coverslips and immediately placed into dry ice without allowing the section to dry. Coverslips with sections were dipped for 30 sec into ethanol pre-chilled to dry-ice temperature, and transferred to SME with 4% formaldehyde for 20 min After that the fixed sections were washed twice in SM and further blocked in staining buffer for 30 min. Mouse spleen cells were stained in staining buffer for 2-3 h at room temperature with a mixture of conjugated antibodies taken at 0.2 ug of each antibody per 100 ul of solution. After staining cells were washed twice with SM05 (SM supplemented with NaCl up to 0.65M final concentration), then were allowed to adhere to poly-L-lysin coated coverslips and further fixed to coverslip surface by 20 min incubation with 5 mM BS3 crosslinker in PBS. Following methanol fixation/permeabilization cells were washed once with SM05, allowed to adhere to coverslip surface and further fixed to coverslip surface by 20 min incubation with 5 mM BS3 crosslinker in PBS. If frozen sections were used—following staining sections were washed twice by SM05 and fixed by 20 min incubation with 5 mM BS3 crosslinker in PBS. Following staining procedure and converting into planar form (in case of suspension cells) all kinds of samples were subjected to similar ABseq rendering protocol.

Coverslips with cells were washed twice with buffer 4 (10 mM Tris pH 6.5, 10 mM MgCl2, 150 mM NaCl, 0.1% Triton x100).

Staining was rendered by iterative incubation with polymerase reaction mixes. In odd cycles (1, 3, 5 . . . )-cells were incubated for 2 min in G-mix (150 nM dG, 150 nM dUssCy5, 150 nM dCssCy3, 25 ul NEB exo– Klenow per ml in buffer 4); wash 3 times with 405 (buffet 4 without MgCl and supplemented with NaCl up to final 0.65M); photographed; incubated 2 min in 50 mM TCEP in buffer 405; washed twice with 405; photographed; incubated for 1 min in freshly made 100 mM iodoacetamide in buffer 405; washed three times with buffer 4. In even cycles (2, 4, 6 . . . )-cells were incubated for 2 min in A-mix (150 nM dATP, 150 nM dUTPssCy5, 150 nM dCTPssCy3, 25 ul NEB exo– Klenow per ml in buffer 4); wash 3 times with 405 (buffet 4 without MgCl and supplemented with NaCl up to final 0.65M); photographed; incubated 4 min in 50 mM TCEP in buffer 405; washed twice with 405; photographed; incubated for 1 min in freshly made 100 mM iodoacetamide in buffer 405; washed three times with buffer #4. Reversibly labelled fluorescent nucleotide triphosphates were custom synthesized by Jena Bioscience.

Results

Figure 17:
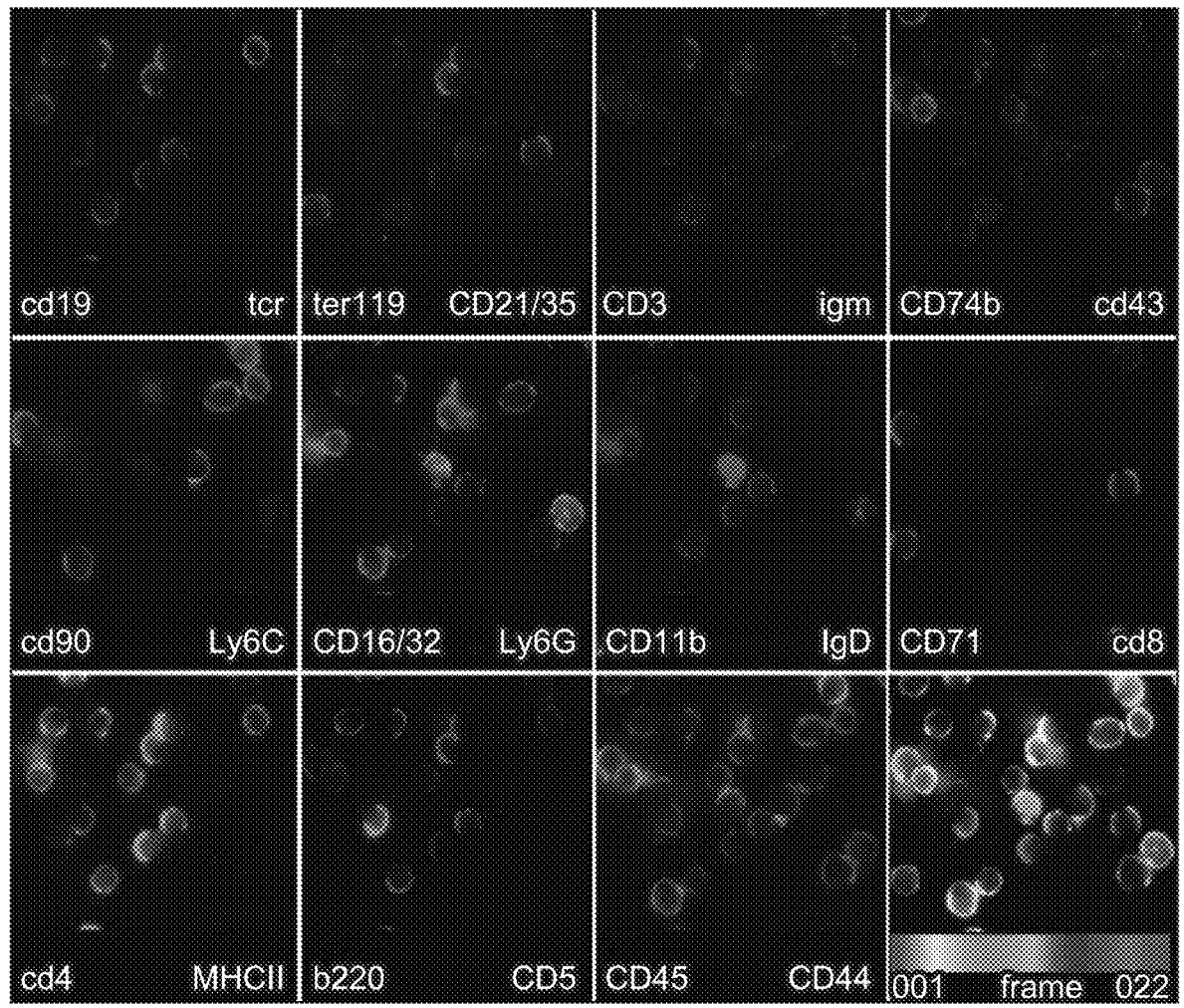
FIG. 17 shows fluorescent images of cells, showing the staining of 22 different antigens rendered by the iterative primer extension protocol. At each cycle one antigen-antibody-DNA complex incorporates dUTP—SS-Cy5 fluorophore (red) and one complex incorporates dCTP—SS-Cy3 (green), all other complexes receive an unlabelled 'walking' base (dGTP on odd cycles, dATP on even cycles).

ABseq was used to explore the variety of cellular subsets in mouse spleen and bone marrow using 22-antibody panel. Isolated spleen and bone marrow cells were barcoded by whole cell staining with NHS-PacBlu and NHS-Ax-488 dyes, mixed, stained with a panel of 22 antibodies tagged with DNA duplexes, attached to slide and rendered by ABseq in 11 primer extension and imaging iterations (FIG. 17). Conspicuously 22-color marker expression data on pseudocolored image bearing all marker expressing data proved to be impossible to parse visually due to proximity of colors in multi-color palette (FIG. 17, bottom right panel).

Example 4

Multipanel Design with Spacers

Materials and Methods

Antibody conjugation, cell staining and rendering was performed following the same experimental procedures as in section 4 (Co-detecting 22 antigens on dispersed spleen cells). Nine aliquots of spleen cells were stained separately with a different CD45 antibody-DNA conjugate. Conjugates for each panel were formed in the following way.

```
Panel1: CD45 conjugated to 146v2 (5'Maleimide-
ATAGCAGTCCAGCCGAACGGTAGCATCTTGCAGAA (SEQ ID NO:
174) and forming a DNA duplex with:
1.
                                    (SEQ ID NO: 150)
TTTTATTCTGCAAGATGCTACCGTTCGG-dideoxyC 2.
                                    (SEQ ID NO: 151)
TTTTAtTTCTGCAAGATGCTACCGTTCGGz-dideoxyC 3.
                                    (SEQ ID NO: 152)
TTTTACtTTCTGCAAGATGCTACCGTTCGGz-dideoxyC Panel2 CD45 conjugated to 146v2-ddC (5'Maleimide-
ATAGCAGTCCAGCCGAACGGTAGCATCTTGCAGAA-dideoxyC)
(SEQ ID NO: 153)  and forming a DNA duplex with:
4.
                                    (SEQ ID NO: 154)
TTTTAGCGATTAAGCGTGAACTTCTGCAAGATGCTACCGTTCGGdideoxyC
```

```
-continued
5.
                                    (SEQ ID NO: 155)
TTTTAtGCGATTAAGCGTGAACTTCTGCAAGATGCTACCGTTCGGzdideoxyC 6.
                                    (SEQ ID NO: 156)
TTTTACtGCGATTAAGCGTGAACTTCTGCAAGATGCTACCGTTCGGzdideoxyC Panel3 CD45 conjugated to 146v2-ddC (5'Maleimide-
ATAGCAGTCCAGCCGAACGGTAGCATCTTGCAGAA-dideoxyC)
(SEQ ID NO: 157) and forming a DNA duplex with:
7.
                                    (SEQ ID NO: 158)
TTTTACGCTAATTCGCACTTGTTCTGCAAGATGCTACCGTTCGGdideoxyC 8.
                                    (SEQ ID NO: 159)
TTTTAtCGCTAATTCGCACTTGTTCTGCAAGATGCTACCGTTCGGzdideoxyC 9.
                                    (SEQ ID NO: 160)
TTTTACtCGCTAATTCGCACTTGTTCTGCAAGATGCTACCGTTCGGzdideoxyC
```

After staining the cells were washed with washed twice with buffer 4 (10 mM Tris pH 6.5, 10 mM MgCl2, 150 mM NaCl, 0.1% Triton x100) to remove unbound antibody-DNA conjugates and then the aliquots of cells were mixed together and attached to a lysine-coated coverslip. Antigen staining was rendered in the following sequence of incubations: dGTP+dUTP-Cy5→dATP+dUTP-Cy5→dGTP+dUTP-Cy5→Incubation with 1 uM spacer1 (GTTCACGCTTAATCGC; SEQ ID NO:161) in buffer #4 for 20 minutes→dGTP+dUTP-Cy5→dATP+dUTP-Cy5→dGTP+dUTP-Cy5→Incubation with 1 uM spacer2 (CGCTAATTCGCACTTG; SEQ ID NO:162) in buffer #4 for 20 minutes→dGTP+dUTP-Cy5→dATP+dUTP-Cy5→dGTP+dUTP-Cy5 Imaging, fluorophore inactivation with 50 mM TCEP pH 7.0 and background blocking with iodoacetamide were performed after each step of rendering.

Results

Due to polymerase misincorporation errors the signal intensity of rendering by ABseq is expected to fall with increasing cycle numbers as observed in other studies on development of deep sequencing protocols utilizing sequential addition of individual nucleotides. To circumvent that and to avoid the use of extensively long DNA fragments linked to antibody the following amendment to the design was tested (FIG. 18, panel A). Large antibody panels can be split into subpanels such that the extension reaction on these subpanels is precluded by termination of the upper strand oligonucleotide with ddC, propyl or any other 3' terminating group. After finishing the extension of each subpanel, the next subpanel is activated by in situ hybridization of a short "activation" spacer, which does not bear any terminating moiety on its 3' end and thus initiates the consecutive cycles of primer extensions. This design was tested experimentally on 3 sequential 3-cycle panels (9 extension cycles in total)

(FIG. 18, panel B). Image quantification showed no significant reduction of ABseq rendering efficiency associated with on-slide hybridization of panel activating spacer oligonucleotide was observed and no signal carryover between the individual panels (FIG. 18, panel C).

Example 5

Multiplexed Single Molecule RNA Detection

Materials and Methods

NALM and Jurkat cell lines were grown to a density of 1 million/ml, fixed with 1.6% formaldehyde for 10 minutes and then transferred to ice-cold methanol. An aliquot of 200K cells was washed with PBSTR (PBS, 0.1% Tween-20 and 1:1000 Rnasin) and transferred to a hybridization buffer (1×SSC, 10% formamide, 10% vanadyl-ribonucleotide complex, 10% polyvinylsulfonic acid). DNA probe mixture was added to the final concentration of 100 nM and incubated at 40 C for 1 hour. Cells were washed 2 times with PBSTR at room temperature for 5 minutes and 2 times with a high salt buffer (4×SSC in PBSTR) at 40 degrees for 20 minutes, once again washed with PBSTR and transferred to a ligation solution (0.1 ul T4 DNA ligase (New England Biosciences), 5 ul 10× T4 ligase buffer (New England Biosciences), 45 ul H2O). Ligation proceeded for 1 h at 37 C. Then cells were transferred to amplification solution (1 ul of phi29 polymerase (Thermo Scientific), 5 ul of 10× polymerase buffer (Thermo Scientific), 1 ul of 10 mM dNTP mix, 43 ul of H$_2$O) and incubated at 30 C for 1 h. Cells were washed with PBSTR and incubated with 1 mM "RCA detection" oligonucleotide for 10 minutes at 37 C and transferred to Sequencing buffer (10 mM Tris pH 7.5, 10 mM MgCl2, 150 mM NaCl, 0.1% Triton x100, 1:50 Klenow polymerase (Thermo Scientific), 200 mM dUTP-Cy5 (Jena Biosciences)). Cells were washed twice with high salt wash buffer (10 mM Tris pH 7.5, 10 mM MgCl2, 650 mM NaCl, 0.1% Triton x100) and imaged using a florescent microscope.

Results

An on-slide primer extension protocol was applied to detect single molecules of human HLADRA mRNA in NALM pro-B-cell line. Jurkat T-cell lymphoma line was used as a negative control to assess the background. In order to enable single molecule mRNA detection, a signal amplification system was designed based on proximity ligation and rolling circle amplification (RCA). Five pairs of probes were designed in a way that the two oligos of each pair were complementary to directly adjacent 20-nt stretches of HLADRA mRNA and that the 3' region of the upstream oligonucleotide served as a splint for circularization of the downstream padlock oligonucleotide (FIG. 19, A) and also as a primer for the rolling circle amplification. After the complex assembly the cells were washed and treated with T4 DNA ligase to circularize the padlock oligonucleotide and the incubated with phi29 polymerase and dNTP mix to carry out the rolling circle amplification (FIG. 19, B). Amplification products were incubated with "RCA detect" oligonucleotide (FIG. 19, C) and then fluorescent dUTP-Cy5 was incorporated by a single base extension with Klenow to polymerase (FIG. 19, D). Cells were washed and imaged with a fluorescent microscope. Images of NALM cells that express HLADR show abundant punctate staining in the cytoplasm that corresponds to the RCA products (FIG. 19, E) and the Jurkat cells that are negative for HLADR show very few puncta (FIG. 19, F), demonstrating the high specificity of the proximity ligation-based detection of HLADRA mRNA.

```
HLA-DR padlock1      PACATTAaaatcctagcacagggactcAATTATTACTGAAACATACACTAAAGAT
                     Apa (SEQ ID NO: 163)

HLA-DR splint-primer1  ctcatcagcacagctatgatgaTAATGTTATCTT (SEQ ID NO: 164)

HLA-DR padlock2      PACATTAtagaactcggcctggatgatAATTATTACTGAAACATACACTAAAGAT
                     A (SEQ ID NO: 165)

HLA-DR splint-primer2  ctgattggtcaggattcagaTAATGTTATCTT (SEQ ID NO: 166)

HLA-DR padlock3      PACATTAtcaaagctggcaaatcgtccAATTATTACTGAAACATACACTAAAGAT
                     A (SEQ ID NO: 167)

HLA-DR splint-primer2  tggccaatgcaccttgagccTAATGTTATCTT (SEQ ID NO: 168)

HLA-DR padlock4      PACATTAtgatttccaggttggctttgAATTATTACTGAAACATACACTAAAGAT
                     A (SEQ ID NO: 169)

HLA-DR splint-primer2  atagttggagcgctttgtcaTAATGTTATCTT (SEQ ID NO: 170)

HLA-DR padlock5      PACATTAtttcgaagccacgtgacattAATTATTACTGAAACATACACTAAAGAT
                     A (SEQ ID NO: 171)

HLA-DR splint-primer2  ctgtggtgacaggttttccaTAATGTTATCTT (SEQ ID NO: 172)

RCA detect           CATACACTAAAGATAACAT (SEQ ID NO: 173)
```

What is claimed is:

1. A method of analyzing a planar sample, the method comprising:
   obtaining a labeled composition comprising:
   (a) a biological sample;
   (b) a plurality of capture agents;
   (c) a labeled oligonucleotide; and
   (d) a ligase;
       wherein, (i) the plurality of capture agents are linked to double-stranded oligonucleotides comprising a first strand and a second strand, wherein the ligase is configured to add the labeled oligonucleotide to the first strand or the second strand, and (ii) the plurality of capture agents are chemically cross-linked directly to the biological sample; and
   reading a signal generated by the labeled composition.

2. The method of claim 1, wherein the plurality of capture agents are cross-linked to the biological sample via a bifunctional cross-linker.

3. The method of claim 1, wherein the plurality of capture agents are cross-linked to the biological sample via an amine-to-amine crosslinker.

4. The method of claim 1, wherein the plurality of capture agents are cross-linked to the biological sample by formaldehyde or a disuccinimidyl crosslinker.

5. The method of claim 1, wherein the biological sample is planar.

6. The method of claim 1, wherein the biological sample is a tissue section.

7. The method of claim 1, wherein the biological sample is a tissue biopsy.

8. The method of claim 1, wherein the biological sample is a formalin-fixed paraffin embedded tissue section.

9. The method of claim 1, wherein the plurality of capture agents comprises a first capture agent linked to a first double-stranded oligonucleotide and a second capture agent linked to a second double-stranded oligonucleotide.

10. The method of claim 1, wherein the plurality of capture agents comprises at least 10 capture agents, each linked to a different double-stranded oligonucleotide.

11. The method of claim 1, wherein the double-stranded oligonucleotides linked to the plurality of capture agents are at least 10 nucleotides in length.

12. The method of claim 1, wherein the plurality of capture agents are antibodies.

13. The method of claim 12, wherein the antibodies are monoclonal antibodies.

14. The method of claim 1, wherein the plurality of capture agents are aptamers or oligonucleotide probes.

15. The method of claim 1, wherein the double-stranded oligonucleotides comprises an overhang.

16. The method of claim 1, wherein the labeled oligonucleotide comprises a fluorescent label.

17. The method of claim 1, wherein at least one of the plurality of capture agents comprises a fluorescent label.

18. The method of claim 1, wherein the signal is a fluorescent signal.

19. The method of claim 1, wherein reading comprises fluorescence microscopy.

20. The method of claim 1, wherein the method further comprises producing an image showing the pattern of binding of the plurality of capture agents chemically cross-linked directly to the biological sample.

* * * * *

SEQUENCE LISTING

<160> NUMBER OF SEQ ID NOS: 174

<210> SEQ ID NO 1
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is uridine
<220> FEATURE:
<221> NAME/KEY: misc_feature
<222> LOCATION: (5)..(5)
<223> OTHER INFORMATION: n is uridine
<220> FEATURE:
<221> NAME/KEY: misc_feature
<222> LOCATION: (9)..(9)
<223> OTHER INFORMATION: n is uridine
<220> FEATURE:
<221> NAME/KEY: misc_feature
<222> LOCATION: (13)..(13)
<223> OTHER INFORMATION: n is uridine

<400> SEQUENCE: 1
naaanaaana aan                                                        13

<210> SEQ ID NO 2
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 2
atttatttat tta                                                        13

<210> SEQ ID NO 3
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is uridine
<220> FEATURE:
<221> NAME/KEY: misc_feature
<222> LOCATION: (5)..(5)
<223> OTHER INFORMATION: n is uridine
<220> FEATURE:
<221> NAME/KEY: misc_feature
<222> LOCATION: (11)..(11)
<223> OTHER INFORMATION: n is uridine

<400> SEQUENCE: 3
naacnaacaa n                                                          11

<210> SEQ ID NO 4
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 4
attgttattg tta                                                        13

```
<210> SEQ ID NO 5
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: c is dideoxycytidine

<400> SEQUENCE: 5
ttctaggggg ggggggggtc gtcaagatgc taccgttcag gc                            42

<210> SEQ ID NO 6
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end

<400> SEQUENCE: 6
atagcgctac cctgaacggt agcatcttga cgac                                    34

<210> SEQ ID NO 7
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: c is dideoxycytidine

<400> SEQUENCE: 7
ttctaacgat ctagtcggtc gtcaagatgc taccgttcag gc                            42

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end

<400> SEQUENCE: 8
atagcgctac gcctgaacgg tagcatcttg acgac                                   35

<210> SEQ ID NO 9
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 9
ttctactctc tctctctgtc gtcaagatgc taccgttcag g                             41

<210> SEQ ID NO 10
<211> LENGTH: 35
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end

<400> SEQUENCE: 10
atagcgctac gcctgaacgg tagcatcttg acgac                              35

<210> SEQ ID NO 11
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 11
ttctactcct ttcctctgtc gtcaagatgc taccgttcag g                       41

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end

<400> SEQUENCE: 12
atagcgctac gcctgaacgg tagcatcttg acgac                              35

<210> SEQ ID NO 13
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(5)
<223> OTHER INFORMATION: c is dideoxycytidine

<400> SEQUENCE: 13
atagcgctac gcctgaacgg tagcatcttg acgac                              35

<210> SEQ ID NO 14
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(27)
<223> OTHER INFORMATION: n is a, c, g, or t
<220> FEATURE:
<221> NAME/KEY: misc_feature
<222> LOCATION: (52)..(52)
<223> OTHER INFORMATION: c is dideoxycytidine

<400> SEQUENCE: 14
tttttannnn nnnnnnnnnn nnnnnnngtc gtcaagatgc taccgttcag gc           52
```

```
<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 15
atagcgctac gcctgaacgg tagcatcttg acgac                              35

<210> SEQ ID NO 16
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(28)
<223> OTHER INFORMATION: n is a, c, g, or t
<220> FEATURE:
<221> NAME/KEY: misc_feature
<222> LOCATION: (53)..(53)
<223> OTHER INFORMATION: c is dideoxycytidine

<400> SEQUENCE: 16
tttttacnnn nnnnnnnnnn nnnnnnnngt cgtcaagatg ctaccgttca ggc          53

<210> SEQ ID NO 17
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 17
atagcgctac gcctgaacgg tagcatcttg acgac                              35

<210> SEQ ID NO 18
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(29)
<223> OTHER INFORMATION: n is a, c, g, or t
<220> FEATURE:
<221> NAME/KEY: misc_feature
<222> LOCATION: (54)..(54)
<223> OTHER INFORMATION: c is dideoxycytidine

<400> SEQUENCE: 18
``` ttttttactnn nnnnnnnnnn nnnnnnnnng tcgtcaagat gctaccgttc aggc          54

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(5)
<223> OTHER INFORMATION: c is dideoxycytidine

<400> SEQUENCE: 19
atagcgctac gcctgaacgg tagcatcttg acgac                                35

<210> SEQ ID NO 20
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(27)
<223> OTHER INFORMATION: n is a, c, g, or t
<220> FEATURE:
<221> NAME/KEY: misc_feature
<222> LOCATION: (52)..(52)
<223> OTHER INFORMATION: c is dideoxycytidine

<400> SEQUENCE: 20
tttttannnn nnnnnnnnnn nnnnnnngtc gtcaagatgc taccgttcag gc             52

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 21
atagcgctac gcctgaacgg tagcatcttg acgac                                35

<210> SEQ ID NO 22
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(28)
<223> OTHER INFORMATION: n is a, c, g, or t
<220> FEATURE:
<221> NAME/KEY: misc_feature
<222> LOCATION: (53)..(53)
<223> OTHER INFORMATION: c is dideoxycytidine

<400> SEQUENCE: 22 ttttttacnnn nnnnnnnnnn nnnnnnnngt cgtcaagatg ctaccgttca ggc    53

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 23
atagcgctac gcctgaacgg tagcatcttg acgac    35

<210> SEQ ID NO 24
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(29)
<223> OTHER INFORMATION: n is a, c, g, or t
<220> FEATURE:
<221> NAME/KEY: misc_feature
<222> LOCATION: (54)..(54)
<223> OTHER INFORMATION: c is dideoxycytidine

<400> SEQUENCE: 24
tttttactnn nnnnnnnnnn nnnnnnnnng tcgtcaagat gctaccgttc aggc    54

<210> SEQ ID NO 25
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 25
atagcgctac gcctgaacgg tagcatcttg acgac    35

<210> SEQ ID NO 26
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(27)
<223> OTHER INFORMATION: n is a, c, g, or t
<220> FEATURE:
<221> NAME/KEY: misc_feature
<222> LOCATION: (52)..(52)
<223> OTHER INFORMATION: c is dideoxycytidine

```
<400> SEQUENCE: 26
tttttannnn nnnnnnnnnn nnnnnnngtc gtcaagatgc taccgttcag gc    52

<210> SEQ ID NO 27
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 27
atagcgctac gcctgaacgg tagcatcttg acgac    35

<210> SEQ ID NO 28
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(28)
<223> OTHER INFORMATION: n is a, c, g, or t
<220> FEATURE:
<221> NAME/KEY: misc_feature
<222> LOCATION: (53)..(53)
<223> OTHER INFORMATION: c is dideoxycytidine

<400> SEQUENCE: 28
tttttacnnn nnnnnnnnnn nnnnnnnngt cgtcaagatg ctaccgttca ggc    53

<210> SEQ ID NO 29
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end
<220> FEATURE:
<221> NAME/KEY: misc_feature
<222> LOCATION: (35)..(35)
<223> OTHER INFORMATION: c is dideoxycytidine

<400> SEQUENCE: 29
atagcgctac gcctgaacgg tagcatcttg acgac    35

<210> SEQ ID NO 30
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(29)
<223> OTHER INFORMATION: n is a, c, g, or t
<220> FEATURE:
<221> NAME/KEY: misc_feature
<222> LOCATION: (54)..(54)
<223> OTHER INFORMATION: c is dideoxycytidine
```

```
<400> SEQUENCE: 30
tttttactnn nnnnnnnnnn nnnnnnnnng tcgtcaagat gctaccgttc aggc            54

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
cctgaacggt agcatcttga cgac                                             24

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quncher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 32
aaaaaaaaac gcggcccgg                                                   19

<210> SEQ ID NO 33
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 33
ccgggccgcg ttttttttta gtcgtcaaga tgctaccgtt cagg                       44

<210> SEQ ID NO 34
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: linked to a fluorophore at the 3' end

<400> SEQUENCE: 34
cctgaacggt agcatcttga cgactaaaaa aaaacgcggc ccgg                       44

<210> SEQ ID NO 35
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 35
ccgggccgcg ttttttttta gtcgtcaaga tgctaccgtt cagg                       44

<210> SEQ ID NO 36
```

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
cctgaacggt agcatcttga cgac                                              24

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 37
aaaaaaaaac gcggcccgg                                                    19

<210> SEQ ID NO 38
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 38
ccgggccgcg tttttttta gtcgtcaaga tgctaccgtt cagg                         44

<210> SEQ ID NO 39
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 39
cctgaacggt agcatcttga cgac                                              24

<210> SEQ ID NO 40
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 40
aaaaaaaaac gcggcccgg                                                    19

<210> SEQ ID NO 41
<211> LENGTH: 45
<212> TYPE: DNA
<213> ORGANISM: Artificial Sequence
```

```
<220> FEATURE:
<223> OTHER INFORMATION: Synthetic oligonucleotide

<400> SEQUENCE: 41
ccgggccgcg ttttttttta cgtcgtcaag atgctaccgt tcagg          45

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 42
cctgaacggt agcatcttga cgac                                 24

<210> SEQ ID NO 43
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 43
aaaaaaaaac gcggcccgg                                       19

<210> SEQ ID NO 44
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 44
ccgggccgcg ttttttttc aggtcgtcaa gatgctaccg ttcagg          46

<210> SEQ ID NO 45
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: linked to a fluorophore at the 3' end

<400> SEQUENCE: 45
cctgaacggt agcatcttga cgactaaaaa aaaacgcggc ccgg           44

<210> SEQ ID NO 46
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 46
ccgggccgcg ttttttttta gtcgtcaaga tgctaccgtt cagg           44
```

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 47
cctgaacggt agcatcttga cgac                                          24

<210> SEQ ID NO 48
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 48
aaaaaaaaac gcggcccgg                                                19

<210> SEQ ID NO 49
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 49
ccgggccgcg ttttttttta cgtcgtcaag atgctaccgt tcagg                   45

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 50
cctgaacggt agcatcttga cgac                                          24

<210> SEQ ID NO 51
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 51
aaaaaaaaac gcggcccgg                                                19

<210> SEQ ID NO 52
<211> LENGTH: 46

```
<212> TYPE: DNA
<213> ORGANISM: Artificial Sequence
<220> FEATURE:
<223> OTHER INFORMATION: Synthetic oligonucleotide

<400> SEQUENCE: 52
ccgggccgcg ttttttttc aggtcgtcaa gatgctaccg ttcagg                46

<210> SEQ ID NO 53
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 53
cctgaacggt agcatcttga cgactaaaaa aaaacgcggc ccgg                 44

<210> SEQ ID NO 54
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 54
ccgggccgcg tttttttta gtcgtcaaga tgctaccgtt cagg                  44

<210> SEQ ID NO 55
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 55
cctgaacggt agcatcttga cgacg                                      25

<210> SEQ ID NO 56
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: linked to a fluorophore at the 3' end

<400> SEQUENCE: 56
aaaaaaaaac gcggcccgg                                             19

<210> SEQ ID NO 57
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 57
ccgggccgcg tttttttta cgtcgtcaag atgctaccgt tcagg                 45

<210> SEQ ID NO 58
<211> LENGTH: 25
<212> TYPE: DNA
<213> ORGANISM: Artificial Sequence
<220> FEATURE:
```

```
<223> OTHER INFORMATION: Synthetic oligonucleotide

<400> SEQUENCE: 58
cctgaacggt agcatcttga cgacc                                        25

<210> SEQ ID NO 59
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 59
aaaaaaaaac gcggcccgg                                               19

<210> SEQ ID NO 60
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 60
ccgggccgcg ttttttttttc aggtcgtcaa gatgctaccg ttcagg                 46

<210> SEQ ID NO 61
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 61
cctgaacggt agcatcttga cgactaaaaa aaaacgcggc ccgg                    44

<210> SEQ ID NO 62
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 62
ccgggccgcg ttttttttta gtcgtcaaga tgctaccgtt cagg                    44

<210> SEQ ID NO 63
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (63)..(63)
<223> OTHER INFORMATION: linked to a fluorophore at the 3' end

<400> SEQUENCE: 63
cctgaacggt agcatcttga cgacgtaaaa aaaacgcgg cccgg                    45
```

```
<210> SEQ ID NO 64
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 64
ccgggccgcg ttttttttta cgtcgtcaag atgctaccgt tcagg            45

<210> SEQ ID NO 65
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 65
cctgaacggt agcatcttga cgacct                                 26

<210> SEQ ID NO 66
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to a quencher at the 5' end
<220> FEATURE:
<221> NAME/KEY: misc_feature
<222> LOCATION: (19)..(19)
<223> OTHER INFORMATION: linked to a fluorophore at the 3' end

<400> SEQUENCE: 66
aaaaaaaaac gcggcccgg                                         19

<210> SEQ ID NO 67
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 67
ccgggccgcg ttttttttc aggtcgtcaa gatgctaccg ttcagg            46

<210> SEQ ID NO 68
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)..(34)
<223> OTHER INFORMATION: linked to an antibody at the 3' end

<400> SEQUENCE: 68
atagagcgag ccagtgctag ggtgagtggc caag                        34

<210> SEQ ID NO 69
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (34)..(34)
<223> OTHER INFORMATION: linked to an antibody at the 3' end

<400> SEQUENCE: 69
atagagcgag ccagtgctag ggtgagtggc caag                            34

<210> SEQ ID NO 70
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 70
gcactggctc gctcta                                                16

<210> SEQ ID NO 71
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)..(34)
<223> OTHER INFORMATION: linked to an antibody at the 3' end

<400> SEQUENCE: 71
atagagcgag ccagtgctag ggtgagtggc caag                            34

<210> SEQ ID NO 72
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: linked to Cy5 at the 3' end

<400> SEQUENCE: 72
gcactggctc gctctan                                               17

<210> SEQ ID NO 73
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)..(34)
<223> OTHER INFORMATION: linked to an antibody at the 3' end

<400> SEQUENCE: 73
atagagcgag ccagtgctag ggtgagtggc caag                            34

<210> SEQ ID NO 74
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 74 gcactggc                                                          8
```

```
<210> SEQ ID NO 75
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (35)..(35)
<223> OTHER INFORMATION: linked to an antibody at the 3' end

<400> SEQUENCE: 75
catagagcga gccagtgcta gggtgagtgg ccaag                              35

<210> SEQ ID NO 76
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: linked to Cy5 at the 3' end

<400> SEQUENCE: 76
gcactggctc gctctan                                                 17

<210> SEQ ID NO 77
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (35)..(35)
<223> OTHER INFORMATION: linked to an antibody at the 3' end

<400> SEQUENCE: 77
caatgtccag gccagtgcta gggtgagtgg ccaag                              35

<210> SEQ ID NO 78
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 78
gcactggctc gctcta                                                  16

<210> SEQ ID NO 79
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (35)..(35)
<223> OTHER INFORMATION: linked to an antibody at the 3' end

<400> SEQUENCE: 79
caagtcagtg accagtgcta gggtgagtgg ccaag                              35

<210> SEQ ID NO 80
```

```
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 80
gcactggctc gctcta                                                      16

<210> SEQ ID NO 81
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to Cy5 at the 5' end
<220> FEATURE:
<221> NAME/KEY: misc_feature
<222> LOCATION: (18)..(35)
<223> OTHER INFORMATION: n is a, c, g, or t

<400> SEQUENCE: 81
acgtacgctc gtgccgcnnn nnnnnnnnnn nnnnn                                  35

<210> SEQ ID NO 82
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: linked to Cy3 at the 3' end

<400> SEQUENCE: 82
gcggcacgag cgtacgn                                                     17

<210> SEQ ID NO 83
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to Cy5 at the 5' end
<220> FEATURE:
<221> NAME/KEY: misc_feature
<222> LOCATION: (18)..(35)
<223> OTHER INFORMATION: n is a, c, g, or t

<400> SEQUENCE: 83
acctgcgctc gtgccgcnnn nnnnnnnnnn nnnnn                                  35

<210> SEQ ID NO 84
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 84
gcggcacgag cgtacg                                                      16
```

```
<210> SEQ ID NO 85
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to Cy5 at the 5' end
<220> FEATURE:
<221> NAME/KEY: misc_feature
<222> LOCATION: (18)..(35)
<223> OTHER INFORMATION: n is a, c, g, or t

<400> SEQUENCE: 85
agcatcgctc gtgccgcnnn nnnnnnnnn nnnnn                           35

<210> SEQ ID NO 86
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 86
gcggcacgag cgtacg                                                16

<210> SEQ ID NO 87
<211> LENGTH: 50
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: linked to an antibody at the 5' end

<400> SEQUENCE: 87
gaaccggtga gtgggatagc gctacgcctg aacggtagca tcttgacgac           50

<210> SEQ ID NO 88
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: c is dideoxycytidine

<400> SEQUENCE: 88
tttttagtcg tcaagatgct accgttcagg c                               31

<210> SEQ ID NO 89
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 89
cctgaacggt agcatcttga cgac                                       24

<210> SEQ ID NO 90
<211> LENGTH: 31
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: c is dideoxycytidine

<400> SEQUENCE: 90
tttttagtcg tcaagatgct accgttcagg c                               31

<210> SEQ ID NO 91
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 91
cctgaacggt agcatcttga cgac                                       24

<210> SEQ ID NO 92
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (32)..(32)
<223> OTHER INFORMATION: c is dideoxycytidine

<400> SEQUENCE: 92
tttttatgtc gtcaagatgc taccgttcag gc                              32

<210> SEQ ID NO 93
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 93
cctgaacggt agcatcttga cgac                                       24

<210> SEQ ID NO 94
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 94
atgcacgtcg tcaagatgct accgtt                                     26

<210> SEQ ID NO 95
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 95
cctgaacggt agcatcttga cgac                                       24

<210> SEQ ID NO 96
<211> LENGTH: 27
```

```
<212> TYPE: DNA
<213> ORGANISM: Artificial sequence
<220> FEATURE:
<223> OTHER INFORMATION: Synthetic oligonucleotide

<400> SEQUENCE: 96
atgcatcgtc gtcaagatgc taccgtt                                        27

<210> SEQ ID NO 97
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 97
cctgaacggt agcatcttga cgacg                                          25

<210> SEQ ID NO 98
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 98
atgcacgtcg tcaagatgct accgtt                                         26

<210> SEQ ID NO 99
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 99
cctgaacggt agcatcttga cgacg                                          25

<210> SEQ ID NO 100
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 100
atgcatcgtc gtcaagatgc taccgtt                                        27

<210> SEQ ID NO 101
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 101
cctgaacggt agcatcttga cgacgtgcat                                     30

<210> SEQ ID NO 102
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 102
```
atgcacgtcg tcaagatgct accgtt                                                 26

<210> SEQ ID NO 103
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 103
cctgaacggt agcatcttga cgacgtgcat                                             30

<210> SEQ ID NO 104
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 104
atgcatcgtc gtcaagatgc taccgtt                                                27

<210> SEQ ID NO 105
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 105
cctgaacggt agcatcttga cgacgtgcat                                             30

<210> SEQ ID NO 106
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 106
atgcacgtcg tcaagatgct accgtt                                                 26

<210> SEQ ID NO 107
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 107
cctgaacggt agcatcttga cgacg                                                  25

<210> SEQ ID NO 108
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 108
atgcatcgtc gtcaagatgc taccgtt                                                27

<210> SEQ ID NO 109
<211> LENGTH: 29
<212> TYPE: DNA
<213> ORGANISM: Artificial sequence

```
<220> FEATURE:
<223> OTHER INFORMATION: Synthetic oligonucleotide

<400> SEQUENCE: 109
cctgaacggt agcatcttga cgactgcat                                      29

<210> SEQ ID NO 110
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 110
atgcacgtcg tcaagatgct accgtt                                         26

<210> SEQ ID NO 111
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 111
cctgaacggt agcatcttga cgacg                                          25

<210> SEQ ID NO 112
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 112
atgcatcgtc gtcaagatgc taccgtt                                        27

<210> SEQ ID NO 113
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 113
cctgaacggt agcatcttga cgacgtgcat                                     30

<210> SEQ ID NO 114
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 114
atgcacgtcg tcaagatgct accgtt                                         26

<210> SEQ ID NO 115
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 115
cctgaacggt agcatcttga cgacga                                         26
```

<210> SEQ ID NO 116
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 116
atgcatcgtc gtcaagatgc taccgtt                                27

<210> SEQ ID NO 117
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 117
cctgaacggt agcatcttga cgacgtgcat                             30

<210> SEQ ID NO 118
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 118
atgcacgtcg tcaagatgct accgtt                                 26

<210> SEQ ID NO 119
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 119
cctgaacggt agcatcttga cgacgatgca t                           31

<210> SEQ ID NO 120
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 120
atgcatcgtc gtcaagatgc taccgtt                                27

<210> SEQ ID NO 121
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 121
cctgaacggt agcatcttga cgacgtgcat                             30

<210> SEQ ID NO 122
<211> LENGTH: 26
<212> TYPE: DNA
<213> ORGANISM: Artificial sequence
<220> FEATURE:
<223> OTHER INFORMATION: Synthetic oligonucleotide

```
<400> SEQUENCE: 122
atgcacgtcg tcaagatgct accgtt                                          26

<210> SEQ ID NO 123
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 123
cctgaacggt agcatcttga cgacgatgca t                                    31

<210> SEQ ID NO 124
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 124
atgcatcgtc gtcaagatgc taccgtt                                         27

<210> SEQ ID NO 125
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 125
atgctaccgt taattattac tgaaacatac actaaagata acattattct gcaag          55

<210> SEQ ID NO 126
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 126
tgaaacatac actaaaga                                                   18

<210> SEQ ID NO 127
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 127
gcatcttgca gaa                                                        13

<210> SEQ ID NO 128
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 128
ttttgttctg caagatgcta ccgttcgg                                        28

<210> SEQ ID NO 129
```

```
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 129
ttttgtttct gcaagatgct accgttcgg                                        29

<210> SEQ ID NO 130
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 130
ttttgctttc tgcaagatgc taccgttcgg                                       30

<210> SEQ ID NO 131
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 131
ttttgtcttt ctgcaagatg ctaccgttcg g                                     31

<210> SEQ ID NO 132
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 132
ttttgcctct ttctgcaaga tgctaccgtt cgg                                   33

<210> SEQ ID NO 133
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 133
ttttgtttcc tctttctgca agatgctacc gttcgg                                36

<210> SEQ ID NO 134
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 134
ttttgccttt cctctttctg caagatgcta ccgttcgg                              38

<210> SEQ ID NO 135
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 135
```
ttttgttcct ttcctctttc tgcaagatgc taccgttcgg    40

<210> SEQ ID NO 136
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 136
ttttgcttcc tttcctcttt ctgcaagatg ctaccgttcg g    41

<210> SEQ ID NO 137
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 137
ttttgtcttc ctttcctctt tctgcaagat gctaccgttc gg    42

<210> SEQ ID NO 138
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 138
ttttgcctct tcctttcctc tttctgcaag atgctaccgt tcgg    44

<210> SEQ ID NO 139
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 139
ttttattctg caagatgcta ccgttcgg    28

<210> SEQ ID NO 140
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 140
ttttatttct gcaagatgct accgttcgg    29

<210> SEQ ID NO 141
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 141
ttttactttc tgcaagatgc taccgttcgg    30

<210> SEQ ID NO 142
<211> LENGTH: 31
<212> TYPE: DNA

```
<213> ORGANISM: Artificial sequence
<220> FEATURE:
<223> OTHER INFORMATION: Synthetic oligonucleotide

<400> SEQUENCE: 142 ttttatctttt ctgcaagatg ctaccgttcg g                              31

<210> SEQ ID NO 143
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 143
ttttacctct ttctgcaaga tgctaccgtt cgg                             33

<210> SEQ ID NO 144
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 144
ttttatttcc tctttctgca agatgctacc gttcgg                          36

<210> SEQ ID NO 145
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 145
ttttaccttt cctctttctg caagatgcta ccgttcgg                        38

<210> SEQ ID NO 146
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 146
ttttattcct ttcctctttc tgcaagatgc taccgttcgg                      40

<210> SEQ ID NO 147
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 147
ttttacttcc tttcctcttt ctgcaagatg ctaccgttcg g                    41

<210> SEQ ID NO 148
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 148
ttttatcttc ctttcctctt tctgcaagat gctaccgttc gg                   42
```

<210> SEQ ID NO 149
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 149
ttttacctct tcctttcctc tttctgcaag atgctaccgt tcgg           44

<210> SEQ ID NO 150
<211> LENGTH: 29
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (29)..(29)
<223> OTHER INFORMATION: n = dideoxyC

<400> SEQUENCE: 150
ttttattctg caagatgcta ccgttcggn                            29

<210> SEQ ID NO 151
<211> LENGTH: 30
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (30)..(30)
<223> OTHER INFORMATION: n = dideoxyC

<400> SEQUENCE: 151
ttttatttct gcaagatgct accgttcggn                           30

<210> SEQ ID NO 152
<211> LENGTH: 31
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: n = dideoxyC

<400> SEQUENCE: 152
ttttactttc tgcaagatgc taccgttcgg n                         31

<210> SEQ ID NO 153
<211> LENGTH: 36
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (36)..(36)
<223> OTHER INFORMATION: n = dideoxyC

<400> SEQUENCE: 153
atagcagtcc agccgaacgg tagcatcttg cagaan                    36

<210> SEQ ID NO 154

```
<211> LENGTH: 45
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (45)..(45)
<223> OTHER INFORMATION: n = dideoxyC

<400> SEQUENCE: 154
ttttagcgat taagcgtgaa cttctgcaag atgctaccgt tcggn          45

<210> SEQ ID NO 155
<211> LENGTH: 46
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (46)..(46)
<223> OTHER INFORMATION: n = dideoxyC

<400> SEQUENCE: 155
ttttatgcga ttaagcgtga acttctgcaa gatgctaccg ttcggn         46

<210> SEQ ID NO 156
<211> LENGTH: 47
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (47)..(47)
<223> OTHER INFORMATION: n = dideoxyC

<400> SEQUENCE: 156
ttttactgcg attaagcgtg aacttctgca agatgctacc gttcggn        47

<210> SEQ ID NO 157
<211> LENGTH: 36
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (36)..(36)
<223> OTHER INFORMATION: n = dideoxyC

<400> SEQUENCE: 157
atagcagtcc agccgaacgg tagcatcttg cagaan                    36

<210> SEQ ID NO 158
<211> LENGTH: 45
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (45)..(45)
<223> OTHER INFORMATION: n = dideoxyC

<400> SEQUENCE: 158
ttttacgcta attcgcactt gttctgcaag atgctaccgt tcggn          45
```

<210> SEQ ID NO 159
<211> LENGTH: 46
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (46)..(46)
<223> OTHER INFORMATION: n = dideoxyC

<400> SEQUENCE: 159
ttttatcgct aattcgcact tgttctgcaa gatgctaccg ttcggn         46

<210> SEQ ID NO 160
<211> LENGTH: 47
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (47)..(47)
<223> OTHER INFORMATION: n = dideoxyC

<400> SEQUENCE: 160
ttttactcgc taattcgcac ttgttctgca agatgctacc gttcggn         47

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
gttcacgctt aatcgc         16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 162
cgctaattcg cacttg         16

<210> SEQ ID NO 163
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 163
acattaaaat cctagcacag ggactcaatt attactgaaa catacactaa agata         55

<210> SEQ ID NO 164
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 164
ctcatcagca cagctatgat gataatgtta tctt         34

<210> SEQ ID NO 165
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 165
acattataga actcggcctg gatgataatt attactgaaa catacactaa agata    55

<210> SEQ ID NO 166
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 166
ctgattggtc aggattcaga taatgttatc tt    32

<210> SEQ ID NO 167
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 167
acattatcaa agctggcaaa tcgtccaatt attactgaaa catacactaa agata    55

<210> SEQ ID NO 168
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 168
tggccaatgc accttgagcc taatgttatc tt    32

<210> SEQ ID NO 169
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 169
acattatgat ttccaggttg gctttgaatt attactgaaa catacactaa agata    55

<210> SEQ ID NO 170
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 170
atagttggag cgctttgtca taatgttatc tt    32

<210> SEQ ID NO 171
<211> LENGTH: 55
<212> TYPE: DNA
<213> ORGANISM: Artificial sequence
<220> FEATURE:
<223> OTHER INFORMATION: Synthetic oligonucleotide

```
<400> SEQUENCE: 171
acattatttc gaagccacgt gacattaatt attactgaaa catacactaa agata        55

<210> SEQ ID NO 172
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 172
ctgtggtgac aggttttcca taatgttatc tt                                32

<210> SEQ ID NO 173
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 173
catacactaa agataacat                                               19

<210> SEQ ID NO 174
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 174
atagcagtcc agccgaacgg tagcatcttg cagaa                             35
```